(12) United States Patent
Schomaker et al.

(10) Patent No.: US 9,221,842 B2
(45) Date of Patent: Dec. 29, 2015

(54) BICYCLIC METHYLENE AZIRIDINES AND REACTIONS THEREOF

(75) Inventors: Jennifer Schomaker, Madison, WI (US); Luke Boralsky, San Francisco, CA (US); John Hershberger, Clinton, NY (US); Jared Rigoli, Madison, WI (US); Christopher S. Adams, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 230 days.

(21) Appl. No.: 13/598,388

(22) Filed: Aug. 29, 2012

(65) Prior Publication Data

US 2013/0079511 A1 Mar. 28, 2013

Related U.S. Application Data

(60) Provisional application No. 61/528,596, filed on Aug. 29, 2011.

(51) Int. Cl.
| | |
|---|---|
| *C07D 498/04* | (2006.01) |
| *C07D 498/10* | (2006.01) |
| *C07D 515/04* | (2006.01) |
| *C07D 263/22* | (2006.01) |
| *C07D 265/10* | (2006.01) |
| *C07D 267/06* | (2006.01) |
| *C07D 498/20* | (2006.01) |
| *C07D 291/02* | (2006.01) |
| *C07D 291/06* | (2006.01) |

(52) U.S. Cl.
CPC ............ *C07D 515/04* (2013.01); *C07D 263/22* (2013.01); *C07D 265/10* (2013.01); *C07D 267/06* (2013.01); *C07D 291/02* (2013.01); *C07D 291/06* (2013.01); *C07D 498/04* (2013.01); *C07D 498/10* (2013.01); *C07D 498/20* (2013.01)

(58) Field of Classification Search
CPC ... C07D 498/04; C07D 498/10; C07D 515/04
USPC .......... 540/488, 543, 544, 552; 544/2, 71, 92, 544/97; 548/221
See application file for complete search history.

(56) References Cited

U.S. PATENT DOCUMENTS

2009/0012120 A1 1/2009 Borhan et al.

OTHER PUBLICATIONS

Atkinson et al., "Nitrene addition to allenes 1,4-Diazaspiro [2 2 ] pentanes," Tetrahedron Letters (1975) 48: 4305-4306.
Bingham et al., "Reaction of carbethoxynitrene with allenes," J. Org. Chem. (1975) 40 (2): 224-228.
Boralsky et al., "Allene functionalization via bicyclic methylene aziridines," Organic Letters (2011) 13 (8): 1924-1927.
Feast et al., "The intramolecular amination of allenes," Chem. Commun. (2010) 46: 2835-2837.
Grigg et al., "C-H amination/cyclocarbonylation of allene carbamates: a versatile platform for the synthesis of α,β-unsaturated •-lactams," Tetrahedron (2011) 67: 4318-4326.
Hayes et al., "Multicomponent reactions involving 2-methyleneaziridines: Rapid synthesis of 1,3-disubstituted propanones," J. Org. Chem. (2002) 67: 935-942.
Margathe et al., "Solid-phase, multicomponent reactions of methyleneaziridines: Synthesis of 1,3-disubstituted propanones," Organic Letters (2005) 7 (22): 4987-4990.
Robertson et al., "Structure and reactivity of bicyclic methylene aziridines prepared by intramolecular aziridination of allenes," Organic & Biomolecular Chemistry (2010) 8: 3060-3063.
Shipman, M., "Methyleneaziridines: Unusual vehicles for organic synthesis," SYNLETT (2006) 19: 3205-3217.
International Search Report for corresponding International Application No. PCT/US2012/052903 mailed on Nov. 27, 2012.
Written Opinion for corresponding International Application No. PCT/US2012/052903 mailed on Nov. 27, 2012.

*Primary Examiner* — Brenda Coleman

(74) *Attorney, Agent, or Firm* — Joseph T. Leone, Esq.; DeWitt Ross & Stevens S.C.

(57) ABSTRACT

The oxidative functionalization of olefins is a common method for the formation of vicinal carbon-heteroatom bonds. However, oxidative methods to transform allenes into synthetic motifs containing three contiguous carbon-heteroatom bonds are much less developed. The use of bicyclic methylene aziridines (MAs), prepared via intramolecular allene aziridination, as scaffolds for functionalization of all three allene carbons, among other reactions, is described herein.

12 Claims, 6 Drawing Sheets

BICYCLIC METHYLENE AZIRIDINES AND REACTIONS THEREOF

RELATED APPLICATIONS

This application claims priority under 35 U.S.C. §119(e) to U.S. Provisional Patent Application No. 61/528,596, filed Aug. 29, 2011, which is incorporated herein by reference.

BACKGROUND OF THE INVENTION

Many pharmaceuticals and other biologically active molecules contain sequences of at least three contiguous heteroatom-bearing carbons (triads). Important examples compounds that include such triads include Tamiflu® (oseltamivir phosphate) and Relenza® (zanamivir).

Molecules containing sequences of at least three contiguous heteroatom-bearing carbons are difficult to prepare, while synthetic methods for preparing two continuous heteroatom-bearing carbons are much further developed. Olefins are popular substrates for a host of oxidative transformations designed to introduce new C—N bonds into molecules. For example, the oxidative functionalization of olefins is a common method for the formation of vicinal carbon-heteroatom bonds. However, motifs having three contiguous heteroatom-bearing carbons can be difficult to prepare directly from simple hydrocarbon precursors, even reactive moieties such as olefins. Even more problematic is that the triads are difficult to prepare in enantioenriched form.

While much is known about the oxidative functionalization of olefins, considerably less is known about the oxidations of allenes, despite the potential to efficiently generate three new contiguous heteroatom-bearing chiral centers. New methods for the oxidation of allenes are therefore needed to add important flexibility to current synthetic methods. New methods for the preparation of synthetic motifs containing three contiguous carbon-heteroatom are also needed, for example, to provide more efficient syntheses of important biologically active molecules.

Additionally, chiral N,N-aminals are structural motifs found in many pharmaceuticals and biologically active natural products, such as the pyrroloindoline alkaloids, the phakellin-type pyrrole-imidazole alkaloids, and the lycoposerramines, many of which exhibit promising therapeutic activity. However, there are very few methods for the efficient preparation of chiral N,N-aminals. Thus, new methods are needed for the synthesis of N,N-aminals from readily available starting materials or intermediates.

SUMMARY

The invention provides efficient processes to prepare asymmetric, heteroatom-bearing stereotriads and tetrads via allene oxidation. The substrates include easily accessible enantioenriched allenes and the methods provide for flexibility in the number and type of heteroatoms that can be stereoselectively introduced into a hydrocarbon chain or ring. The methods allow for the transfer of chirality from an enantioenriched allene to three new carbon-heteroatom bonds. These stereodefined heteroatom-bearing triads and tetrads can be incorporated into biologically active molecules, including modified aminoglycosides and neuraminidase inhibitors.

Accordingly, the invention provides methods for forming a bicyclic methylene aziridine by an intramolecular allene aziridination reaction. The substrate can be an allene tethered to an amino (—NH$_2$) group, and the amino group can be separated from the proximal allene carbon by about 3, 4, 5, or 6 atoms linearly. The methods can include combining the allene, a rhodium catalyst, a solvent, and an oxidant, to provide a reaction mixture, thereby initiating an intramolecular allene aziridination reaction, to provide a bicyclic methylene aziridine.

The methods can include contacting the bicyclic methylene aziridine with a nucleophile to provide a nucleophile-addition product, optionally further reacting the nucleophile-addition product with an electrophile to provide an electrophile-addition product. The bicyclic methylene aziridine can also be reacted with an electrophile to provide an electrophile-addition product, and optionally further reacted with a nucleophile.

Any product of a reaction described herein can be further oxidized, reduced (e.g., with a hydride reagent or in the presence of H$_2$ and a metal catalyst), or hydrolyzed to form other useful compounds and intermediates, for example, synthetic motifs containing three contiguous carbon-heteroatom bonds.

The invention also provides methods for reacting a bicyclic methylene aziridine with a nitrene equivalent, such as an N-aminophthalimide, in the presence of an oxidant to provide an N,N-spiroaminal. The N,N-spiroaminal can have, for example, four contiguous carbon-heteroatom bonds in the form of a tricyclic 1,4-diazaspiro[2.2]pentane (DASP). The DASP can be contacted with a nucleophile to provide a bicyclic ring-opened nucleophile-addition product.

The invention further provides methods for forming a bicyclic N,N-aminal in a one pot reaction. The methods can include forming a bicyclic methylene aziridine by an intramolecular allene aziridination reaction as described above, followed by combining the bicyclic methylene aziridine with a nitrene equivalent in the presence of an oxidant to provide an N,N-spiroaminal, such as a tricyclic 1,4-diazaspiro[2.2]pentane (DASP). The N,N-spiroaminal can then be reacted with a nucleophile to provide a bicyclic ring-opened nucleophile-addition product, which can be used to provide other useful products.

The invention also provides novel compounds of the Formulas described herein, and novel compounds prepared by the methods described herein, for example, a compound having three contiguous carbon-heteroatom bonds. The invention further provides compounds of the Formulas described herein that are useful as intermediates for the synthesis of other useful compounds.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention described elsewhere in the specification.

FIG. 3. X-ray crystal structure of DASP 10a.

DETAILED DESCRIPTION

Figure 1:
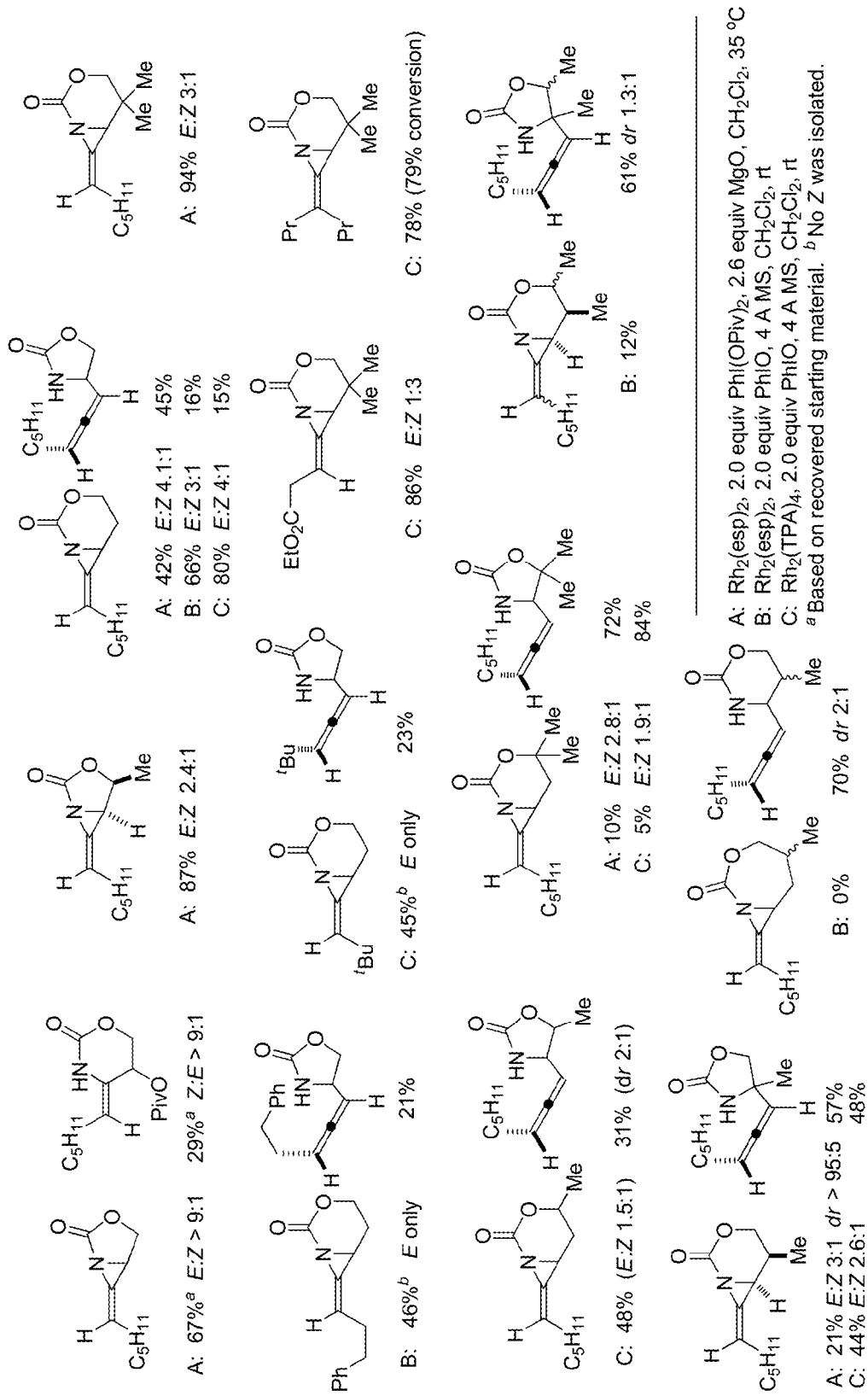
FIG. 1. Examples of carbamate nitrene precursors and products, according to some embodiments.

Asymmetric heteroatom-bearing stereotriads and tetrads can be prepared via allene oxidation by the methods described herein. Functionalization of olefins can efficiently provide two new carbon-heteroatom bonds, for example, by epoxidation, aminohydroxylation, diamination, or aziridination. The useful nature of the reactions when applied to allenes is illustrated by the allene functionalizations generally outlined in Scheme 1 below, where three or four new carbon-heteroatom bonds can be formed by allene oxidation.

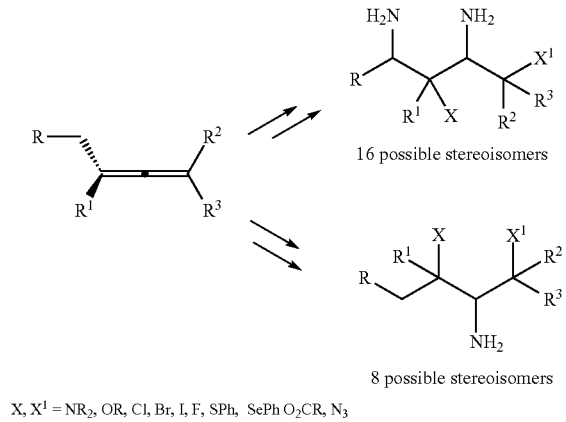

Scheme 1. Allene Functionalization.

$X, X^1$ = $NR_2$, OR, Cl, Br, I, F, SPh, SePh $O_2CR$, $N_3$

The R group can be a variety of alkyl, aryl, heteroalkyl, heteroaryl, or cycloalkyl groups, with a variety of substitutions and heteroatoms replacing various carbons in the groups. Particularly useful examples include allenic carbamates or sulfamates. $R^1$, $R^2$, and $R^3$ can be, for example, as defined for one or more of the Formulas described herein.

Allenic carbamates or sulfamates can be treated with a Rh(II) catalyst in the presence of an oxidant to form a highly strained bicyclic methylene aziridine. This reactive intermediate can be diastereoselectively transformed into a variety of stereotriads using a diverse array of nucleophiles and electrophiles. Examples of useful nucleophiles include amines, carboxylic acids, alcohols, thiols, selenides, azides, halogens, and carbon nucleophiles including malonates, electronic-rich aromatic rings, and $R_2Mg$ where R can be $R^1$ as defined herein below. Examples of useful electrophiles include electrophilic sulfur, peroxyacids, N-halosuccinimides, N-haloamines, and N-aminophthalimides. These new methods thus offer an efficient approach to transferring the axial chirality of an allene to three new carbon-heteroatom bonds and a variety of useful substituents.

Advantages of the methods include the facile preparation of reactants and intermediates from readily accessible allenes, the ability to introduce a wide variety of functionality, the need for only mild reaction conditions, that useful electron-withdrawing groups can be present on the aziridine nitrogen to promote subsequent reactivity, the inherent ring strain in the aziridine that promotes facile ring opening, and a high degree of possible stereocontrol.

Allene Aziridination to Bicyclic Methylene Aziridine Scaffolds

The invention thus provides a method comprising forming a bicyclic methylene aziridine by an intramolecular allene aziridination reaction. An allene group can be tethered to an amino ($-NH_2$) group, and the amino group can be separated from the proximal allene carbon by 3, 4, 5, or 6 atoms linearly. The aziridine nitrogen of the bicyclic methylene aziridine can be substituted by an electron-withdrawing group, such as a carbamate or sulphone. The allene can be mono-substituted, di-substituted, tri-substituted, or tetra-substituted. The allene can be, for example, a compound of Formula I:

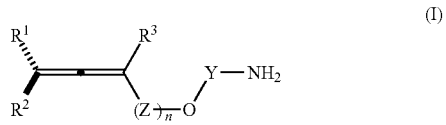

(I)

wherein $R^1$, $R^2$, and $R^3$ are each independently H, alkyl, cycloalkyl, aryl, heteroaryl, heterocycle, (alkyl)cycloalkyl, (alkyl)aryl, (alkyl)heteroaryl, or (alkyl)heterocycle;

n is 1, 2, or 3;

Y is $-C(=O)-$ or $-S(=O)_2-$; and each Z is independently $-(CH_2)-$, $-(CHR^1)-$, or $-(C(R^1)_2)-$.

The method can include combining the allene, a rhodium catalyst, a solvent, and an oxidant, to provide a reaction mixture, thereby initiating an intramolecular allene aziridination reaction, to provide a bicyclic methylene aziridine. The rhodium catalyst can be any Rh(II) catalyst that is effective to promote the intramolecular allene aziridination. In some embodiments, the reaction proceeds in at least 30% yield, at least 40% yield, at least 50% yield, at least 60% yield, at least 70% yield, or at least 80% yield. In some embodiments, the rhodium catalyst is $Rh_2(esp)_2$ where esp is α,α,α',α'-tetramethyl-1,3-benzenedipropionate, or $Rh_2(TPA)_4$ where TPA is triphenylacetate. Other suitable rhodium catalysts include dimeric rhodium catalysts with bulky ester-based or amide-based ligands, although strongly electron-withdrawing esters are not suitable in some embodiments.

The oxidant can be, for example, any suitable and effective hypervalent iodide oxidant. Examples include, but are not limited to, PhIO, PhI(OAc)$_2$, PhI(OPiv)$_2$, or PhI(CN)OTf. One-electron oxidants such as cerium(III) sulfate or lead(IV) acetate may also be employed. Oxidation may also be carried out using standard electrochemical methods.

The reaction mixture can also include a drying agent, such as molecular sieves (e.g., 3A or 4A), for example, when PhIO is used as the oxidant, to adsorb or absorb water generated in the reaction Alkaline earth metal oxides, such as magnesium oxide, can be used to neutralize acetic acid or pivalic acid generated when PhI(OAc)$_2$ or PhI(OPiv)$_2$ are used as the oxidants. The solvent can be any suitable solvent or combination of solvents that provide sufficient solubility of the allene reactant and the reagents to enable the reaction to proceed. Examples of potential solvents include acetone, methylene chloride, dichloroethane, chloroform, isopropyl acetate, benzene, toluene, xylenes, acetonitrile, ether, tetrahydrofuran, and combinations thereof. One skilled in the art will be able to readily determine which solvents are suitable and effective based on solubility of reactants and reagents, and the efficiency of the reaction. The reactions can be typically run at room temperature (~23° C.). Some reactions, however, may benefit from initially reduced temperatures such as about −30° C. or about 0° C. Other reactions can be enhanced by elevated temperatures, such as about 30° C., about 35° C., about 40° C., about 50° C., about 70° C., about 90° C., about 100° C., or about 110° C.

Figure 2:
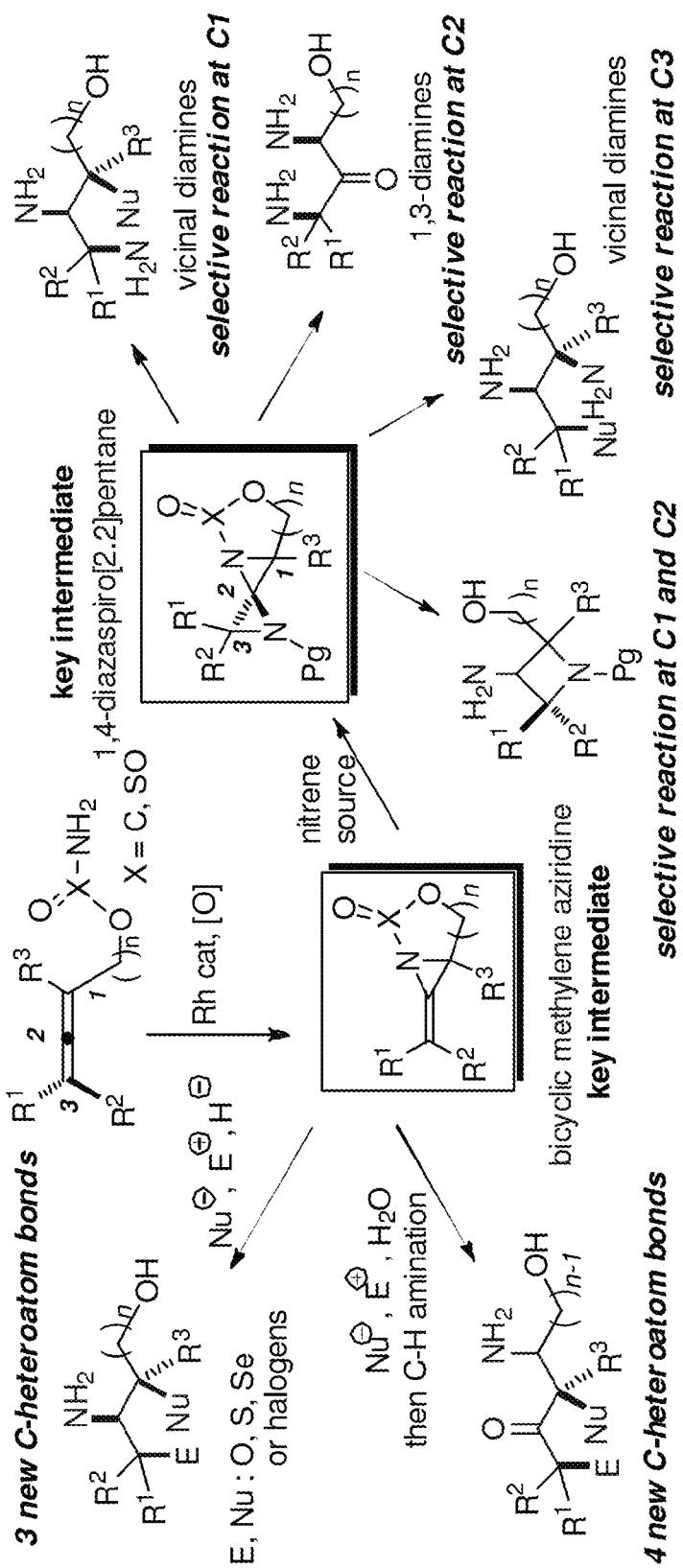
FIG. 2. Allene oxidation methods to form stereotriads and tetrads. The reactions provide access to multiple stereoisomers containing the same substitution pattern resulting in varied product topologies. The reactions illustrate the translation of axial chirality to three new carbon-heteroatom bonds. The variables $R^1$, $R^2$, and $R^3$ are as defined for Formula I herein. Nu⁻, E⁺, and H⁻ are any suitable nucleophile, electrophile, or hydride source, for example, as described herein. Pg is a nitrogen protecting group.

An example of the intramolecular aziridination is shown below in Scheme 2, where each R is independently an alkyl or aryl group, Nu⁻ is a nucleophile as described herein, E⁺ is an electrophile as described herein, H⁻ is a hydride reagent, and $R^1M$ is an organometallic reagent such as a Grignard reagent, an alkyl lithium reagent, or an alkylcuprate. The bicyclic methylene aziridine can then be allowed to react with a nucleophile to provide a nucleophile-addition product such as an enesulphone or an enecarbamate (as illustrated in Scheme 2). Alternatively, the bicyclic methylene aziridine can be allowed to react with an electrophile such as an epoxide, an N-halo-succinimide, or a nitrene equivalent. Additional reactions that can be carried out on bicyclic methylene aziridines are shown in FIG. 2.

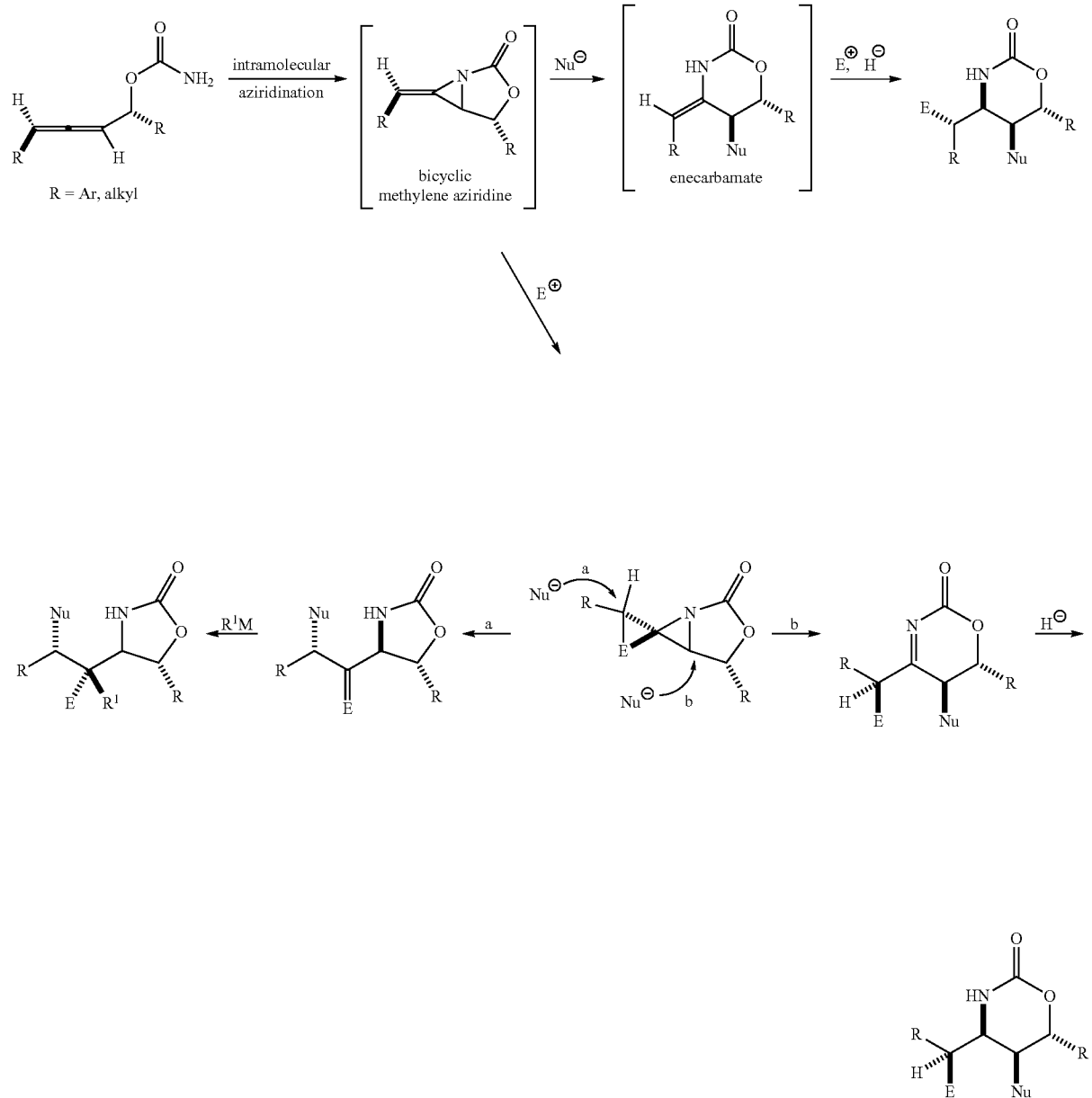

A nucleophile for addition to the bicyclic methylene aziridine can be, for example, a carboxylic acid or a carboxylate anion, a halide, an alcohol in the presence of an acid such as a Lewis acid, a thiol in the presence of a Lewis acid, a cyanide, a nitrile, an alkoxide, an azide, a selenium nucleophile such as benzeneselenol, and the like. In some embodiments, the carboxylic acid can be an optionally substituted ($C_2$-$C_{24}$)carboxylic acid; the halide can be and alkali metal halide or $R'_3SiCl$ where each $R'$ is independently alkyl, aryl, alkoxy, or aryloxy; the alcohol can be a ($C_1$-$C_{24}$)alcohol; the thiol can be an alkylthiol or an arylthiol; the cyanide can be an alkali metal cyanide; and the azide can be an alkali metal azide. The acid can be any suitable and effective acid, such as a Lewis acid, a mineral acid, or an organic acid. The Lewis acid can be, for example, $Sc(OTf)_3$, $Bi(OTf)_3$, $BF_3 \cdot OEt_2$, $TiCl_4$, $Ti(OiPr)_4$, $InCl_3$, $In(OTf)_3$, or a lanthanide triflate. Brønsted acids may also promote the reaction, including phosphoric acids, carboxylic acids (e.g., AcOH, BzOH), p-toluenesulfonic acid, MsOH, other sulfonic acids, and the like.

As discussed above, the bicyclic methylene aziridine can be an enecarbonate or an enesulphone. In one embodiment, the bicyclic methylene aziridine is a compound of Formula II:

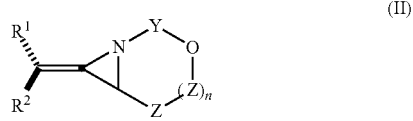

wherein
$R^1$ and $R^2$ are each independently H, alkyl, cycloalkyl, aryl, heteroaryl, heterocycle, (alkyl)cycloalkyl, (alkyl)aryl, (alkyl)heteroaryl, or (alkyl)heterocycle;
n is 0, 1, or 2;
Y is —C(=O)— or —S(=O)$_2$—; and
each Z is independently —(CH$_2$)—, —(CHR$^1$)—, or —(C(R$^1$)$_2$)—.

In various embodiments, the bicyclic methylene aziridine can be a bicyclic methylene aziridine illustrated in FIG. 1, or a derivative thereof.

A nucleophile-addition product can be, for example, a compound of Formula III:

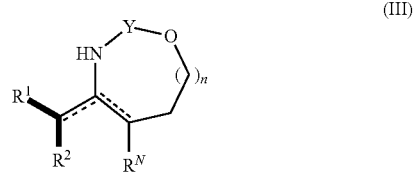

wherein $R^1$ and $R^2$ are each independently H, alkyl, cycloalkyl, aryl, heteroaryl, heterocycle, (alkyl)cycloalkyl, (alkyl)aryl, (alkyl)heteroaryl, (alkyl)heterocycle, or azide;
n is 0 or 1;
the dotted lines represent optional double bonds where only one of the double bonds is present;
Y is —C(=O)— or —S(=O)$_2$—; and
$R^N$ is acetoxy, chloroacetoxy, halo, cyano, alkoxy, thioalkyl, or thioaryl.

As shown in Scheme 2, a variety of further reactions can be carried out on the nucleophile-addition product. Such reactions include hydrolysis of acyloxy groups such as acetoxy groups or chloroacetoxy groups, to provide a hydroxyl substituent.

Suitable electrophiles for addition to the bicyclic methylene aziridines or their nucleophile-addition products include N-halosuccinimides and hydrides. The electrophile-addition products can then be reduced to provide synthetic motifs containing three contiguous carbon-heteroatom bonds. Alternatively, the bicyclic methylene aziridine or the nucleophile-addition product can be reacted with a nitrene equivalent, such as an N-aminophthalimide, in the presence of an oxidant to provide an N,N-spiroaminal, as shown below in Scheme 3.

Scheme 3. Allene Aziridination to DASP Scaffolds.

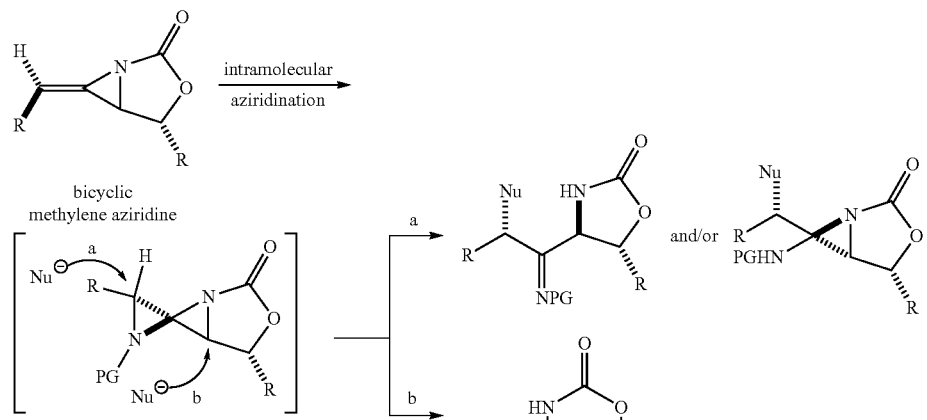

Intermolecular aziridation nitrene equivalents: RONH$_2$; ArONH$_2$; ArSO$_2$NH$_2$;

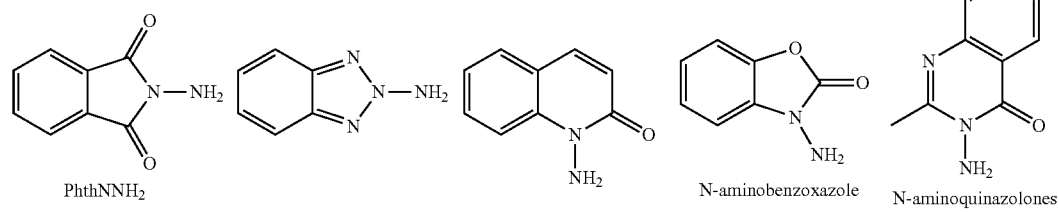

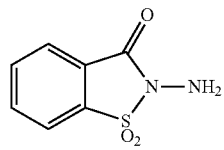

Nitrene sources for intermolecular aziridination include N-aminobenzoxazole, N-aminoquinazolones, $RONH_2$ where R is alkyl as described herein, and $ArONH_2$ or $ArSO_2NH_2$ where Ar is aryl as described herein. Further examples of nitrene equivalents are described by Anderson et al., *J. Chem. Soc.* (C), 1970, 576-582; Atkinson, et al., *Chem. Soc., Perkin I*, 1984, 1905-1912; and Atkinson, et al., *J. Chem. Soc., Chem. Comm.*, 1981, 160-162.

The N,N-spiroaminal can have four contiguous carbon-heteroatom bonds in the form of a tricyclic 1,4-diazaspiro [2.2]pentane (DASP). The DASP and a nucleophile can be combined to provide a bicyclic ring-opened nucleophile-addition product. Suitable examples of nucleophiles are discussed above. The products can then be subjected to further reaction conditions, including but not limited to oxidation, reduction (e.g., with a hydride reagent or in the presence of $H_2$ and a metal catalyst), or hydrolysis, to form other useful compounds and intermediates.

The invention further provides a method for forming a bicyclic an N,N-aminal in a one-pot reaction. The method can include forming a bicyclic methylene aziridine by an intramolecular allene aziridination reaction as discussed above. The bicyclic methylene aziridine can then be contacted with a nitrene source, such as a nitrene equivalent described above (e.g., N-aminophthalimide), in the presence of an oxidant to provide an N,N-spiroaminal. The N,N-spiroaminal can then be contacted with a nucleophile to provide a bicyclic ring opened nucleophile-addition product, all in one pot without any work-up between steps.

Reactions of Bicyclic MAs to Stereotriads

The scope of the reactions of methylene aziridines, enecarbamates, and enesuphones is further illustrated below in Schemes 4 and 5.

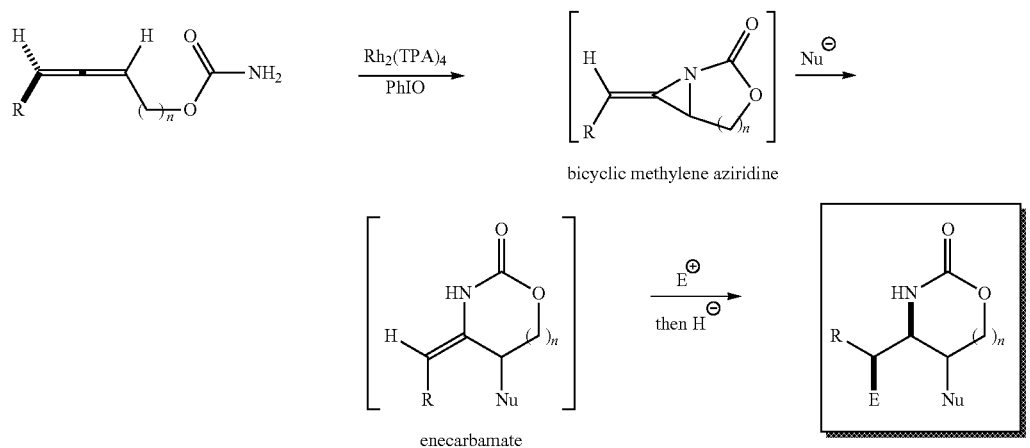

Scheme 4
Reactions of Enecarbamates.

| substrate | E⊕ | Nu | product | yield | dr |
|---|---|---|---|---|---|
| | NBS | NaCNBH₃ | (7-membered cyclic carbamate with C₅H₁₁, Br, OAc substituents) | 73% | 10:1 |
| | NIS | none | (7-membered cyclic carbamate with C₅H₁₁, OAc, exocyclic alkene) | 100% by NMR | E:Z 1:5 |
| | Selectfluor [F-N⊕(CH₂Cl)N⊕ (BF₄)₂] | none | H₁₁C₅–C(=O)–CHF–...–CH(OAc)–CH₂CH₂–O–C(=O)–NH₂ | 58% | 2:1 |
| | Ph–S(=NTs)–N(Ts)–SPh | NaCNBH₃ | (7-membered cyclic carbamate with C₅H₁₁, PhS, OAc substituents) | 57%* | >10:1 |
| (7-membered cyclic carbamate starting material with C₅H₁₁, AcO, exocyclic =CH) | NBS | NaCNBH₃ | (two diastereomeric products, each with C₅H₁₁, Br, OAc) | 82% | 1.1:1 |

*Based on recovered starting material.

Scheme 5
Reactions of Enesulfamates.

| substrate | E⊕ | Nu | product | yield | dr |
|---|---|---|---|---|---|
| (enesulfamate with AcO, H₁₁C₅) | NBS | H—≡—MgBr | (product with HO-alkyne, Br, OAc) | 59% | >10:1 |
| | NBS | NaCNBH₃ | (product with Br, OAc) | 65% | >5:1 |
| | NBS | MeMgBr | (product with Me, Br, OAc) | 49% | 2.8:1 |
| (enesulfamate with OMe, H₁₁C₅) | NBS | NaCNBH₃ | (product with Br, OMe) | 53% | >10:1 |
| (allene substrate with C₅H₁₁, NH₂, cat Rh₂(TPA)₄, PhIO) | AcOH then NBS | NaCNBH₃ | (product with Br, OAc) | 43% | >10:1 |
| | MeOH then NBS | NaCNBH₃ | (product with Br, OMe) | 43% | >10:1 |

For a typical reaction, the E configuration controls dr better than Z configuration. Also, a stronger reductants can help prevent hydrolysis of the intermediate iminium ion. Finally, the scope of nucleophiles that open the sulfamate-based MA include alcohols, halides, carboxylic acids, thiols and amines.

1,4-Diazaspiro[2.2]-pentanes (DASPs)

Examples of substrates and DASP products are further illustrated below in Scheme 6.

Reactions on DASP compounds are further illustrated below in Schemes 7-10.

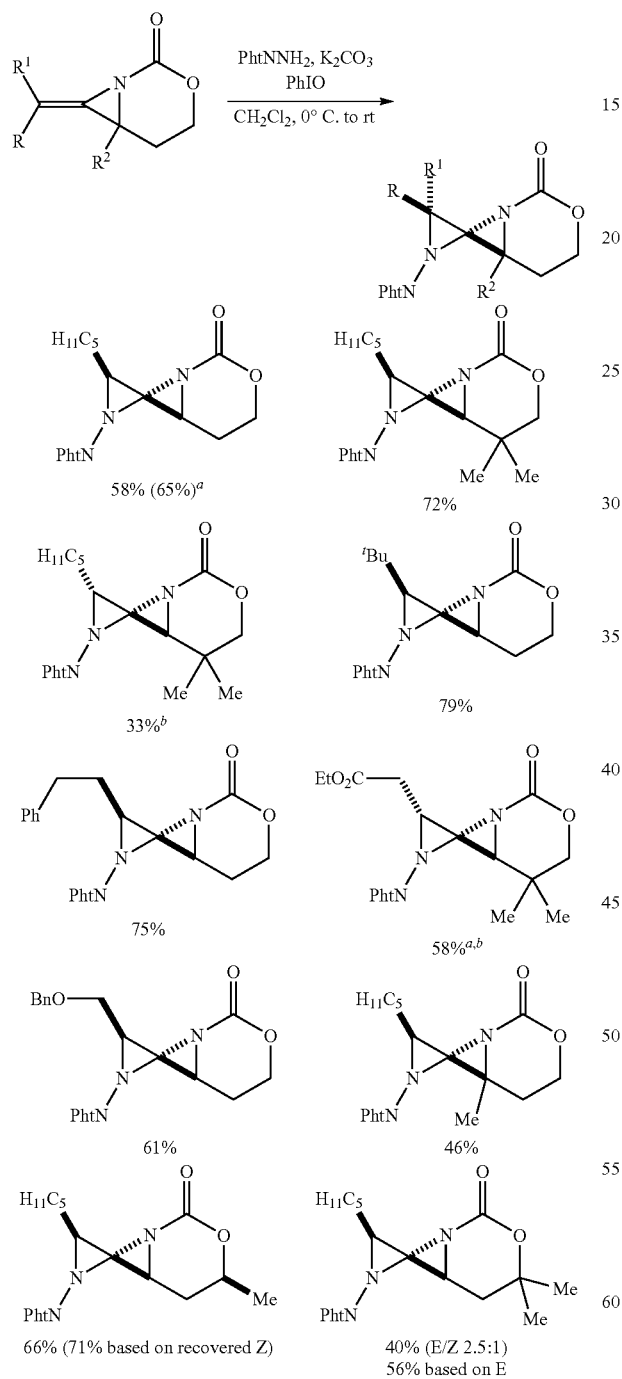

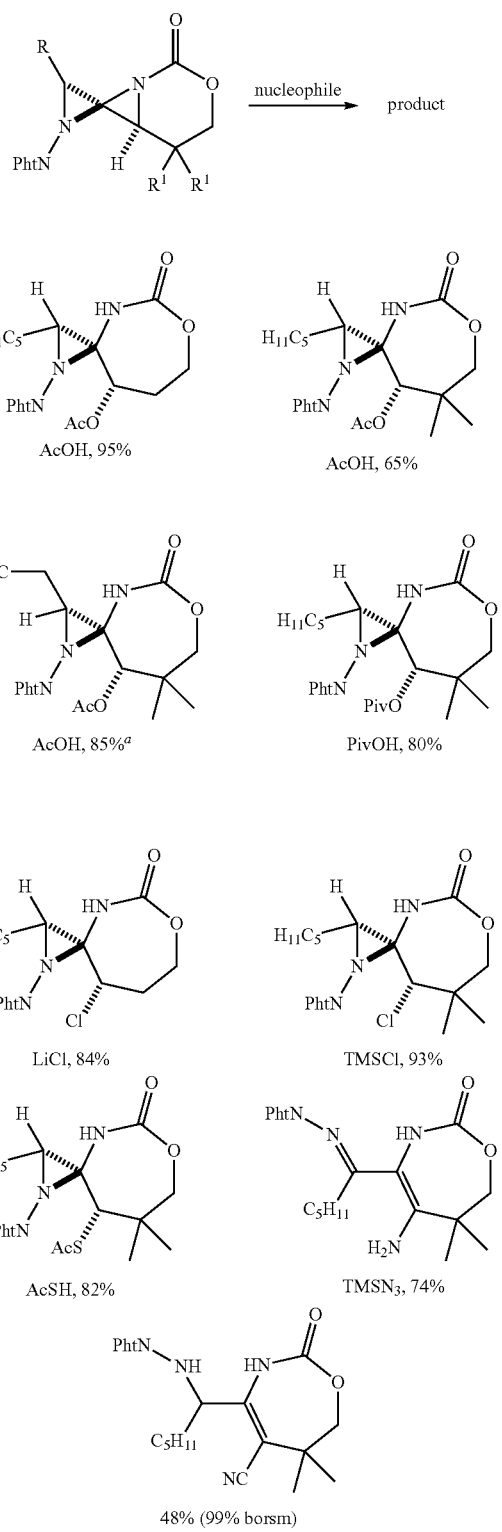

[a] Yield based on recovered starting material.
[b] The starting material was the Z methylene aziridine.

[a] The substrate was the DASP generated from aziridination of the Z methylene aziridine.

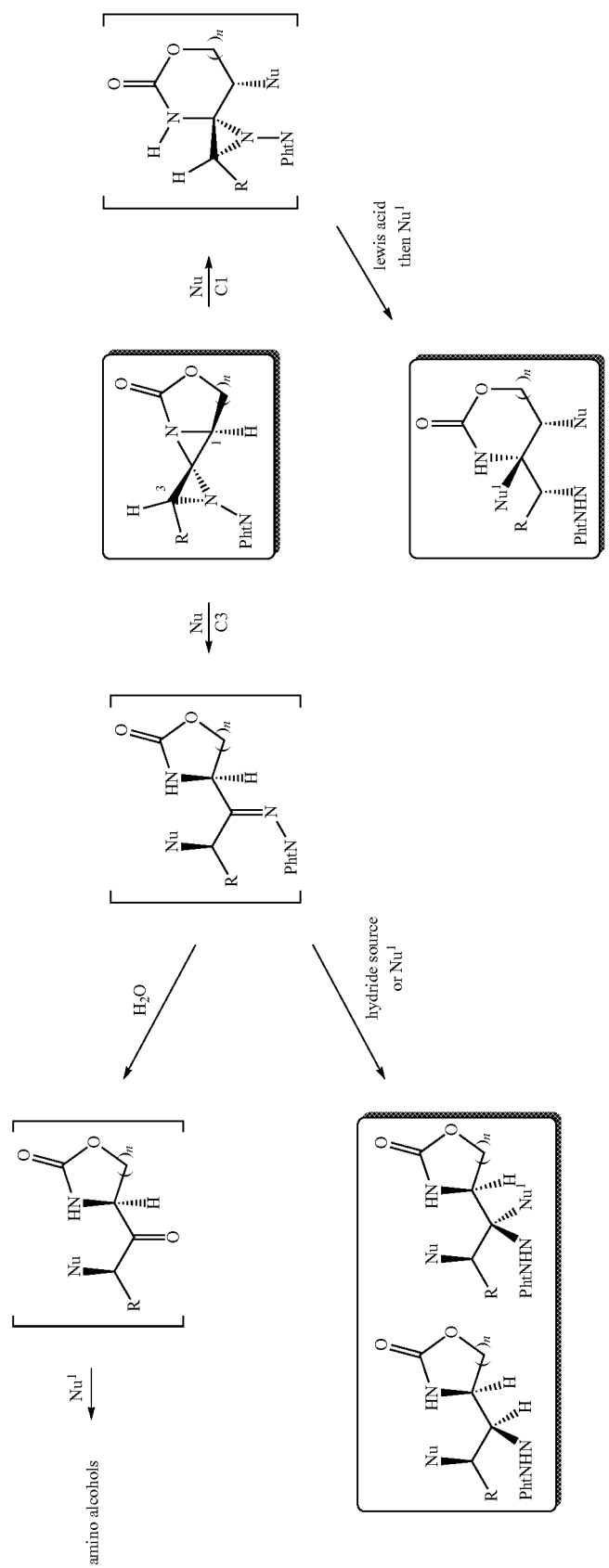
Scheme 8. Reactions of DASPs to Vicinal Diamines.

Other methods to access highly substituted vicinal diamines are limited in number and flexibility. The use of sulfamate nitrene precursors expands the scope of nucleophiles for regioselective DASP ring-opening. Stereocontrol of the reduction of the intermediate imine/iminium may be controlled using chiral reducing agents.

Scheme 9. Reaction of DASPs to 1,3-Diamines.

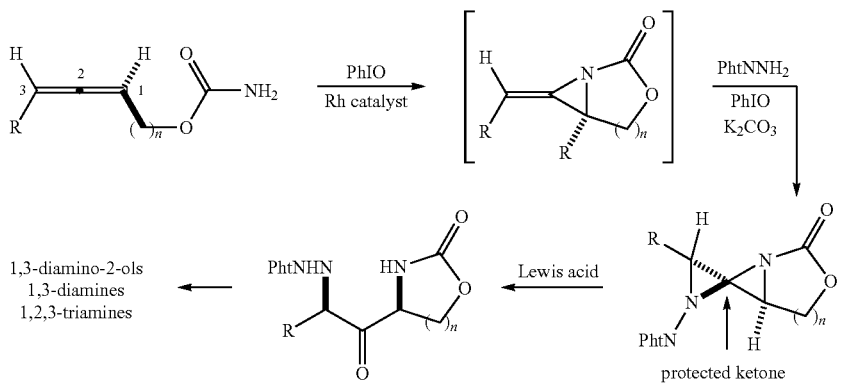

DASPs can be thought of as aminal-protected ketone. Formal hydrolysis of this "ketone" yields 1,3-diamines with good stereocontrol.

Scheme 10. Preparation of 1,3-Diamines from DASPs.

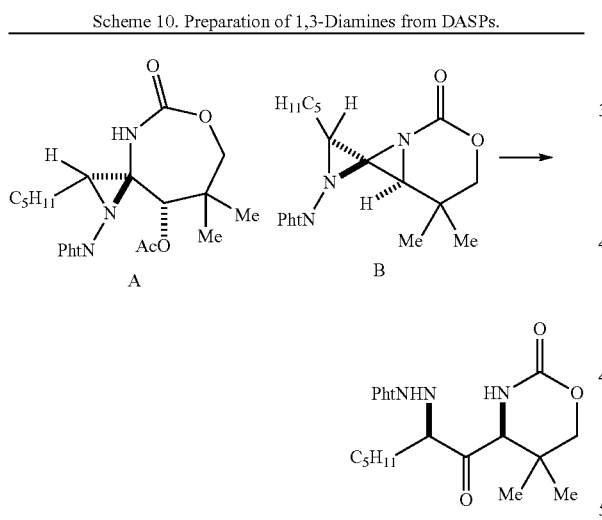

| entry | substrate | additives (equiv) | conversion |
|---|---|---|---|
| 1 | A | CeCl$_3$·7H$_2$O (1) | 0% |
| 2 | | NiCl$_2$·6H$_2$O (1) | 0% |
| 3 | | Ti(O$^i$Pr)$_4$ (1) | 0% |
| 4 | | ZnCl$_2$ (1) | 0% |
| 5 | | Cu(OTf)$_2$ (1) | <50% |
| 6 | | InCl$_3$ (1) | <50% |
| 7 | | Sc(OTf)$_3$ (1) | mixture |
| 8 | | BF$_3$OEt$_2$ (1) | 100% |
| 9 | | TsOH (1) | 100% |
| 10 | | Bi(OTf)$_3$ (1) | 96%$^a$ |
| 11 | | Bi(OTf)$_3$ (0.2) | 100% |
| 12 | | Bi(OTf)$_3$ (0.05) | 100% |
| 13 | B | AcOH, then Bi(OTf)$_3$ (0.05)$^b$ | 100% |
| 14 | | ClCH$_2$CO$_2$H, then Bi(OTf)$_3$ (0.05) | 0%$^c$ |

-continued

Scheme 10. Preparation of 1,3-Diamines from DASPs.

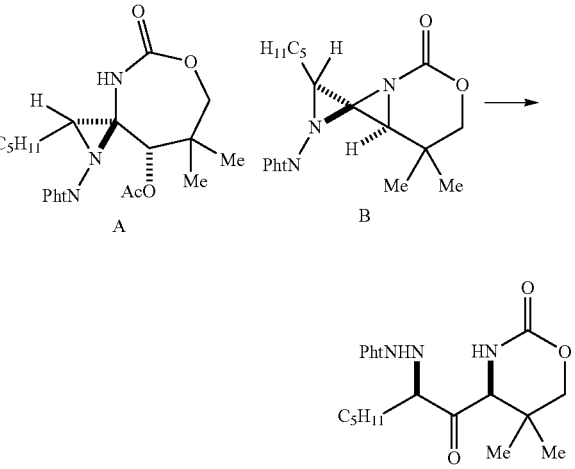

| entry | substrate | additives (equiv) | conversion |
|---|---|---|---|
| 15 | | AcOH at 35° C., then Bi(OTf)$_3$ (0.05) | 100%$^d$ (88%)$^a$ |

$^a$Isolated yield.
$^b$40 h reaction time.
$^c$The product was the ring-opened DASP.
$^d$12 h reaction time.

The 1,3-diamines derived from the DASPs can be obtained in high yield and diastereoselectivity (dr>10:1 in all cases). Preliminary results show that stereocontrolled reduction of the ketone, such as those illustrated in Scheme 11 below, can be achieved.

Scheme 11. Diastereoselectivity of 1,3-Diamines from DASPs.
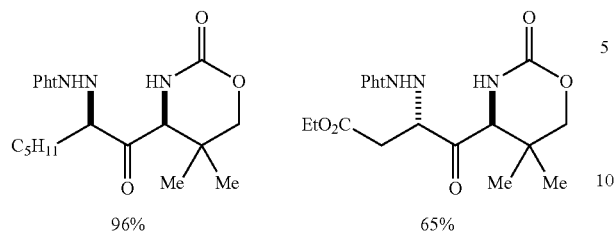
96%   65%
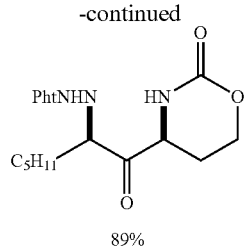
89%
A specific example of the synthesis of a 1,3-diaminoketone is shown in Scheme 12.
Scheme 12. 1,3-Diaminoketone Synthesis.
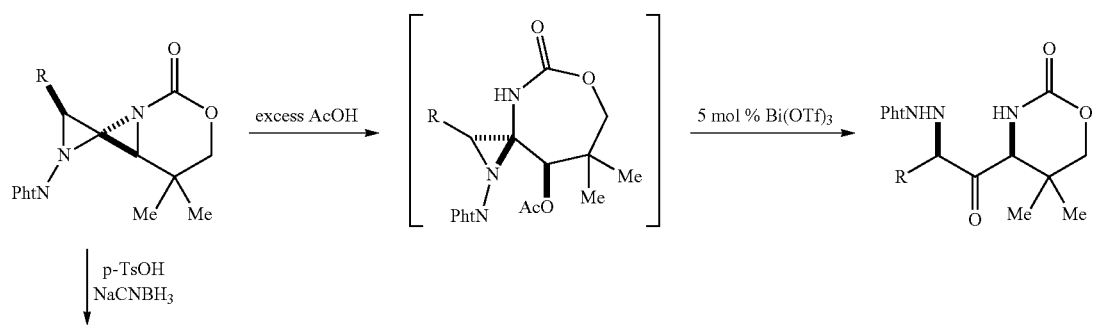
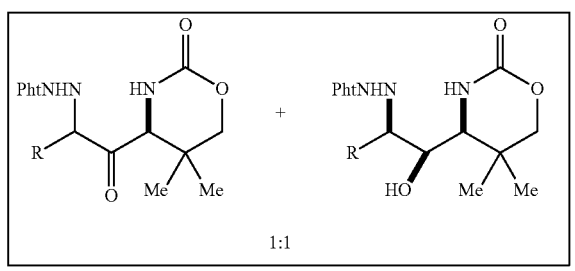
1:1
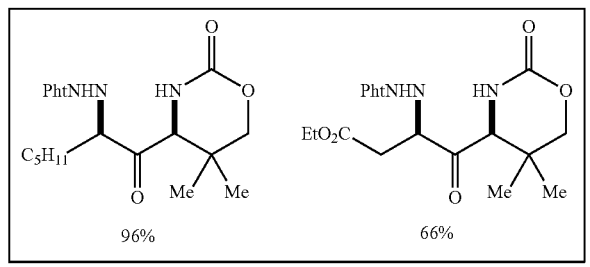
96%   66%

An example of a one-pot DASP formation reaction is illustrated in Scheme 13.

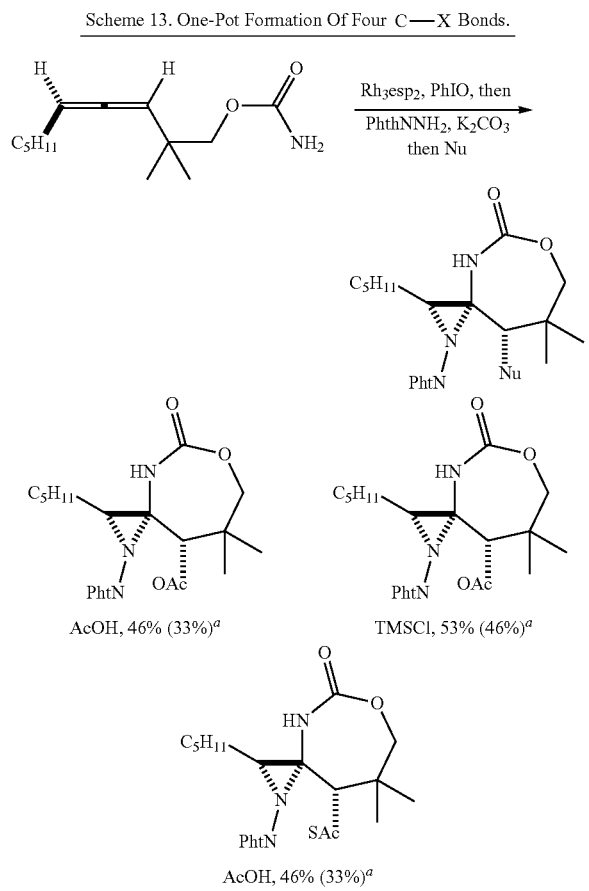

Scheme 13. One-Pot Formation Of Four C—X Bonds.

[a] Overall yield of the three individual steps.

General Synthetic Methods

The invention provides various compounds and synthetic intermediates as described herein. The compounds can be prepared by any of the applicable techniques described herein and they can be modified by a variety of organic synthesis techniques to provide various substituted analogs and derivatives. Many such techniques are well known in the art. However, relevant techniques and transformations are also elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as *March's Advanced Organic Chemistry: Reactions, Mechanisms, and Structure*, 5$^{th}$ Ed. by M. B. Smith and J. March (John Wiley & Sons, New York, 2001); *Comprehensive Organic Synthesis, Selectivity, Strategy & Efficiency in Modern Organic Chemistry, in 9 Volumes*, Barry M. Trost, Editor-in-Chief (Pergamon Press, New York, 1993 printing); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

Definitions

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The allene starting materials can include various carbon chains and ring structures, optionally substituted with one or more substituents. Examples of many suitable chains and ring structures that can be substituents on allenes and their substituents are described below.

The terms "halogen" and "halo", and "halide" refer to fluoro, chloro, bromo, and iodo groups, typically used as organic substrate substituents.

The term "alkyl" refers to a branched or unbranched carbon chain having, for example, about 1-20 carbon atoms, and often 1-12, 1-10, 1-8, 1-6, or 1-4 carbons. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, as described in the definition of the term "substituted" below.

The alkyl can also be optionally partially or fully unsaturated in certain embodiments. As such, the recitation of an alkyl group optionally includes both alkenyl and alkynyl groups. The alkyl can be a monovalent hydrocarbon radical, as described and exemplified above, or it can be a divalent hydrocarbon radical (i.e., an alkylene), for example, that links to other groups. In some embodiments, certain alkyl groups can be excluded from a definition. For example, in some embodiments, methyl, ethyl, propyl, butyl, or a combination thereof, can be excluded from a specific definition of alkyl in an embodiment.

The term "alkoxy" refers to the groups alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

The term "alkenyl" refers to a monoradical branched or unbranched partially unsaturated hydrocarbon chain (i.e. a carbon-carbon, $sp^2$ double bond) preferably having from 2 to 10 carbon atoms, about 2 to 6 carbon atoms, or about 2 to 4 carbon atoms. Examples include, but are not limited to, ethylene or vinyl, allyl, cyclopentenyl, and 5-hexenyl. An alkenyl can be unsubstituted or substituted.

The term "alkynyl" refers to a monoradical branched or unbranched hydrocarbon chain, having a point of complete unsaturation (i.e. a carbon-carbon, sp triple bond), typically having from 2 to 10 carbon atoms, about 2 to 6 carbon atoms, or about 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, and the like. An alkynyl can be unsubstituted or substituted.

An "alkylene" refers to a saturated, branched or straight chain hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like. An alkylene can be unsubstituted or substituted.

The term "cycloalkyl" refers to cyclic alkyl groups of, for example, 3 to about 12, 3 to about 10, 3 to about 8, about 4 to about 8, or 5-6, carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

As used herein, "aryl" refers to an aromatic hydrocarbon group derived from the removal of one hydrogen atom from a single carbon atom of a parent aromatic ring system. The radical attachment site can be at a saturated or unsaturated carbon atom of the parent ring system. The aryl group can have from 6 to about 20 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "heteroaryl" refers to a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described in the definition of "substituted". Typical heteroaryl groups contain 2-20 carbon atoms in addition to the one or more hetoeroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or —($C_1$-$C_6$) alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, silicon, and sulfur, and optionally substituted with one or more groups as defined for the term "substituted". A heterocycle can be a monocyclic, bicyclic, or tricyclic group. A heterocycle group also can contain an oxo group (═O) or a thioxo (═S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholinyl, piperazinyl, piperidinyl, pyrazolidinyl, pyrazolinyl, pyrrolidine, pyrroline, quinuclidine, tetrahydrofuranyl, and thiomorpholine, where the point of attachment can be at any atom accessible by known synthetic methods.

When an aryl, heteroaryl, heterocycle, or cycloalkyl group is a substituent, the group can be linked to the substrate via an alkylene group, thereby providing (alkyl)aryl, (alkyl)heteroaryl, (alkyl)heterocycle, or (alkyl)cycloalkyl substituents.

The terms "acyl" and "alkanoyl" refer to groups of the formula —C(═O)R, where R is an alkyl group as previously defined. The term "aroyl" refers to groups of the formula —C(═O)Ar, where Ar is an aryl group as previously defined.

The term "alkoxycarbonyl" refers to groups of the formula —C(═O)OR, where R is an alkyl group as previously defined.

The term "acyloxy" refers to groups of the formula —O—C(═O)R, where R is an alkyl group as previously defined. Examples of acyloxy groups include acetoxy and propanyloxy.

The term "amino" refers to —$NH_2$, and the term "alkylamino" refers to —$NR_2$, wherein at least one R is alkyl and the second R is alkyl or hydrogen. The term "acylamino" refers to RC(═O)NH—, wherein R is alkyl or aryl.

The term "protecting group" or "PG" refers to group that, when bound to a functional group, prevents undesired reactions from occurring at the functional group and that can be removed by conventional chemical or enzymatic steps to reestablish the original functional group. The particular removable protecting group employed is usually not critical. Suitable protecting groups for various situations are well known to those skilled in the art. A large number of protecting groups and corresponding chemical cleavage reactions are described in *Protective Groups in Organic Synthesis*, Theodora W. Greene (John Wiley & Sons, Inc., New York, 1991, ISBN 0-471-62301-6); and Kocienski, Philip J., *Protecting Groups* (Georg Thieme Verlag Stuttgart, New York, 1994); and the references cited therein. Removable protecting groups include conventional groups such as allyl, benzyl, acetyl, chloroacetyl, thiobenzyl, benzylidine, phenacyl, methyl methoxy, silyl ethers (e.g., trimethylsilyl (TMS), t-butyl-diphenylsilyl (TBDPS), or t-butyldimethylsilyl (TBS)), esters including sulfonic acid esters, carbonates, sulfates, and sulfonates, carbamates, and the like, or any other group that can be introduced chemically onto a functionality and later selectively removed either by chemical or enzymatic methods in mild conditions compatible with the nature of the product.

The term "substituted" indicates that one or more hydrogen atoms on the group indicated in the expression using "substituted" is replaced with a "substituent". The number referred to by 'one or more' can be apparent from the moiety one which the substituents reside. For example, one or more can refer to, e.g., 1, 2, 3, 4, 5, or 6; in some embodiments 1, 2, or 3; and in other embodiments 1 or 2. The substituent can be one of a selection of indicated groups, or it can be a suitable group known to those of skill in the art, provided that the substituted atom's normal valency is not exceeded, and that the substitution results in a stable compound. Suitable substituent groups can be included on substrates described herein, such as the various heavy atom chains and ring structures, include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano. Additionally, suitable substituent groups can be, e.g., —X, —R, —B(OH)$_2$, —B(OR)$_2$, —O$^-$, —OR, —SR, —S$^-$, —NR$_2$, —NR$_3$, ═NR, —CX$_3$, —CN, —OCN, —SCN, —N═C═O, —NCS, —NO, —NO$_2$, ═N$_2$, —N$_3$, —NC(═O)R, —C(═O)R, —C(═O)NRR, —S(═O)$_2$O$^-$, —S(═O)$_2$OH, —S(═O)$_2$R, —OS(═O)$_2$OR, —S(═O)$_2$NR, —S(═O)R, —OP(═O)O$_2$RR, —P(═O)O$_2$RR, —P(═O)(O$^-$)$_2$, —P(═O)(OH)$_2$, —C(═O)R, —C(═O)X, —C(S)R, —C(O)OR, —C(O)O$^-$, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (═O) or thioxo (═S), or the like, then two hydrogen atoms on the substituted atom are replaced. In some embodiments, one or more of the substituents above are excluded from the group of potential values for substituents on the substituted group, or on a compound defined by a formula describing a group of compounds. Additionally, ions or radicals of the substituents recited above can be nucleophiles or electrophiles that can be used in a reaction described herein, to provide various reaction products.

Substituted alkyl groups include, for example, haloalkyl groups. The term "haloalkyl" refers to alkyl as defined herein substituted by 1-4 halo groups, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, perfluorooctyl, and the like.

As to any of the above groups, which contain one or more substituents, it is understood, of course, that such groups do not contain any substitution or substitution patterns that are sterically impractical and/or are synthetically non-feasible. The substrates described herein may contain asymmetrically substituted carbon atoms, and may be isolated in optically active or racemic forms. All chiral, diastereomeric, racemic forms and all geometric isomeric forms of a structure are part of this invention.

The term "contacting" refers to the act of touching, making contact, or of bringing to immediate or close proximity, including at the cellular or molecular level, for example, to bring about a physiological reaction, a chemical reaction, or a physical change, e.g., in a solution or in a reaction mixture.

An "effective amount" refers to an amount effective to bring about a recited effect. For example, an amount effective can be an amount effective to initiate a reaction and to provide a discernable amount of products. Determination of an effective amount is well within the capacity of persons skilled in the art. The term "effective amount" is intended to include an amount of a compound described herein, or an amount of a combination of compounds described herein, e.g., that is effective to initiate a reaction described herein. For example, the reactions described herein can include an effective amount of catalyst, i.e., an amount necessary to facilitate a reaction. Likewise, the reactions can include an effective amount of a solvent, i.e., an amount of solvent necessary to dissolve the reactants and reagents to a sufficient extent to facilitate a reaction. Thus, an "effective amount" generally means an amount that provides the desired outcome.

An "allene" group refers to three contiguous carbon atoms linked together by two carbon-carbon double bonds. An allene can be mono-substituted, di-substituted, tri-substituted, or tetrasubstituted. A proximal allene carbon refers to the carbon of the allene group that is closest to another reference group, with respect to the shortest number of atoms in a chain linking the reference group to the allene carbon.

A "nucleophile-addition product" refers to the product of a reaction in which a nucleophile has been added to a substrate.

An "electrophile-addition product" refers to the product of a reaction in which an electrophile has been added to a substrate.

A "one-pot reaction" refers to a reaction that is carried out in one reaction vessel without working up the reactants and products in between steps of the overall reaction. Such steps can include aziridinations, oxidations, reductions, hydrolyses, and combinations thereof.

The term "enantiomerically enriched" refers to mixtures that have one enantiomer present to a greater extent than another. The term "enantiomerically enriched" can refer to a mixture having at least about 50% enantiomeric excess ("ee"). The term can also refer to a mixture having at least about 75% ee; at least about 80% ee; at least about 85% ee; i at least about 90% ee; at least about 92% ee; at least about 95% ee; at least about 98% ee; or at least about 99% ee. As would be readily recognized by one of skill in the art, the compounds described herein can be prepared in enantiomerically enriched form. Likewise, the compounds described herein can be prepared in diastereomerically enriched form, and thus can have a diastereomeric excess in percentages similar to those recited above for an enantiomeric excess, wherein the diastereomeric excess is typically defined as a diastereomeric ratio ("dr").

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Allene Functionalization Via Bicyclic Methylene Aziridines

This example describes the use of bicyclic methylene aziridines (MAs) as scaffolds for the functionalization of each of the three carbons of an allene (Scheme 1-A). The reactions described herein thus allow for the transformation of allenes into synthetic motifs containing three contiguous carbon-heteroatom bonds. The bicyclic methylene aziridines (MAs) can be prepared via intramolecular allene aziridination, as described herein.

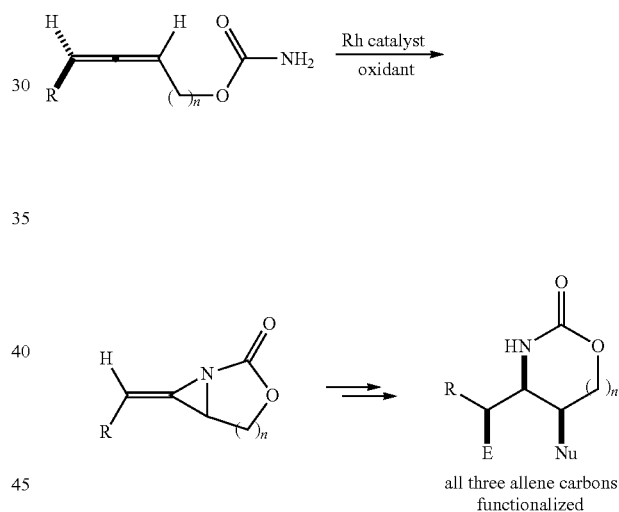

Scheme 1-A. Allene functionalization into useful synthetic motifs.

Olefins are popular substrates for a host of oxidative transformations designed to introduce new C—N bonds into molecules. However, considerably less effort has been devoted to oxidations of allenes, despite the potential to efficiently generate three new contiguous heteroatom-bearing chiral centers. This example describes the use of intramolecular allene amination as a key step for the stereoselective and flexible functionalization of allenes (Atkinson and Malpass, *Tetrahedron Lett.* 1975, 4305; Bingham and Gilbert, *J. Org. Chem.* 1975, 40, 224).

One approach toward this goal is illustrated below in Scheme 1-1. Reaction of an intermediate bicyclic methylene aziridine (MA) 2 with a nucleophile would generate enecarbamate 3. Sequential addition of an electrophile and a hydride source to reduce the resultant imine could flexibly generate motifs such as 4 (Robertson et al., *Org. Biomol. Chem.* 2010, 8, 3060; Shipman, *Synlett.* 2006, 3205).

Scheme 1-1. Allene functionalization

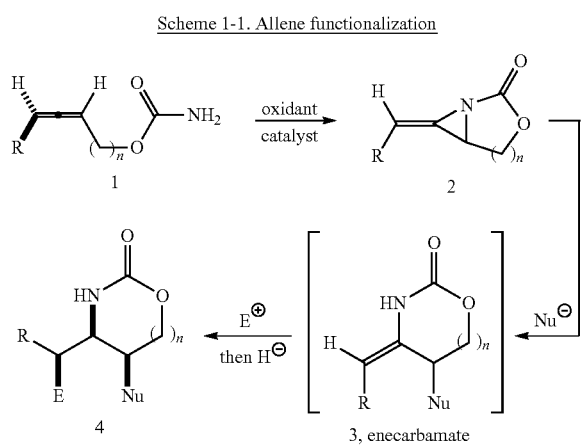

where R is, for example, $R^1$ as defined herein for Formula I.

Despite the great potential of bicyclic MAs to serve as scaffolds for allene oxidation, a significantly more detailed understanding of their preparation and reactivity is needed to provide new synthetic methods and improved synthetic routes to important compounds. A recent report on allene aziridination utilizing N-tosyloxycarbamates as nitrene precursors reported low yields of MAs and limited substrate scope (Robertson et al., Org. Biomol. Chem. 2010, 8, 3060). Thus, a first challenge was to examine factors including substrate, nitrene precursor, catalyst, and oxidant identity, to improve the efficiency of allene aziridination to synthetically useful levels and reasonable stereoselectivities.

Attempts to utilize N-tosyloxycarbamates as nitrene precursors were met with limited success for the synthesis of 7 (Table 1-1, entries 1-4), similar to previously reported results (Robertson et al., Org. Biomol. Chem. 2010, 8, 3060). The competitive formation of C—H amination product 8 was a recurring issue, as well as unproductive tosylation of 5 with another molecule of itself to yield 9 (Hayes et al., Chem. Commun. 2006, 4501). The use of sulfamate 6 was successful and gave no competing C—H amination, but ring-opening of the labile MA to 10 (entry 5) was problematic. Increasing the tether length between the allene and the sulfamate to three carbons (11, entry 6) completely suppressed ring-opening of the desired 11a, but also gave significant amounts of the C—H amination product 11b.

TABLE 1-1

N-Tosyloxycarbamate and sulfamate precursors.

| entry | substrate | products |
|---|---|---|
| 1[a] | 2 mol % $Rh_2(OAc)_4$ | 11% 7, 19% 8, 40% 9 |
| 2[a] | 2 mol % $Rh_2(NHTFA)_4$ | 16% 7, 29% 8, 20% 9 |
| 3[a] | 2 mol % $Rh_2(esp)_2$ | 21% 7, 15% 8, 22% 9 |
| 4[a,b] | 2 mol % $Rh_2(esp)_2$ | 42% 7, 15% 8. 41% 9 |

TABLE 1-1-continued

N-Tosyloxycarbamate and sulfamate precursors.

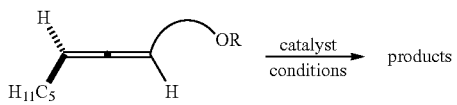

| entry | substrate | products | |
|---|---|---|---|
| 5[c] | 6 | 10 | 90%[d] |
| 6[e] | 11 | 11a | 38% |
| | | 11b | 42% |

[a] $K_2CO_3$, 0.1M in acetone.
[b] Substrate was added over 2 h and the acetone was dried over 4 A MS.
[c] 2.0 equiv PhIO, 4 A MS, $CH_2Cl_2$, rt.
[d] Products of hydrolysis of 10 were also observed.
[e] 2.0 equiv $PhI(OAc)_2$, MgO, $CH_2Cl_2$, 40° C.

For the purposes of isolating the target MAs, it was found that carbamates provided the best balance between the reactivity of the nitrene precursor and the subsequent stability and reactivity of the product. A series of allenic carbamates were subjected to various reaction conditions as illustrated in Table 1-2. It was found that the $Rh_2(OAc)_4$ and $Rh_2(oct)_4$ (oct=$O_2CC_7H_{15}$) catalysts previously used in this type of chemistry did not perform well in our hands. $Rh_2esp_2$ (esp=α,α,α',α'-tetramethyl-1,3-benzenedipropionate) and $Rh_2(TPA)_4$ (TPA=triphenylacetate) proved to be more effective catalysts, giving complete conversion of the carbamate in most cases.

TABLE 1-2

Carbamate precursors for allene aziridination.

R−CH=C=CH−CH2−O−C(=O)−NH2 →[2.5 mol % cat.][conditions] products

| entry | conditions | products |
|---|---|---|
| 1 | B: 67%$^a$ (39%) 12a E:Z >9:1<br>29%$^a$ (17%) 12b Z:E >9:1 | 12a (C5H11, bicyclic aziridine-oxazolidinone)<br>12b (C5H11, dihydrooxazinone with PivO) |
| 2 | B: 87% 13a E:Z 2.4:1 | 13a (C5H11, Me-substituted bicyclic) |
| 3 | 14a 14b<br>A: 46% E:Z 1.5:1  44%<br>B: 42% E:Z 4.1:1  45%<br>C: 66% E:Z 3:1  16%<br>D: 80% E:Z 4:1  15% | 14a (C5H11, bicyclic)<br>14b (C5H11, oxazolidinone-allene) |
| 4 | D: 46%$^b$ 15a E only<br>21% 15b | 15a (Ph(CH2)2, bicyclic)<br>15b (Ph(CH2)2, oxazolidinone-allene) |
| 5 | C: 49% 16a E:Z 1:1<br>17% 16b | 16a (TIPSOCH2, bicyclic)<br>16b (TIPSOCH2, oxazolidinone-allene) |
| 6 | D: 45%$^b$ 17a E only<br>23% 17b | 17a ($^t$Bu, bicyclic)<br>17b ($^t$Bu, oxazolidinone-allene) |

TABLE 1-2-continued

Carbamate precursors for allene aziridination.

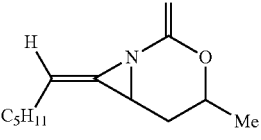

| entry | conditions | products |
|---|---|---|
| 7 | D: 48% 18a (E:Z 1.5:1)<br>31% 18b (dr 2:1) | 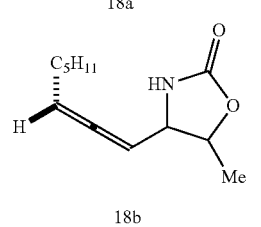<br>18a<br><br>18b |
| 8 | B: 10% 19a E:Z 2.8:1<br>72% 19b<br>D: 5% 19a E:Z 1.9:1<br>84% 19b | 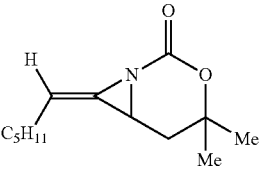<br>19a<br><br>19b |
| 9 | B: 21% 20a E:Z 3:1<br>57% 20b<br>D: 44% 20a E:Z 2.6:1<br>48% 20b | 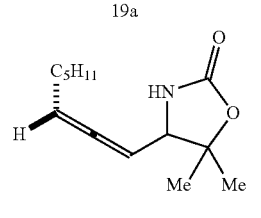<br>20a<br>(dr > 95:5)<br><br>20b |

TABLE 1-2-continued

Carbamate precursors for allene aziridination.

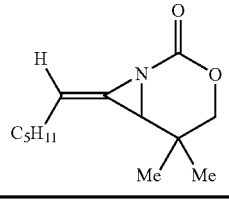

| entry | conditions | products |
|---|---|---|
| 10 | B: 94% 21a E:Z 3:1 | 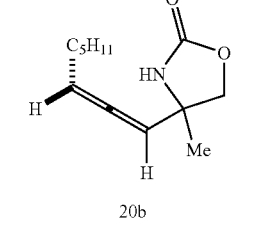 |

A: Rh$_2$(esp)$_2$, 2.0 equiv PhI(OAc)$_2$, 2.6 equiv MgO, CH$_2$Cl$_2$, 35° C.
B: Rh$_2$(esp)$_2$, 2.0 equiv PhI(OPiv)$_2$, 2.6 equiv MgO, CH$_2$Cl$_2$, 35° C.
C: Rh$_2$(esp)$_2$, 2.0 equiv PhIO, 4 Å MS, CH$_2$Cl$_2$, rt
D: Rh$_2$(TPA)$_4$, 2.0 equiv PhIO, 4 Å MS, CH$_2$Cl$_2$, rt
[a]Based on recovered starting material.
[b]None of the Z was isolated.

The choice of oxidant was also highly significant, as the leaving group released from the PhI(OAc)$_2$ or PhI(OPiv)$_2$ oxidants can ring-open sensitive MAs to yield the corresponding enecarbamates. For example (Table 1-2, entry 1), the Z isomer of MA 12a was susceptible to ring-opening by pivalate to give 12b in addition to the desired 12a. Placing a methyl group at the carbon α to the allene (entry 2) suppressed ring-opening to give an 87% yield of MA 13a as a 2.4:1 mixture of E:Z isomers at the olefin, with the methyl group and the aziridine proton maintaining a trans relationship in both alkene stereoisomers as observed by $^1$H NMR. The use of PhIO in the presence of 4 Å molecular sieves minimized the MA ring-opening and was the oxidant of choice for most of the reactions in Table 1-2.

Competing C—H amination can occur when the tether between the allene and the carbamate is two or more carbons. As illustrated in entry 3, the nature of the catalyst and oxidant influenced the aziridination vs. C—H amination ratio and the overall yield of the reaction. A Rh$_2$(esp)$_2$ catalyst with PhI(OAc)$_2$ (Condition A) gave good conversion to a mixture of 14a and 14b, but with little or no selectivity for aziridination over C—H amination. Changing the oxidant to PhI(OPiv)$_2$ (Condition B) improved the E:Z ratio of the MA product from 1.5:1 to 4.1:1, but did not increase the ratio of 14a:14b. Switching the oxidant to PhIO (Condition C) increased the ratio of 14a:14b to 4:1, with a 66% yield of the MA. Finally, changing the catalyst to Rh$_2$(TPA)$_4$ resulted in a 5.3:1 ratio of 14a:14b, with an 80% yield of the desired MA 14a (condition D).

Changing the side chain on the allene in combination with the use of Rh$_2$(TPA)$_4$ as the catalyst gave only the isolated E isomer (entries 4 and 6), but C—H amination was competitive. Placement of alkyl groups at positions α or β to the allene resulted in increased amounts of C—H amination products (entries 7-9), although the use of Rh$_2$(TPA)$_4$ did improve the aziridination/C—H amination ratio to some extent. Finally, shutting down the possibility of C—H amination (entry 10) gave an excellent 94% yield of the desired MA 21a.

NOESY 1D studies indicate that the E olefin geometry is present in the major product (see the General Experimental Information below for further details). Indirect evidence that interactions between the nitrenoid intermediate and the alkyl chain play a role in determining the E:Z ratio is suggested by entry 3 in Table 1-2. The more sterically demanding Rh$_2$(TPA)$_4$ complex increased the E:Z ratio from 1.5:1 to around 4:1. Increasing the bulk of the Rh ligands can improve the stereoselectivity of the aziridination.

The reactions in Table 1-2 represent the first reliable methods to access bicyclic MAs bearing electron-withdrawing groups on the aziridine nitrogen. Next, nucleophiles were evaluated for the preparation of an enecarbamate (Scheme 1-1, 3) intermediate via aziridine ring-opening. The additional ring strain present in 14a could allow for milder conditions than would typically be expected for aziridine ring opening (Scheme 1-2). Indeed, carboxylic acid nucleophiles gave the enecarbamates 22 and 26 in excellent yields, while the use of TMSCl at room temperature (~23° C.) gave 24 in good yield.

Because MA ring-opening using carboxylic acids as nucleophiles is relatively facile, Lewis acids could also likely activate the aziridine toward ring-opening with neutral nucleophiles. Indeed, the use of Sc(OTf)$_3$ as a mild Lewis acid in the presence of methanol and thiophenol promoted the ring-opening of 14a to give 27 and 28 in modest yields. No reaction occurred in the absence of the Lewis acid. Reaction with a cyanide nucleophile was also improved in the presence of a Lewis acid, although the double bond migrated to give an isomeric enecarbamate 25. Finally, treatment of 14a with NaN$_3$/TMSCl generated 23 in 82% yield, likely via initial ring-opening of the MA, followed by a [3,3]-sigmatropic rearrangement (Feldman et al., *J. Am. Chem. Soc.* 2005, 127, 13444; VanderWerf and Heasley, *J. Org. Chem.* 1966, 31, 3534.). As shown by the results in Scheme 1-2, carboxylic acids were found to be highly effective nucleophiles.

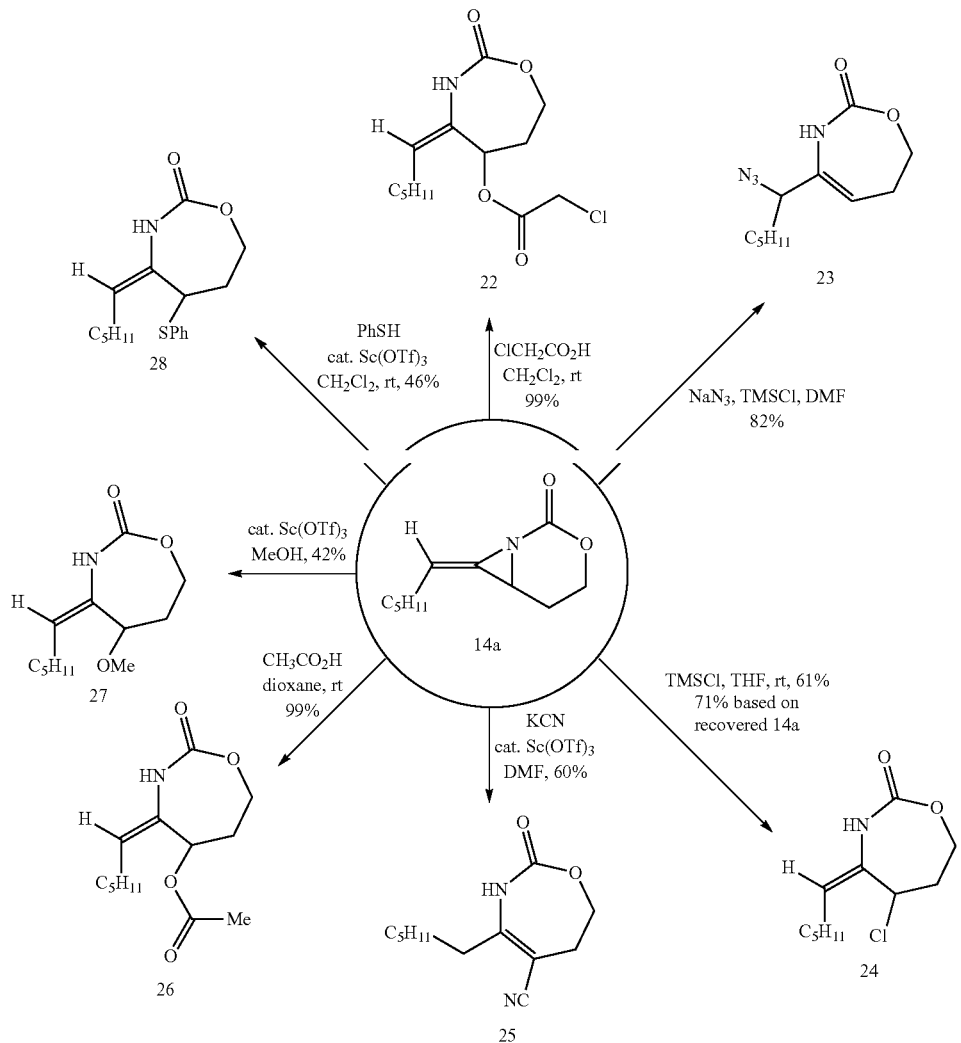

Scheme 1-2. Nucleophilic ring opening of bicyclic MAs.

As illustrated in entry 1 of Table 1-3, eliminating the ring-opening step and simply treating the MA 14a with NBS in a mixture of THF/H$_2$O gave 29 with an initial dr of 5.5:1. The α-bromoketone epimerized slowly over time to give a 1.1:1 mixture of diastereomers. Loss of stereochemical integrity was also noted when 26 was subjected to similar conditions, giving the tetrasubstituted bromoalkene 30 as a 2.3:1 mixture of E:Z isomers (entry 2).

The power of allene aziridination to generate multiple carbon-heteroatom bonds in a single pot was further demonstrated by a tandem aziridination/ring-opening of the allene 13 to 32 (Table 1-3, entry 4). The substrate was treated under Condition B (Table 1-2) to form the intermediate MA. N-aminophthalimide and additional oxidant were then added to the same pot to yield the unusual spiroaminal 32 in 46% yield, where four new carbon-heteroatom bonds have been formed

TABLE 1-3

Formation of three contiguous carbon-heteroatom bonds from allenes.

| entry | substrate | conditions | product |
|---|---|---|---|
| 1 | 14a | 1.1 equiv NBS THF/H$_2$O, rt 63% dr 5.5:1[a] | 29 |
| 2 | 26 | 1.4 equiv NBS THF/H$_2$O, rt 68% E:Z 2.3:1 | 30 |
| 3 | 26 | 1.1 equiv NBS THF/H$_2$O, rt NaCNBH$_3$/AcOH 73% dr 10:1 | 31 |
| 4 | 13 | Condition B (Table 2) then PhtNNH$_2$, PhI(OAc)$_2$, K$_2$CO$_3$ 46% dr a:b > 95:5 dr ab:c 2.4:1 | 32 |

[a]Compound epimerized to a 1.1:1 mixture upon standing.

Isomerization of an intermediate imine could lead to the brominated olefin. This prompted the addition of NaCNBH$_3$ as a reductant to the reaction mixture, whereupon 31 was obtained in 73% yield with a dr of 10:1 (see the General Experimental Information below for details and a proposed stereochemical model). Anchimeric assistance from the acetate group of the enecarbamate may play a role in controlling the stereochemical outcome of the reaction. This result, coupled with the ease of ring-opening MAs with acids, provides an important step toward flexible, stereoselective methods for allene functionalization.

in a single pot. The stereochemistry between the Me and OAc groups at a and b was exclusively trans by $^1$H NMR (see the General Experimental Information below for further details). The 2.4:1 E:Z ratio of the MA olefin isomers (see 13a, Table 1-2, entry 2) appears to have been translated from the intermediate MA into a 2.4:1 dr in the final product 32. This result indicates that better control of the E:Z stereochemistry in the MA formation translates into excellent dr in the spiroaminal products. Additional discussion of spiroaminal products can be found in Example 2 below.

Thus, a synthetically useful approach for the preparation of bicyclic MAs activated by electron-withdrawing groups has been described. The potential of these MAs as scaffolds for the construction of motifs bearing three contiguous heteroatom-bearing carbons has been demonstrated. Use of enantioenriched allenes (Ogasawara, *Tetrahedron: Asymmetry* 2009, 20, 259; Kim and Williams, *Curr. Opin. Drug Disc.* 2006, 11, 870) for the asymmetric syntheses of MAs can provide the corresponding enantioenriched products. A variety of nucleophiles and electrophiles for efficient and flexible multi-component reactions that install multiple carbon-heteroatom bonds into a simple allene precursor has also been demonstrated.

I. General Experimental Information.

All glassware was either oven-dried overnight at 130° C. or flame-dried under a stream of dry nitrogen prior to use. Unless otherwise specified, reagents were used as obtained from the vendor without further purification. Tetrahydrofuran and diethyl ether were freshly distilled from purple Na/benzophenone ketyl. Dichloromethane, acetonitrile and toluene were dried over $CaH_2$ and freshly distilled prior to use. All other solvents were purified in accordance with "Purification of Laboratory Chemicals" (Armarego and Chai, 6$^{th}$ ed., Elsevier: Burlington, Mass., 2009). Air- and moisture-sensitive reactions were performed either in a Braun LabStar glovebox under an atmosphere of nitrogen or using standard Schlenk techniques under an atmosphere of nitrogen. Analytical thin layer chromatography (TLC) was performed utilizing pre-coated silica gel 60 $F_{254}$ plates containing a fluorescent indicator, while preparative chromatography was performed using SilicaFlash P60 silica gel (230-400 mesh) via Still's method (Still, Kahn, and Mitra, *J. Org. Chem.* 1978, 43, 2923). Unless otherwise stated, the mobile phases for column chromatography were mixtures of hexanes/ethyl acetate. Columns were typically run using a gradient method, beginning with 100% hexanes and gradually increasing the polarity using ethyl acetate. Various stains were used to visualize reaction products, including p-anisaldehyde, $KMnO_4$, ceric ammonium nitrate and phosphomolybdic acid in ethanol stain.

$^1$H NMR and $^{13}$C NMR spectra were obtained using Bruker-300, Varian Inova-500, Varian Unity-500 or Varian Inova-600 NMR spectrometers. For $^1$H NMR, chemical shifts are reported relative to residual protiated solvent peaks (δ 7.26, 2.49, 7.15 and 4.80 ppm for $CDCl_3$, $(CD_3)_2SO$, $C_6D_6$ and $CD_3OD$ respectively). $^{13}$C NMR spectra were measured at either 125 MHz or 150 MHz on the same instruments noted above for recording $^1$H NMR spectra. Chemical shifts were again reported in accordance to residual protiated solvent peaks (δ 77.0, 39.5, 128.0 and 49.0 ppm for $CDCl_3$, $(CD_3)_2SO$, $C_6D_6$, and $CD_3OD$, respectively). IR spectral data were obtained using a Bruker Vector 22 spectrometer using either a thin film or an ATR adapter. Melting points were obtained with a Mel-Temp II (Laboratory Devices, Inc.) melting point apparatus. Accurate mass measurements were acquired at the University of Wisconsin, Madison using a Micromass LCT (electrospray ionization, time-of-flight analyzer or electron impact methods).

II. Preparation of Allene Substrates.

The preparations of the majority of the allene substrates were accomplished according to literature procedures (Lang and Hansen, *Helv. Chim. Acta* 1980, 63, 438; Alexakis et al., *Tetrahedron Lett.* 1985, 26, 4197; Buchner et al., *Org. Lett.* 2009, 11, 2173; Lang and Hansen, *Org. Synth. Coll. Vol. 7*, 1990, 232; Henderson and Heathcock, *J. Org. Chem.* 1988, 53, 4736).

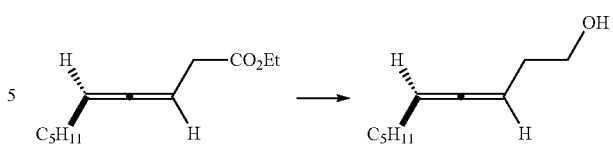

Compound S1. An oven-dried 250 mL flask was charged with $LiAlH_4$ (2.7 g, 71.4 mmol, 4.0 equiv) and 50 mL of THF. The suspension was cooled to 0° C. and a solution of the ester (3.5 g, 17.8 mmol, 1.0 equiv) in 25 mL of THF was added dropwise over 40 min. The reaction mixture was warmed slowly to rt and stirred for 4 h, or until complete conversion was seen by TLC (3:1 hexanes/ethyl acetate). The reaction was cooled back to 0° C. and quenched carefully by successive additions of 2.7 mL of water, 2.7 mL of 15% NaOH and 8.1 mL of water. The mixture was stirred vigorously at rt for 30 min, the salts removed by filtration and the filtrate dried over $MgSO_4$. The volatiles were removed under reduced pressure to give the product as a colorless oil in 92% yield. The material was sufficiently pure by $^1$H NMR and was used without further purification. $^1$H NMR (300 MHz, $CDCl_3$) δ 5.13 (m, 2 H), 3.71 (q, 2 H, J=6.0 Hz), 2.26 (ddd, J=6.3, 6.3, 2.9 Hz, 2 H), 1.99 (ddd, J=7.0, 7.0, 2.9 Hz, 2 H), 1.6-1.2 (m, 8 H), 0.90, (t, J=6.3 Hz, 3 H). $^{13}$C NMR (75 MHz, $CDCl_3$) δ 204.8, 91.8, 87.3, 62.2, 32.5, 31.5, 29.0, 22.7, 14.2.

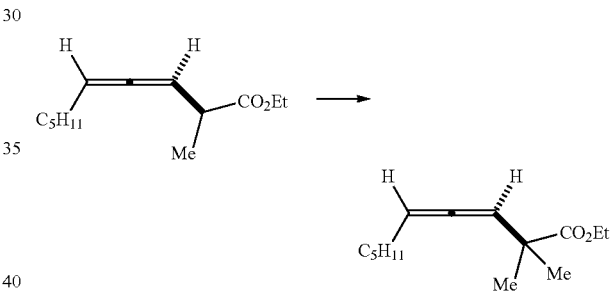

Compound S2. To a dry 100 mL Schlenk flask was added N,N-diisopropylamine (2.9 mL, 20.9 mmol) and 40 mL of dry THF. The solution was cooled to −78° C. under an atmosphere of nitrogen, then n-BuLi (8.77 mL, 19.0 mmol, 2.17 M in hexanes) was added dropwise over 20 min. The resulting solution was stirred for an additional 20 min at −78° C., warmed to 0° C. in an ice bath and stirred for 10 min to ensure complete LDA formation. The solution was once again cooled to −78° C. and the allenic ester (4.0 g, 19.0 mmol) dissolved in 10 mL dry THF was added dropwise to the cold LDA solution. MeI (1.2 mL, 19.0 mmol) was then added dropwise to the red solution. The reaction mixture was stirred for 1 h at −78° C., then an additional 30 min at 0° C. The mixture was quenched with 20 mL of saturated $NH_4Cl$ and extracted with three portions of EtOAc. The combined organics were washed three times with brine, dried over $Na_2SO_4$ and filtered. The filtrate was concentrated under reduced pressure to yield the methylated product as a yellow oil (3.8 g, 89%), which was used without further purification. $^1$H NMR (300 MHz, $CDCl_3$) δ 5.31 (m, 1H), 5.24 (dd, 1H, J=6.8, 6.1 Hz), 4.10 (q, 2H, J=7.4 Hz), 1.98 (m, 2H), 1.4-1.16 (overlapping signals, 15H total), 0.86 (t, 3H, J=6.0 Hz). $^{13}$C NMR (75 MHz, $CDCl_3$) δ 202.1, 176.5, 97.7, 94.4, 60.6, 42.3, 31.4, 28.7, 25.5, 25.3, 22.5, 14.1, 14.0.

III. Preparation of Allenic N-Tosyloxycarbamates, Sulfamates and Carbamates.

General procedure for the preparation of N-tosyloxycarbamates. The N-tosyloxycarbamate for the studies described in Table 1-1 was prepared according to a general literature procedure described by Lebel and co-workers (*Org. Lett.* 2007, 9, 4797). General procedure for the preparation of sulfamates. The following sulfamates were prepared according to a general literature procedure described by Du Bois and co-workers (*J. Am. Chem. Soc.* 2001, 123, 6935).

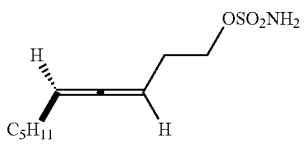

Compound 6. The product was obtained as a colorless oil in 62% yield. $^1$H NMR (300 MHz, $C_6D_6$) δ 5.12 (m, 1H), 4.94 (m, 1H), 3.89 (overlapping signals, 4H), 2.13 (br ddd, J=8.9, 6.9, 3.2 Hz, 2H), 1.93 (br ddd, J=10.1, 6.5, 3.2 Hz, 2H), 1.30 (overlapping signals, 6H), 0.88 (br t, J=6.9 Hz, 3H). $^{13}$C NMR (75 MHz, $C_6D_6$) δ 204.9, 92.3, 86.1, 69.7, 31.5, 29.0, 28.8, 28.7, 22.7, 14.1. HRMS (ESI) m/z calculated for [M+H]$^+$ 234.1159, found 234.1167.

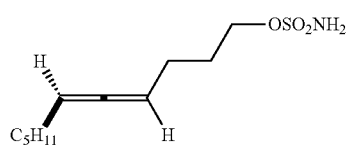

Compound 11. The product was obtained in 67% as a thick, colorless oil. $^1$H NMR (500 MHz, CDCl$_3$) δ 5.10 (m, 2H), 4.82 (br s, 2 H), 4.25 (t, 2H, J=6.3 Hz), 2.11 (m, 2H), 1.97 (m, 2H), 1.87 (m, 2H), 1.39 (m, 2H), 1.30 (m, 4H), 0.89 (t, 3H, J=7.2 Hz). $^{13}$C NMR (125 MHz, CDCl$_3$) δ 204.0, 92.2, 89.2, 70.8, 31.3, 28.8, 28.8, 28.0, 24.6, 22.5, 14.1. HRMS (ESI) m/z calculated for [M+NH$_4$]$^+$ 265.1581, found 265.1566.

General procedure for the preparation of carbamates. The following carbamates were prepared according to a general procedure described by Du Bois and Espino (*Angew. Chem. Int. Ed.* 2001, 40, 598).

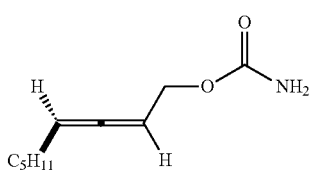

Compound 12. The product was obtained in 99% yield as a thick oil that solidified upon storage in the freezer. $^1$H NMR (300 MHz, CDCl$_3$) δ 5.22 (m, 2H), 4.85 (br s, 2H), 4.58-4.42 (br m, 2H), 1.98 (m, 2H), 1.42-1.2 (several overlapping signals, 6H total), 0.86 (t, 3H, J=7.5 Hz). $^{13}$C NMR (75 MHz, CDCl$_3$) δ 205.2, 156.8, 92.9, 87.0, 63.5, 31.1, 28.6, 28.2, 22.3, 13.9. HRMS (ESI) m/z calculated for [M+Na]$^+$ 206.1152, found 206.1155.

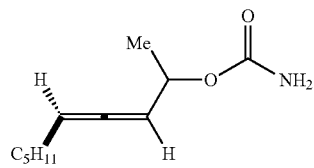

Compound 13. The product was obtained in 96% yield as a thick oil that solidified upon storage in the freezer. $^1$H NMR (300 MHz, CDCl$_3$) δ 5.27 (overlapping signals, 3H), 5.06 (br s, 2H), 2.03 (br dd, 2H, J=13.5, 6.7 Hz), 1.41-1.33 (overlapping signals, 9H total), 0.91 (br t, 3H, J=6.7 Hz). $^{13}$C NMR (75 MHz, CDCl$_3$) δ 205.5, 157.4, 93.1, 87.3, 63.7, 31.4, 28.8, 28.5 (2), 22.6, 14.2. HRMS (ESI) m/z calculated for [M+Na]$^+$ 220.1308, found 220.1306.

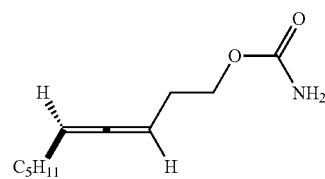

Compound 14. The product was obtained in 90% yield as a thick oil that solidified upon storage in the freezer. $^1$H NMR (300 MHz, CDCl$_3$) δ 5.13-4.90 (overlapping signals, 4H total), 4.02 (dd, 2H, J=6.9, 6.9 Hz), 2.21 (ddd, 2H, J=10.1, 6.3, 3.2 Hz), 1.89 (ddd, 2H, J=7.0, 6.3, 3.2 Hz), 1.31-1.20 (overlapping signals, 6H total), 0.80 (t, 3H, J=6.3 Hz). $^{13}$C NMR (75 MHz, CDCl$_3$) δ 204.8, 157.6, 92.0, 86.7, 64.6, 31.5, 28.9 (2), 22.7, 14.2. HRMS (ESI) m/z calculated for [M+Na]$^+$ 220.1308, found 220.1300.

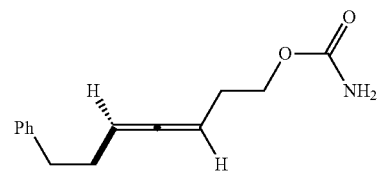

Compound 15. The product was obtained in 78% yield as a thick, colorless oil that solidified upon storage in the freezer. $^1$H NMR (500 MHz, CDCl$_3$) δ 7.29-7.25 (Ar, 2H), 7.20-7.16, (Ar, 3H), 5.21-5.15 (m, 1H), 5.10-5.05 (m, 1H), 4.74 (br s, 2H), 4.06 (t, J=7.5 Hz, 2H), 2.72 (dd, J=8.8, 8.8 Hz, 2H), 2.34-2.23 (m, 4H). $^{13}$C NMR (125 MHz, CDCl$_3$) δ 204.7, 157.0, 141.7, 128.5, 128.3, 125.8, 91.1, 87.2, 64.3, 35.3, 30.4, 28.6. HRMS (ESI) m/z calculated for [M–CNH$_3$O$_2$]$^+$ 170.1091, found 170.184.

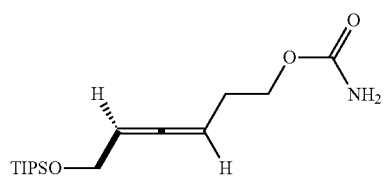

Compound 16. The product was obtained in 89% yield as a thick, colorless oil that solidified upon storage in the freezer.

¹H NMR (500 MHz, CDCl₃) δ 5.31-5.26 (m, 1H), 5.21-5.00 (overlapping signals, 3 H total), 4.24 (ddd, J=6.4, 2.9, 1.5 Hz, 2H), 4.11 (t, J=6.7 Hz, 2H), 2.33 (qd, J=7.1, 3.0 Hz, 2H), 1.14-1.02 (overlapping signals, 21 H total). ¹³C NMR (125 MHz, CDCl₃) δ 203.9, 157.2, 92.5, 88.0, 64.1, 61.6, 28.3, 17.9, 11.9. HRMS (ESI) m/z calculated for [M–C₃H₇]⁺ 270.1520; found 270.1521.

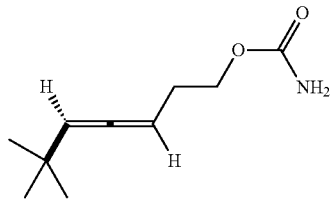

Compound 17. The product was obtained in 79% yield as a waxy solid. ¹H NMR (300 MHz, CDCl₃) δ 5.14 (m, 2H), 4.73 (br s, 2H), 4.12 (t, J=6.9 Hz, 2H), 2.32 (m, 2 H), 1.04 (s, 9 H). ¹³C NMR (75 MHz, CDCl₃) δ 202.0, 157.1, 104.0, 88.6, 64.7, 31.9, 30.3, 29.0. HRMS (ESI) m/z calculated for [M+.] 183.1254, found 183.1259.

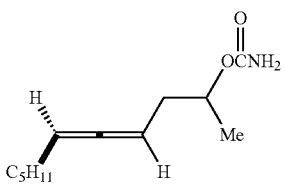

Compound 18. A Weinreb amide approach similar to Marcus et al., *Angew. Chem. Int. Ed.* 2008, 47, 6379 was utilized to prepare the parent alcohol. The product was obtained in 92% yield as a thick, colorless oil that solidified upon storage in the freezer. ¹H NMR (300 MHz, CDCl₃) δ 5.06 (m, 2H), 4.84 (m, 1H), 4.67 (br s, 2H), 2.24 (m, 2H), 1.98 (m, 2H), 1.31-1.42 (m, 6H), 1.26 (d, J=6.3 Hz, 3H), 0.89 (t, J=6.3 Hz, 3H). ¹³C NMR (75 MHz, CDCl₃) δ 205.1, 156.6, 91.1, 91.1, 86.1, 86.1, 71.3, 71.2, 35.9, 31.3, 28.8, 28.7, 22.5, 19.6, 14.0. HRMS (ESI) m/z calculated for [M+Na]⁺ 234.1465, found 234.1461.

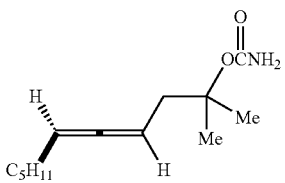

Compound 19. The compound was obtained in 76% yield as a thick oil that solidified upon storage in the freezer. ¹H NMR (300 MHz, CDCl₃) δ 5.05 (m, 2H), 4.58 (br s, 2H), 2.45 (m, 2H), 1.98 (ddd, J=7.0, 7.6, 3.3 Hz, 2H), 1.38 (overlapping signals, 12H), 0.89 (br t, J=6.8 Hz, 3H). ¹³C NMR (75 MHz, CDCl₃) δ 205.9, 156.4, 90.5, 86.0, 81.6, 41.2, 31.5, 29.1, 29.0, 26.1, 26.1, 22.7, 14.3. HRMS (ESI) m/z calculated for [M+Na]⁺ 248.1621, found 248.1620.

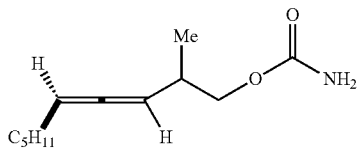

Compound 20. The product was obtained in 96% yield as a thick oil that solidified upon storage in the freezer. ¹H NMR (300 MHz, CDCl₃) δ 5.13 (overlapping signals, 4H), 3.94 (m, 2H), 2.47 (m, 1H), 1.99 (br dd, J=13.4, 6.7 Hz, 2H), 1.34 (overlapping signals, 6H), 1.04 (br dd, J=6.8, 2.4 Hz, 3H), 0.89 (br t, J=6.7 Hz, 3H). ¹³C NMR (75 MHz, CDCl₃) δ 203.6, 157.7, 93.1, 93.0, 69.6, 33.1, 31.5, 29.0 (2), 22.6, 16.9, 14.2. HRMS (ESI) m/z calculated for [M+Na]⁺ 234.1463, found 234.1465.

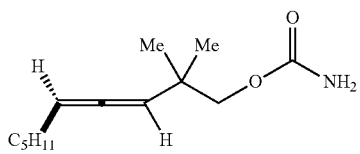

Compound 21. The product was obtained in 98% yield as a thick, colorless oil. ¹H NMR (300 MHz, CDCl₃) δ 5.20 (dd, 1H, J=6.5, 3.1 Hz), 5.06 (dd, 1H, J=3.1, 2.9 Hz), 4.91 (br s, 2H), 3.86 (s, 2H), 1.98 (m, 2H), 1.42-1.24 (m, 6H total), 1.03 and 1.04 (2 s, 3H each), 0.89 (t, 3H, J=7.6 Hz). ¹³C NMR (75 MHz, CDCl₃) δ 202.5, 157.5, 98.5, 93.6, 73.4, 35.5, 31.6, 29.1, 29.0, 25.1, 25.0, 22.7, 14.2. HRMS (ESI) m/z calculated for [M+Na]⁺ 248.1621, found 248.1620.

IV. Intramolecular Synthesis of Methylene Aziridines.

General Procedure A. The allenic carbamate 14 (0.200 g, 1.02 mmol) and 11 mL of dry CH₂Cl₂ were added to a dry 50 mL Schlenk flask. The solution was kept under an atmosphere of nitrogen and charged with MgO (0.106 g, 2.64 mmol) and Rh₂(esp)₂ (0.0113 g, 0.0255 mmol). The resulting blue-green mixture was stirred for 10 min at rt, then PhI(OAc)₂ (0.329 g, 1.02 mmol) was added, the flask fitted with a reflux condenser and the reaction mixture was heated to 35° C. in an oil bath for 1 h. Two additional 0.164 g (0.508 mmol, 0.5 equiv) portions of PhI(OAc)₂ were added at 1 h intervals. The reaction was monitored by TLC until complete (4 h). The heterogeneous mixture was concentrated under reduced pressure and the brick red residue chromatographed on silica gel using a hexanes/EtOAc gradient. Pre-treatment of the silica gel column with 99.5:0.5 hexanes/triethylamine, followed by flushing with four column volumes of hexanes prior to loading the sample often improved the separation and prevented the decomposition of sensitive methylene aziridines.

General Procedure B. A dry 50 mL Schlenk flask was charged with allenic carbamate 14 (0.200 g, 1.02 mmol), followed by 6 mL of dry CH₂Cl₂. The solution was kept under an atmosphere of nitrogen and charged with MgO (0.106 g, 2.64 mmol) and Rh₂esp₂ (0.0192 g, 0.0250 mmol). The resulting blue-green mixture was stirred for 10 min at rt, then 0.829 g PhI(OPiv)₂ (2.04 mmol) dissolved in 5 mL of dry CH₂Cl₂ was added dropwise over the course of 1.5 h via syringe pump. The flask was fitted with a reflux condenser and heated to 35° C. in an oil bath for 2 h or until TLC indicated the reaction was complete. The heterogeneous mixture was concentrated under reduced pressure and the brick red residue chromatographed on silica gel eluting with a hexanes/EtOAc gradient.

General Procedure C. A dry 50 mL Schlenk flask was charged with allenic carbamate 14 (0.370 g, 1.88 mmol) and 19 mL of dry CH$_2$Cl$_2$. The solution was kept under an atmosphere of nitrogen and charged with 4 Å MS (0.925 g) and Rh$_2$esp$_2$ (0.0356 g, 0.0470 mmol). The resulting blue-green mixture was stirred for 10 min at rt, then PhIO (0.826 g, 3.75 mmol) was added in one portion. The heterogeneous light green suspension was stirred at rt until complete by TLC (usually within 4 h). The resulting mixture was concentrated under reduced pressure, taken up in Et$_2$O and filtered through a pad of Celite. The filtrate was concentrated under reduced pressure and the brick red residue was chromatographed on SiO$_2$ gel eluting using a hexanes/EtOAc gradient.

General Procedure D. A dry 50 mL Schlenk flask was charged with the allenic carbamate 14 (0.370 g, 1.88 mmol) and 19 mL of dry CH$_2$Cl$_2$. The solution was kept under an atmosphere of nitrogen and charged with 4 Å MS (0.925 g) and Rh$_2$(TPA)$_4$ (0.0660 g, 0.0470 mmol). The resulting blue-green mixture was stirred for 10 min at rt, then PhIO (0.826 g, 3.75 mmol) was added in one portion, and the heterogeneous light green suspension was stirred at rt until complete by TLC (usually within 4 h). The resulting mixture was concentrated under reduced pressure, taken up in Et$_2$O and filtered through a pad of Celite. The filtrate was concentrated under reduced pressure and the brick red residue was chromatographed on silica gel eluting with a hexanes/EtOAc gradient. See Hashioto et al., *Tetrahedron Lett.* 1992, 33, 2709.

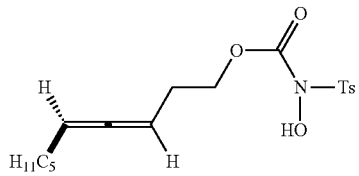

Compound 9. Obtained a mixture of diastereomers. $^1$H NMR (300 MHz, CDCl$_3$) δ 7.92 and 7.8 (2 d, 2H total, J=7.8 Hz), 7.41 and 7.32 (2 d, 2H total, J=8.0 Hz), 5.2-5.03 and 4.9 (2 m, 2H total), 4.08 and 3.72 (2 dd, 2H total, J=6.8, 6.8 Hz), 2.5 and 2.46 (2 s, 3H total), 2.31-1.84 (several m, 5H total), 1.42-1.2 (br m, 6H total), 0.87 (2 overlapping t, 3H total). $^{13}$C NMR (75 MHz, CDCl$_3$) δ 204.5, 204.4, 151.7, 146.5, 146.3, 132.9, 130.5, 129.7, 129.0, 92.2, 91.5, 87.0, 85.3, 68.1, 61.9, 32.2, 31.2, 28.7, 28.6, 28.4, 27.7, 22.3, 21.7, 21.6, 13.9.

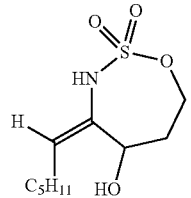

Compound 10. A pure sample of the product was obtained in 34% yield, with an additional 58% yield isolated as approximately a 1:1 mixture of 10 and the hydrolyzed ketone product following purification by column chromatography (63% yield of 10 and 29% of the ketone). $^1$H NMR (500 MHz, C$_6$D$_6$) δ 6.58 (s, 1H), 5.72 (t, J=6.5 Hz, 1H), 4.47 (t, J=13.0 Hz, 1H), 4.22 (br s, 1H), 3.53 (br dt, J=13.0, 3.3 Hz, 1H), 1.69 (overlapping signals, 3H), 1.55 (ddt, J=12.3, 3.3, 3.2 Hz, 1H), 1.18 (overlapping signals, 6H), 0.87 (br t, J=6.8 Hz, 3H). $^{13}$C NMR (125 MHz, C$_6$D$_6$) δ 131.6, 130.5, 64.1, 63.7, 36.1, 31.2, 28.7, 26.5, 22.4, 13.8. HRMS (ESI) m/z calculated for [M+Na]$^+$ 272.0927, found 272.0925.

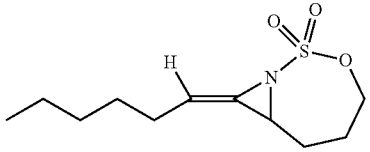 [SMILES: CCCCC/C=C1\C2CCCOS(=O)(=O)N12]

Compound 11a. The product was obtained in 38% yield as a thick, colorless oil using General Procedure B. $^1$H NMR (500 MHz, C$_6$D$_6$) δ 5.57 (t, J=6.8 Hz, 1H), 3.70 (td, J=11.6, 1.7 Hz, 1H), 3.51 (dt, J=12.1, 3.5 Hz, 1H), 2.96 (s, 1H), 1.92 (m, 1H), 1.82 (2 dd, J=7.3, 7.3 Hz, 2H total), 1.68 (m, 1H), 1.04-1.36 (m, 7H), 0.88 (overlapping m and t, J=7.0 Hz, 4H). $^{13}$C NMR (125 MHz, C$_6$D$_6$) δ 128.2, 128.0, 127.8, 122.2, 106.8, 70.7, 45.9, 31.6, 28.8, 28.6, 27.2, 26.6, 22.7, 14.1. HRMS (ESI) m/z calculated for [M+Na]$^+$ 268.0978, found 268.0972.

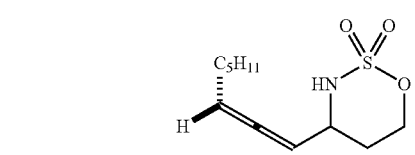

Compound 11b. The product was obtained using General Procedure B in 42% yield as a thick, colorless oil that solidified to a white wax upon refrigeration. $^1$H NMR (500 MHz, C$_6$D$_6$) δ 5.12 (m, 1H), 4.80 (br s, 1H), 4.19 (dd, J=11.8, 11.8 Hz, 1H), 3.91 (m, 2H), 3.69 (m, 1H), 1.83 (m, 2H), 1.07-1.33 (m, 7H), 0.89 (2 sets of triplets, J=7.0 Hz, 3H), 0.78 (m, 1H). $^{13}$C NMR (125 MHz, C$_6$D$_6$) δ 203.2, 202.8, 96.2, 95.9, 91.4, 91.3, 71.1, 71.0, 53.7, 31.6, 31.5, 29.6, 29.1, 29.0, 28.9, 28.7, 28.6, 22.7, 14.2. HRMS (EI) m/z calculated for [M+H]$^+$ 246.1159, found 246.1157.

Compound 12a. The product was obtained in 39% yield as a single isomer having the E configuration about the olefin when PhI(OPiv)$_2$ was used as the oxidant (General Procedure B). If the remaining starting material was accounted for, the yield increased to 67%. Another 17% yield of the product that had been ring-opened by pivalic acid was obtained as a single diastereomer 12b (29% based on recovered starting material). $^1$H NMR (300 MHz, CDCl$_3$) δ 5.74 (dd, 1H, J=6.9, 6.9 Hz), 4.45 (2 overlapping signals, 2H), 3.68 (br m, 1H), 2.17 (2 d, 2H, J=7.0 Hz), 1.44-1.21 (several signals, 6H), 0.86 (t, 3H, J=7.0 Hz). $^{13}$C NMR (125 MHz, CDCl$_3$) δ 164.6, 123.8, 107.6, 66.5, 41.4, 31.3, 28.7, 28.4, 22.5, 14.1. HRMS (ESI) m/z calculated for [M+H]$^+$ 181.1098, found 181.1090.

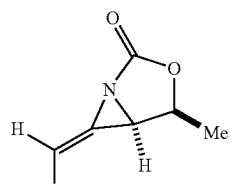

major

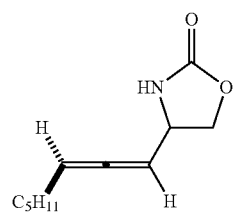

Compound 14b. The product was obtained using General Procedure A in 44% yield as a clear, thick oil. $^1$H NMR (300 MHz, CDCl$_3$) δ 6.01 (br d, 1H, J=7.3 Hz), 5.32 (m, 1H), 5.11 (m, 1H), 4.49 (dd, 1H, J=8.7, 8.2 Hz), 4.32 (dd, 1H, J=13.8, 6.1 Hz), 4.13 (dd, 1H, J=8.4, 5.9 Hz), 1.98 (m, 2H), 1.35-1.26 (br m, 6H), 0.85 (t, 3H, J=6.7 Hz). $^{13}$C NMR (75 MHz, CDCl$_3$) δ 203.7, 159.4, 95.4, 95.2, 91.1, 70.2, 52.1, 51.9, 31.1, 28.7, 28.5, 28.3, 28.2, 22.3, 13.9. HRMS (ESI) m/z calculated for [M+H]$^+$ 196.1333, found 196.1339.

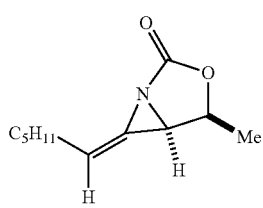

minor

Compound 13a. The product was obtained using General Procedure B as a 2.4:1 mixture of E:Z isomers in 76% isolated yield using PhI(OPiv)$_2$ as the oxidant. A 1.7:1 mixture of E:Z isomers was obtained when PhI(OAc)$_2$ was used as the oxidant. Major product: $^1$H NMR (500 MHz, CDCl$_3$) δ 5.79 (dd, 1H, J=7.6, 7.3 Hz), 4.86 (m, 1H), 3.64 (d, 1H, J=4.8 Hz), 2.16 (2 d, 2H, J=7.3 Hz), 1.41-1.28 (overlapping signals, 9H), 0.86 (t, 3H, J=7.1 Hz). Minor product: $^1$H NMR (500 MHz, CDCl$_3$) δ 5.53 (dd, 1H, J=7.4, 7.3 Hz), 4.86 (m, 1H), 3.64 (d, 1H, J=4.8 Hz), 2.31 (2 d, 2H, J=7.7 Hz), 1.41-1.28 (overlapping signals, 9H), 0.86 (t, 3H, J=7.1 Hz). Both isomers: $^{13}$C NMR (125 MHz, CDCl$_3$) δ 163.5 (2), 123.3, 123.2, 108.5, 108.4, 74.5, 74.4, 45.7, 45.5, 31.2, 31.1, 29.6, 28.9, 28.8, 28.7, 27.6, 22.3, 18.2, 17.7, 13.9 (2). HRMS (ESI) m/z calculated for [M+Na]$^+$ 218.1152, found 218.1162.

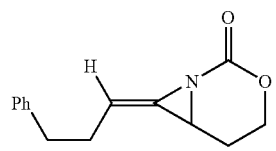

Compound 15a. The product was obtained as a 1.3:1.0 mixture of E:Z isomers before purification via column chromatography using General Procedure D. After purification, only the E isomer was present in 46% yield. $^1$H NMR (500 MHz, C$_6$D$_6$) δ 7.13-6.92 (Ar, 5H), 5.46 (dd, J=8.7, 7.7 Hz, 1H), 3.48 (ddd, J=12.9, 10.9, 2.5 Hz, 1H), 3.32 (ddd, J=10.7, 4.2, 2.8 Hz, 1H), 2.46-2.32 (m, 3H), 2.19-2.01 (m, 2H), 0.85 (ddt, J=14.7, 6.3, 2.8 Hz, 1H), 0.38-0.30 (m, 1H). $^{13}$C NMR (125 MHz, C$_6$D$_6$) δ 154.9, 141.2, 128.6, 128.3, 126.9, 125.9, 100.7, 67.9, 38.7, 35.3, 30.2, 22.9. HRMS (ESI) m/z calculated for [M]$^+$ 229.1098; found 229.1095.

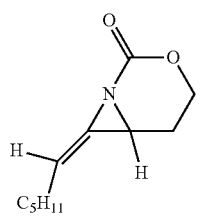

Compound 14a. The product was obtained using General Procedure A in 46% yield after column chromatography as a thick, clear oil. The major isomer had the E configuration at the olefin. Both the yield and the E:Z ratio were improved by using the Rh$_2$(TPA)$_4$ catalyst and PhIO as the oxidant to give an 80% yield of 14a with a 4:1 E:Z ratio. $^1$H NMR (300 MHz, CDCl$_3$) δ 5.55 (dd, 1H, J=7.3, 6.8 Hz), 4.50 (dd, 1H, J=11.3, 2.1 Hz), 4.33 (ddd, 1H, J=11.0, 4.0, 2.6 Hz), 3.40 (dd, 1H, J=8.0, 6.5 Hz), 2.34 (m, 2H), 2.13 (ddd, 2H, J=8.5, 7.2, 1.6 Hz), 1.59-1.2 (m, 6H), 0.85 (t, 3H, J=8.0 Hz). $^{13}$C NMR (75 MHz, CDCl$_3$) δ 156.4, 125.5, 103.2, 68.8, 39.5, 31.3, 28.8, 28.2, 24.3, 22.4 14.0. HRMS (ESI) m/z calculated for [M+H]$^+$ 196.1333, found 196.1342.

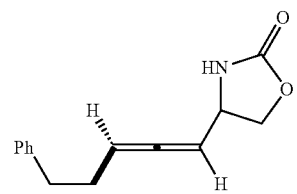

Compound 15b. The C—H amination product was present in 21% yield as an inseparable mixture of diastereomers. $^1$H NMR (500 MHz, C$_6$D$_6$) δ 7.18-6.99 (Ar, 5H), 6.34 (2 br s, NH, both diastereomers), 5.08-5.03 (m, 1H), 4.66-4.61 (m, 1H), 3.62-3.58 (m, 1H), 3.44-3.40 (m, 2H), 2.60-2.43 (m, 2H), 2.14-2.03 (m, 2H). $^{13}$C NMR: (125 MHz, C$_6$D$_6$) δ 203.6, 203.3, 159.5, 141.2, 128.5, 128.4, 128.3, 126.0, 126.0, 125.9, 94.0, 93.9, 91.9, 69.4, 69.2, 51.4, 51.2, 34.8, 29.8, 29.7. HRMS (ESI) m/z calculated for [M−CH$_3$NO$_2$]$^+$ 168.0934, found 168.0929.

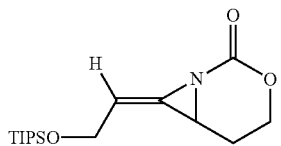

Compound 16a. The product was obtained as a 1:1 mixture of E:Z isomers in 49% yield as a clear, yellow oil after column chromatography using General Procedure C. E isomer: $^1$H NMR (500 MHz, C$_6$D$_6$) δ 5.61 (dd, J=5.3, 4.7 Hz, 1H), 4.06 (td, J=5.7, 0.8 Hz, 2H), 3.62 (ddd, J=12.1, 10.7, 2.4 Hz, 1H), 3.44 (ddd, J=10.8, 3.9, 2.4 Hz, 1H), 2.78 (dd, J=8.6, 7.1 Hz, 1H), 1.20 (ddt, J=14.4, 6.3, 2.3 Hz, 1H), 1.02 (overlapping signals, 22 H total). $^{13}$C NMR (125 MHz, C$_6$D$_6$) δ 154.6, 127.2, 101.8, 67.9, 60.6, 39.2, 23.7, 17.8, 11.9. HRMS (ESI) m/z calculated for [M–C$_3$H$_7$]$^+$ 268.1364; found 268.1355. Z isomer: $^1$H NMR (500 MHz, C$_6$D$_6$) δ 5.49 (dd, J=7.8, 5.3 Hz, 1H), 5.09 (dd, J=12.5, 8.2 Hz, 1H), 4.76 (dd, J=12.7, 4.9 Hz, 1H), 3.43 (ddd, J=12.8, 10.6, 2.0 Hz, 1H), 3.30 (ddd, J=10.8, 4.0, 2.3 Hz, 1H), 2.46 (dd, J=9.3, 6.3 Hz, 1H), 1.03 (overlapping signals, 21 H total), 0.87 (ddt, J=14.6, 6.0, 2.8 Hz, 1H), 0.63 (m, 1H). $^{13}$C NMR (125 MHz, C$_6$D$_6$) δ 154.1, 126.0, 102.9, 67.7, 59.9, 38.4, 23.2, 18.0, 12.0. HRMS (ESI) m/z calculated for [M–C$_3$H$_7$]$^+$ 268.1364; found 268.1363.

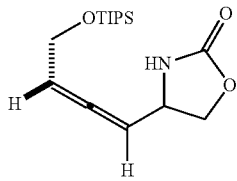

Compound 16b. The C—H amination product was obtained in 17% yield as an inseparable mixture of diastereomers. $^1$H NMR (500 MHz, C$_6$D$_6$) δ 5.72 (s br, 1H), 5.25 (m, 1H), 4.72 (m, 1H), 4.10 (ddd, J=5.5, 2.9, 0.7 Hz, 1H), 4.04 (ddd, J=5.8, 2.9, 1.1 Hz, 1H), 3.74-3.63 (m, 1H), 3.55-3.51 (m, 2H), 1.07 (overlapping signals, 21 H total). $^{13}$C NMR (125 MHz, C$_6$D$_6$) δ 202.7, 202.7, 159.1, 159.1, 95.8, 95.7, 93.2, 93.0, 69.3, 69.1, 60.9, 60.7, 51.4, 51.2, 17.8, 11.9, 11.9. HRMS (ESI) m/z calculated for [M–C$_3$H$_7$]$^+$ 268.1364; found 268.1370.

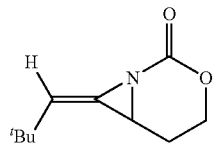 [SMILES: CC(C)(C)/C=C1\C2CCOC(=O)N12]

Compound 17a. The product was obtained as a 2.2:1.0 mixture of E:Z isomers before purification via column chromatography using General Procedure D. After purification, only the E isomer was present in 45% yield as a white solid (m.p. 84-87° C.). $^1$H NMR (500 MHz, C$_6$D$_6$) δ 5.56 (br s, NH), 3.61 (ddd, J=14.1, 11.7, 2.5 Hz, 1H), 3.45 (ddd, J=10.5, 4.0, 2.4 Hz, 1H), 2.65 (dd, J=8.4, 6.3 Hz, 1H), 1.09 (ddt, J=14.5, 6.3, 2.1 Hz, 1H), 0.89 (s, 9H), 0.83-0.76 (m, 1H). $^{13}$C NMR (125 MHz, C$_6$D$_6$) δ 155.1, 124.2, 112.8, 67.8, 39.3, 32.2, 29.6, 24.1. HRMS (ESI) m/z calculated for [M]$^+$ 181.1098, found 181.1106.

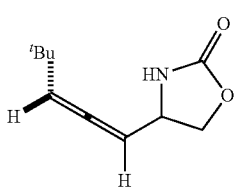

Compound 17b. The CH-amination product was present in 23% yield as an inseparable mixture of diastereomers. $^1$H NMR (500 MHz, C$_6$D$_6$) δ 6.90 (s br, NH), 6.82 (s br, NH), 5.21 (dd, J=6.2, 1.7 Hz, 0.4H), 5.14 (dd, J=7.0, 2.0 Hz, 0.5H), 4.83 (dd, J=5.5, 5.5 Hz, 0.5H), 4.76 (dd, J=6.2, 6.2 Hz, 0.4H), 3.61 (overlapping signals, 3 H total), 0.98 (overlapping signals, 9 H total). $^{13}$C NMR (125 MHz, C$_6$D$_6$) δ 200.7, 200.6, 159.8, 159.8, 106.9, 106.5, 93.5, 93.3, 69.5, 69.3, 51.5, 51.4, 31.7, 31.4, 29.7, 29.6. HRMS (ESI) m/z calculated for [M]$^+$ 181.1098, found 181.1095.

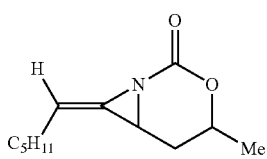

Compound 18a. The product was obtained as a 1.5:1 mixture of E:Z isomers in 48% yield as a thick, colorless oil using General Procedure D. $^1$H NMR (500 MHz, C$_6$D$_6$) δ 5.54 (t, J=6.9 Hz, 0.6H), 5.15 (t, J=7.6 Hz, 0.4H), 3.94 (m, 1H), 2.51-2.77 (m, 2H), 1.94 (app q, J=7.3 Hz, 2H), 1.08-1.36 (m, 7H), 0.86 (t, J=7.1 Hz, 3H), 0.81 (2 doublets, J=6.3, 5.9 Hz, 3H total). $^{13}$C NMR (125 MHz, C$_6$D$_6$) δ 155.5, 155.1, 126.9, 126.5, 102.2, 101.3, 76.2, 75.9, 38.5, 38.4, 31.4, 31.3, 30.7, 30.7, 29.7, 28.8, 28.1, 27.2, 22.5, 22.5, 20.2, 20.1, 13.9, 13.9. HRMS (EI) m/z calculated for [M+H]$^+$ 210.1489, found 210.1482.

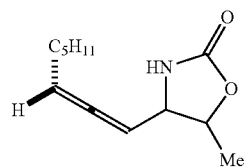

Compound 18b. The product was obtained as an inseparable mixture of stereoisomers (~2:1 approximate dr for C—H amination) in 31% as a thick, colorless oil using General Procedure D. $^1$H NMR (500 MHz, C$_6$D$_6$) δ 7.22 (br s, 1H), 5.16 (m, 1H), 4.84 (m, 0.6H), 4.74 (m, 0.4H), 4.16 (m, 0.4H), 3.99 (m, 0.6H), 3.67 (m, 0.4H), 3.42 (m, 0.6H), 1.87 (m, 2H), 1.17-1.40 (m, 6H), 0.80-0.98 (overlapping doublets and triplets, 6H). $^{13}$C NMR (125 MHz, C$_6$D$_6$) δ 204.2, 203.9, 203.9, 159.7, 159.3, 94.7, 94.5, 94.3, 94.2, 91.1, 91.0, 88.5, 78.5, 75.6, 75.5, 59.2, 59.0, 55.7, 55.3, 31.3, 31.2, 28.6, 28.5, 28.4, 28.3, 22.5, 22.5, 18.8, 18.6, 15.6, 15.5, 13.9, 13.9. HRMS (EI) m/z calculated for [M+Na]$^+$ 232.1308, found 232.1305.

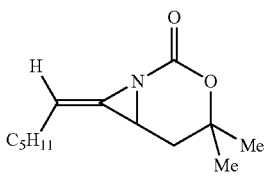

Compound 19a. The product was obtained as an oil in 10% (Condition B) yield as a 2.8:1 mixture of E:Z isomers. Condition D gave a 5% yield of the product as a 1.9:1 mixture of E:Z isomers. $^1$H NMR (500 MHz, $C_6D_6$) δ 5.57 (t, J=6.3 Hz, 1H major), 5.17 (t, J=7.7 Hz, 1H minor), 2.67 (overlapping signals, 2H total), 1.95 (br dd, J=14.0, 7.2 Hz, 2H), 1.17 (overlapping signals, 16H total), 0.89 (overlapping signals, 9H). $^{13}$C NMR (125 MHz, $C_6D_6$) δ 183.6, 155.3, 102.3, 101.4, 83.3, 36.9, 34.0, 31.3, 29.7, 28.7, 28.7, 28.1, 27.2, 26.7, 24.3, 22.5, 22.5, 13.9, 13.9. HRMS (EI) m/z calculated for $[M]^+$ 223.1567, found 223.1563.

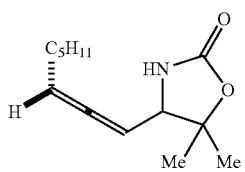

Compound 19b. The product was obtained as a colorless oil that solidified to a waxy solid upon refrigeration in 72% yield using General Procedure B and 84% yield using General Procedure D. $^1$H NMR (500 MHz, $C_6D_6$) δ 7.02 (br s, 1H), 5.12 (m, 1H), 4.74 (m, 1H), 3.50 (m, 1H), 1.84 (m, 2H), 1.22 (m, 6H), 1.01 (four singlets, 6H), 0.84 (two triplets, J=7.2, 6.8 Hz, 3H). $^{13}$C NMR (125 MHz, $C_6D_6$) δ 204.6, 204.4, 159.2, 94.7, 94.2, 89.4, 89.3, 83.0, 82.9, 82.9, 61.9, 61.6, 31.6, 31.5, 28.9, 28.9, 28.7, 28.6, 27.1, 22.9, 22.8, 14.2, 14.2. HRMS (ESI) m/z calculated for $[M]^+$ 223.1567, found 223.1561.

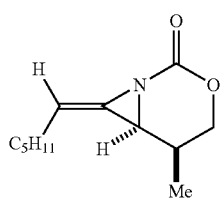

Compound 20a. The product was obtained as an oil in 21% yield as a separable 3:1 mixture of E:Z diastereomers using General Procedure B. Major diastereomer (E): $^1$H NMR (500 MHz, $C_6D_6$) δ 5.55 (t, J=6.8 Hz, 1H), 3.48 (t, J=10.8 Hz, 1H), 3.38 (dd, J=10.4, 3.8 Hz, 1H), 2.40 (d, J=8.1 Hz, 1H), 1.90 (app q, J=7.1 Hz, 2H), 1.07-1.24 (m, 7H), 0.85 (t, J=7.2 Hz, 3H), 0.37 (d, J=6.9 Hz, 3H). $^{13}$C NMR (125 MHz, $C_6D_6$) δ 155.4, 126.2, 101.9, 73.7, 44.4, 31.6, 30.5, 28.9, 28.5, 22.8, 14.1, 13.1. HRMS (ESI) m/z calculated for $[M]^+$ 209.1411, found 209.1402. Minor diastereomer (Z): $^1$H NMR (500 MHz, $C_6D_6$) δ 5.55 (t, J=7.2 Hz, 1H), 3.76 (dd, J=10.6, 2.5 Hz, 1H), 3.34 (dd, J=10.8, 3.0 Hz, 1H), 2.85 (d, J=6.6 Hz, 1H), 1.85 (m, 2H), 1.44 (m, 1H), 1.16 (m, 1H), 0.85 (t, J=7.1 Hz, 3H), 0.48 (d, J=7.4 Hz, 3H). $^{13}$C NMR (125 MHz, $C_6D_6$) δ 155.2, 123.6, 103.7, 72.4, 43.7, 31.6, 29.4, 28.8, 25.3, 22.7, 14.1, 12.6. HRMS (ESI) m/z calculated for $[M]^+$ 209.1411, found 209.1417.

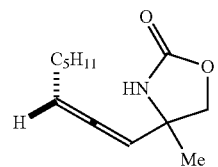

Compound 20b. The product was obtained as an oil in 48% yield. $^1$H NMR (500 MHz, $C_6D_6$) δ 7.35 (br s, 1H), 7.28 (br s, 1H), 5.19 (m, 1H), 5.03 (m, 1H), 3.88 (m, 1H), 3.55 (br d, J=8.8 Hz, 1H), 1.88 (m, 2H), 1.25 (overlapping signals, 6H), 1.06 (br s, 3H), 0.90 (m, 3H). $^{13}$C NMR (125 MHz, $C_6D_6$) δ 201.8, 159.4, 96.7, 96.6, 95.9, 95.7, 75.4, 56.6, 31.3, 28.6, 28.5, 25.3, 25.2, 22.5, 13.9. HRMS (EI) m/z calculated for $[M+H]^+$ 210.1489, found 210.1495.

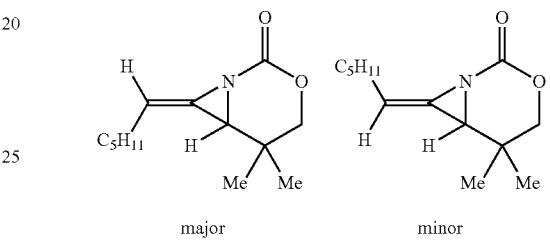

major       minor

Compound 21a. The desired product was obtained in 94% yield with less than 5% of the starting material remaining. The product was a 3:1 mixture of E:Z isomers, where the major isomer has the bulky alkyl chain on the olefin directed towards from the gem dimethyl group of the ring, according to NOESY 1D experiments on both isomers. Major isomer: $^1$H NMR (500 MHz, $CDCl_3$) δ 5.61 (t of d, 1H, J=7.3, 0.9 Hz), 4.23 (d, 1H, J=10.5 Hz), 3.81 (d, 1H, J=9.8 Hz), 3.72 (s, 1H), 2.11 (dd, 2H, J=14.1, 7.1 Hz), 1.54 (m, 2H), 1.42-1.29 (br m, 7H total), 0.87 (2 overlapping signals, 6H total). $^{13}$C NMR (125 MHz, $CDCl_3$) δ 156.2, 123.2, 104.2, 77.8, 48.6, 31.3, 29.5, 28.9, 28.6, 23.9, 22.4, 20.6, 13.9. HRMS (ESI) m/z calculated for $[M+H]^+$ 224.1646, found, 224.1652. Minor isomer: $^1$H NMR (500 MHz, $CDCl_3$) δ 5.32 (dd, 1H, J=7.4, 5.3 Hz), 4.16 (d, 1H, J=10.3 Hz), 3.80 (d, 1H, J=10.7 Hz), 3.08 (s, 1H), 2.39 (dd, 2H, J=14.6, 6.9 Hz), 1.42-1.21 (overlapping signals, 9H total), 0.87 (2 overlapping signals, 6H total). $^{13}$C NMR (125 MHz, $CDCl_3$) δ 155.5, 122.9, 105.2, 77.1, 48.8, 31.2, 29.4, 29.0, 27.3, 23.9, 22.4, 20.6, 14.0. HRMS (ESI) m/z calculated for $[M+Na]^+$ 246.1465, found 246.1467.

V. Ring-Opening of Methylene Aziridines.

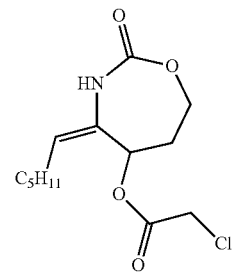

Compound 22. A solution of the E bicyclic methylene aziridine 14a (99.9 mg, 0.512 mmol, 1.0 equiv) dissolved in 4 mL of CH$_2$Cl$_2$ was cooled to 0° C. Chloroacetic acid (159.9 mg, 1.7 mmol, 3.3 equiv) dissolved in 2 mL of CH$_2$Cl$_2$ was slowly added to the reaction and the mixture allowed to warm to rt overnight. The mixture was concentrated under reduced pressure and purified by removing the excess chloroacetic acid under high vacuum (~0.1 mmHg) to give the product 22 in 99% yield. $^1$H NMR (500 MHz, C$_6$D$_6$) δ 8.39 (NH), 5.76 (d, J=5.8 Hz, 1H), 5.07 (t, J=7.5 Hz, 1H), 3.72 (td, J=12.6, 3.9 Hz, 1H), 3.55-3.51 (m, 1H), 3.43 (d, J=2.3 Hz, 2H), 1.93-1.69 (m, 3H), 1.23-1.09 (m, 7H), 0.87 (t, J=6.8 Hz, 3H). $^{13}$C NMR (125 MHz, C$_6$D$_6$) δ 165.7, 156.3, 130.46, 118.0, 68.4, 65.1, 40.3, 32.7, 31.3, 29.3, 26.4, 22.5, 13.9. HRMS (ESI) m/z calculated for C$_{13}$H$_{20}$ClNO$_4$ [M+H$^+$] 1290.1154, found 290.1155.

Compound 23 (see also Bergmeier and Stanchina, *J. Org. Chem.* 1997, 62, 4449). Sodium azide (40.1 mg, 0.62 mmol, 1.5 equiv) was dissolved in 1.5 mL of dry DMF and cooled to 0° C. Chlorotrimethylsilane (81 μL, 0.63 mmol, 1.5 equiv) was added to the solution over the course of 10 min and left to stir for 30 min at 0° C. The reaction mixture was allowed to warm to rt and stirred for an additional 30 min and the E bicyclic methylene aziridine 14a (81.9 mg, 0.42 mmol, 1.0 equiv) dissolved in 1.0 mL of DMF was added was added and the reaction mixture stirred overnight. After a total reaction time of 18 h, the reaction mixture was passed through a plug of silica gel pretreated with 0.5% triethylamine, concentrated under reduced pressure, and purified via column chromatography (9:1 hexanes/ethyl acetate-ethyl acetate) through silica gel pre-treated with 0.5% triethylamine to afford 23 as a clear, colorless oil in 82% yield. $^1$H NMR (500 MHz, C$_6$D$_6$) δ 6.69 (NH), 4.33 (dd, J=4.1, 1.6 Hz, 1H), 3.64 (t, J=5.7 Hz, 2H), 3.26 (t, J=7.2 Hz, 1H), 1.71-1.68 (m, 2H), 1.27-1.03 (m, 8H), 0.84 (t, J=7.4 Hz, 3H). $^{13}$C NMR: (125 MHz, C$_6$D$_6$) δ 158.1, 132.8, 106.5, 66.8, 66.6, 32.3, 31.2, 28.4, 25.7, 22.5, 13.8. HRMS (ESI) m/z calculated for C$_{11}$H$_{18}$N$_4$O$_2$ [M+H$^+$] 261.1322, found 261.1317.

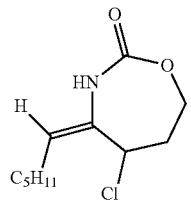

Compound 24 (see also Bergmeier and Stanchina, *J. Org. Chem.* 1997, 62, 4449). To a solution of freshly distilled chlorotrimethylsilane (50 μL, 0.04 mmol, 1.5 equiv) in 1.5 mL THF cooled to −40° C. was added E bicyclic methylene aziridine 14a (51.2 mg, 0.26 mmol, 1.0 equiv) in 1.5 mL of THF. The temperature was maintained for 2 h, then the reaction mixture warmed to 0° C. for an additional 4 h until complete consumption of the starting material was observed by TLC. The reaction mixture was concentrated under reduced pressure and purified via flash column chromatography (9:1 hexanes/ethyl acetate-3:1 hexanes/ethyl acetate) through silica gel pre-treated with 0.5% triethylamine to obtain 24 as a clear colorless oil in 61% yield. $^1$H NMR (500 MHz, C$_6$D$_6$) δ 7.74 (NH), 4.88 (t, J=7.3 Hz, 1H), 4.69 (dd, J=5.0, 3.2 Hz, 1H), 3.88 (ddd, J=12.7, 6.9, 2.9 Hz, 1H), 3.57 (ddd, J=12.7, 7.9, 3.1 Hz, 1H), 1.75-1.69 (ddt, J=15.5, 7.6, 2.8 Hz, 1H), 1.60-1.52 (m, 2H), 1.45-1.39 (m, 1H), 1.18-1.13 (m, 2H), 1.07-1.02 (m, 4H), 0.85 (t, J=7.2 Hz, 3H). $^{13}$C NMR (125 MHz, C$_6$D$_6$) δ 156.6, 132.7, 121.1, 64.3, 52.8, 36.3, 31.1, 28.9, 26.6, 22.4, 13.8. HRMS (ESI) m/z calculated for C$_{11}$H$_{18}$ClNO$_2$ [M+H$^+$] 232.1099, found 232.1110.

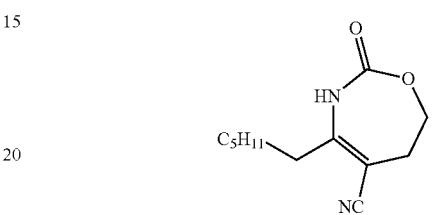

Compound 25 (see also Duran et al., *J. Org. Chem.* 2005, 70, 8616). A solution of the E bicyclic methylene aziridine 14a (61.3 mg, 0.31 mmol, 1.0 equiv) dissolved in 3 mL of DMF was cooled to 0° C. and treated with KCN (27.1 mg, 0.42 mmol, 1.3 equiv) in one portion. The reaction mixture was warmed to 10-20° C. for 2 h, then allowed to warm to rt. Additional KCN (70.0 mg, 1.1 mmol, 3.5 equiv) was added to the reaction mixture, followed by Sc(OTf)$_3$ (26.4 mg, 0.064 mmol, 0.2 equiv) in one portion. The reaction mixture was monitored by TLC and stirred overnight at rt. After a total reaction time of 26 h, the mixture was concentrated under reduced pressure and purified via flash column chromatography (9:1 hexanes/ethyl acetate-1:1 hexanes/ethyl acetate) through silica gel pre-treated with 0.5% triethylamine to obtain 25 as a white solid (melting point: 100° C.-103° C.) in 60% yield. $^1$H NMR (500 MHz, C$_6$D$_6$) δ 7.50 (NH), 3.28 (dd, J=6.0, 4.7 Hz, 2H), 2.12 (t, J=7.6 Hz, 2H), 1.72 (t, J=4.8 Hz, 2H), 1.36-1.16 (m, 8H), 0.88 (t, J=7.5 Hz, 3H). $^{13}$C NMR (125 MHz, C$_6$D$_6$) δ 155.6, 149.0, 118.8, 89.5, 65.6, 36.0, 31.3, 30.7, 28.4, 28.0, 22.5, 13.9. HRMS (ESI) m/z calculated for C$_{12}$H$_{18}$N$_2$O$_2$ [M+H$^+$] 223.1442, found 223.1432.

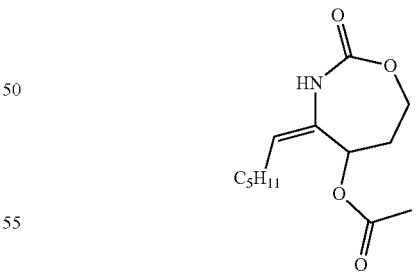

Compound 26 (see also Bergmeier and Stanchina, *J. Org. Chem.* 1997, 62, 4449). A solution of the E bicyclic methylene aziridine 14a (25.0 mg, 0.128 mmol, 1.0 equiv) dissolved in 0.8 mL of dioxane was treated with glacial acetic acid (320 μL, 5.57 mmol, 44.0 equiv). The reaction mixture was stirred at rt for 36 hours, concentrated under reduced pressure and purified by removal of the excess acetic acid under high vacuum (~0.1 mmHg) to yield 26 in 99% yield. $^1$H NMR (500 MHz, C$_6$D$_6$) δ 8.64 (NH) 5.88 (d, J=6.3 Hz, 1H), 5.12 (t, J=7.7 Hz, 1H), 3.79 (td, J=12.5, 4.0 Hz, 1H), 3.58 (ddd, J=13.1, 5.0, 2.6 Hz, 1H), 1.98-1.80 (m, 3H), 1.65 (s, 3H), 1.30-1.09 (m, 7H), 0.86 (t, J=7.6 Hz, 3H). $^{13}$C NMR (125 MHz, C$_6$D$_6$) δ 169.0, 156.4, 131.5, 116.9, 66.7, 65.3, 33.0, 31.3, 29.4, 26.4, 22.5, 20.2, 13.9. HRMS (ESI) m/z calculated for C$_{13}$H$_{21}$NO$_4$ [M+H$^+$] 256.1544, found 256.1547.

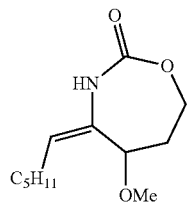

Compound 27. A solution of the E bicyclic methylene aziridine 14a (84.1 mg, 0.431 mmol, 1.0 equiv) in 20 mL MeOH was treated with a single portion of Sc(OTf)$_3$ (22.8 mg, 0.0463 mmol, 0.11 equiv). The reaction mixture was monitored by TLC until complete, then concentrated under reduced pressure and purified via flash column chromatography (9:1 hexanes/ethyl acetate-1:1 hexanes/ethyl acetate) through silica gel pre-treated with 0.5% triethylamine to obtain 27 in 42% yield as a single diastereomer. $^1$H NMR (500 MHz, C$_6$D$_6$) δ 8.67 (NH), 5.20 (t, J=7.1 Hz, 1H), 4.07 (d, J=7.1 Hz, 1H), 3.89 (td, J=12.0, 3.6 Hz, 1H), 3.68 (ddd, J=12.0, 5.7, 2.3 Hz, 1H), 3.05 (s, 3H), 2.03-1.96 (m, 1H), 1.72-1.64 (m, 2H), 1.25-1.07 (m, 7H), 0.87 (t, J=6.2 Hz, 3H). $^{13}$C NMR (125 MHz, C$_6$D$_6$) δ 156.8, 132.9, 117.1, 73.5, 65.3, 55.4, 34.1, 31.3, 29.6, 26.1, 22.5, 13.9. HRMS (ESI) m/z calculated for C$_{12}$H$_{21}$NO$_3$ [M+H$^+$] 1228.1595, found 228.1607.

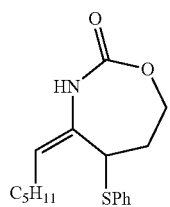

Compound 28. A solution of the E bicyclic methylene aziridine 14a (76.2 mg, 0.4 mmol, 1.0 equiv) in 4.5 mL CH$_2$Cl$_2$ was treated with thiophenol (70.0 μL, 0.7 mmol, 1.75 equiv) at rt. The reaction mixture was stirred for 5 min, then treated with a single portion of Sc(OTf)$_3$ (19.2 mg, 0.04 mmol, 0.10 equiv). The reaction mixture was monitored by TLC until complete consumption of starting material, then concentrated under reduced pressure and purified via flash column chromatography (9:1 hexanes/ethyl acetate-1:1 hexanes/ethyl acetate) through silica gel pre-treated with 0.5% triethylamine to obtain 28 as a colorless oil in 46% yield as a single diastereomer. $^1$H NMR (500 MHz, C$_6$D$_6$) δ 7.40 (d, J=7.7 Hz, 2H, Ar), 7.01-6.94 (m, 3H, Ar), 6.97 (NH), 4.13 (t, J=4.0 Hz, 1H), 3.70-3.58 (m, 2H), 3.34 (dd, J=8.3, 7.3 Hz, 1H), 1.61-1.57 (m, 2H), 1.49 (quint, J=7.4 Hz, 2H), 1.29-1.08 (m, 6H), 0.85 (t, J=7.0 Hz, 3H). $^{13}$C NMR (125 MHz, C$_6$D$_6$) δ 157.5, 134.0, 133.4, 132.7, 128.7, 128.0, 106.7, 66.4, 56.2, 32.3, 31.2, 28.5, 27.2, 22.4, 13.9. HRMS (ESI) m/z calculated for C$_{17}$H$_{23}$NO$_2$S [M+H$^+$] 306.1523, found 306.1515.

VI. Reactions to Functionalize all Three Allene Carbons with Heteroatoms.

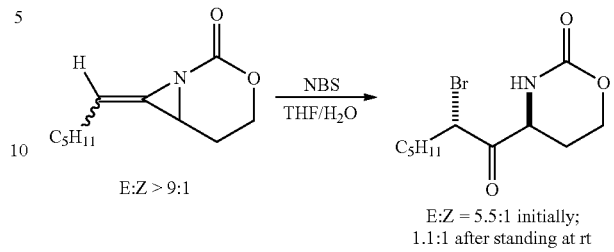

Compound 29. To a solution of ice-cooled methylene aziridine 14a (72.1 mg, 0.37 mmol) in 6 mL of a 1:1 THF/H$_2$O mixture was added N-bromosuccinimide (72.3 mg, 0.41 mmol) in one portion. The reaction mixture was warmed slowly to rt and monitored by TLC until complete consumption of starting material was observed. The reaction mixture was dried over Na$_2$SO$_4$ and the volatiles removed under reduced pressure. The residue was taken up in dichloromethane, washed three times with H$_2$O, dried over Na$_2$SO$_4$ and the solvent removed under reduced pressure. The residue was purified by column chromatography (1:1 hexanes/EtOAc) to obtain 29 as a white solid in 59% yield as a 5.5:1 mixture of diastereomers, which slowly equilibrated in solution to give a 1.1:1 mixture of diastereomers. $^1$H NMR (500 MHz, C$_6$D$_6$) δ 7.47 (s, br, 2.1 H), 4.40 (isomer A, dd, J=7.1, 7.1 Hz, 1 H), 4.31 (isomer B, t, J=7.3, 7.3 Hz, 1.1 H), 3.77 (isomer A, ddd, J=5.6, 5.6, 3.2 Hz, 1 H), 3.75-3.66 (isomer A+B, m, 2.1 H), 3.64 (isomer B, ddd, J=6.1, 6.1, 2.4 Hz, 1.1 H), 3.46 (isomer A, ddd, J=10.3, 6.4, 4.2 Hz, 1 H), 3.40 (isomer B, ddd, J=10.8, 7.1, 4.2 Hz, 1.1 H), 1.98-1.77 (isomer A+isomer B, m, 4.4 H), 1.64-1.55 (isomer A+isomer B, m, 1.2 H), 1.43-1.03 (isomer A+isomer B, m, 18.8 H), 0.84 (isomer A+isomer B, t, J=6.9 Hz, 6.3 H). $^{13}$C NMR (500 MHz, C$_6$D$_6$) δ 201.4, 200.8, 154.2, 154.1, 64.8, 64.5, 56.9, 56.1, 49.7, 48.4, 33.6, 33.5, 31.8, 31.7, 27.5 (2 carbons), 23.7, 23.6, 23.1 (2 carbons), 14.5 (2 carbons). m.p. 99-101° C. HRMS (ESI) m/z calculated for C$_{11}$H$_{18}$BrNO$_3$ [M+H$^+$] 292.0543, found 292.0548.

Stereochemical Rationale for the Initial Major Diastereomer: One major diastereomer is produced in this reaction, but a mixture is obtained upon standing. This is not particularly surprising, as the asymmetric center of α-bromoketones is known to be quite labile. The initial preponderance of one diastereomer suggests that further studies to understand the factors controlling the stereochemistry will lead to synthetically useful reactions. A proposed mechanism involves the formation of the bromonium ion predominately on one face of the olefin of the methylene aziridine. It is unlikely that a purely S$_N$2 attack would occur at the spiro carbon, but formation of the hemiaminal is certainly plausible. Facile formation of the ketone would open the aziridine ring and generate the observed product. Future studies are underway to confirm this proposed mechanism.

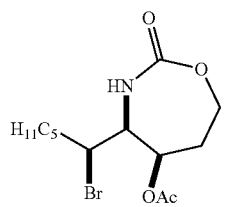

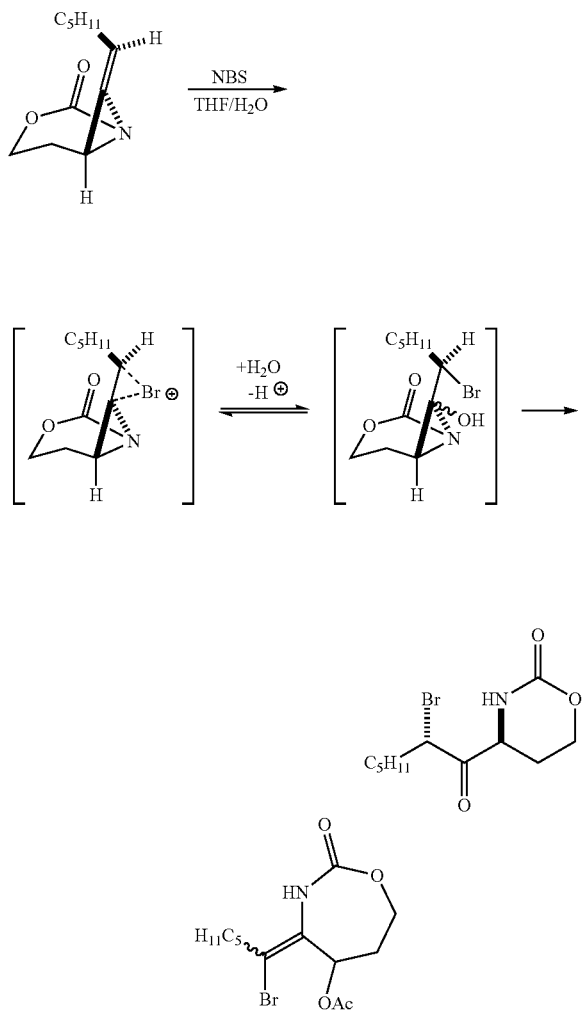

Compound 30. To a solution of the E enecarbamate 26 (30.1 mg, 0.12 mmol, 1.0 equiv) dissolved in 1.0 mL THF and 1.0 mL H$_2$O cooled to 0° C. was added N-bromosuccinimide (29.0 mg, 0.163 mmol, 1.4 equiv) in one portion. The reaction mixture was warmed slowly to rt and monitored by TLC until complete consumption of starting material was observed. The reaction mixture was extracted with three portions of ethyl acetate, washed with brine, dried over magnesium sulfate, and concentrated under reduced pressure. The reside was purified via flash column chromatography (9:1 hexanes/ethyl acetate to ethyl acetate) pre-treated with 0.5% triethylamine to afford 30 in 68% yield as a 2.3:1 mixture of E:Z isomers (Isomer A=E; Isomer B=Z). $^1$H NMR (500 MHz, C$_6$D$_6$) δ 8.14 (Isomer A, NH), 6.66 (Isomer B, NH), 6.25 (Isomer A, d, J=6.2 Hz, 1H), 5.77 (Isomer B, d, J=6.9 Hz, 0.4H), 3.75 (Isomer A, td, J=12.4, 4.1 Hz, 1H), 3.57 (Isomer B, td, J=12.9, 4.1 Hz, 0.4H), 3.48-3.41 (Isomer A+B, m, 1.5H), 2.54-2.48 (Isomer A, m, 1.0H), 2.44-2.37 (Isomer A+B, m, 1.4H), 2.31-2.26 (Isomer B, m, 0.4H), 1.81-1.60 (Isomer A+B, m, 6H), 1.56-1.46 (Isomer A+B, m, 3H), 1.41-1.33 (Isomer A+B, m, 2H), 1.29-0.95 (Isomer A+B, m, 8H), 0.87 (Isomer A, t, J=6.7 Hz, 3H), 0.83 (Isomer B, t, J=7.4 Hz, 1.5H). $^{13}$C NMR (125 MHz, C$_6$D$_6$) δ 168.9, 168.7, 155.4, 153.6, 130.2, 116.0, 112.3, 72.1, 66.9, 65.3, 64.9, 35.7, 35.1, 32.8, 31.8, 30.7, 30.6, 28.4, 27.5, 22.4, 22.4, 20.1, 19.9, 13.8, 13.8. HRMS (ESI) m/z calculated for C$_{13}$H$_{20}$NO$_4$Br [M+H$^+$] 334.0649, found 334.0657.

Compound 31. A solution of the E enecarbamate 26 (65.5 mg, 0.257 mmol, 1.0 equiv) dissolved in 2.0 mL THF and 2.0 mL H$_2$O was cooled to 0° C. N-bromosuccinimide (53.8 mg, 0.302 mmol, 1.2 equiv) was added in one portion. After 5 min, NaBH$_3$CN (64.1 mg, 1.02 mmol, 4.0 equiv) was added, followed by acetic acid (400 µL, 7.0 mmol, 23 equiv) and the reaction mixture was allowed to warm to rt. The reaction was monitored by TLC until complete consumption of the starting material was observed (2 h). The reaction mixture was extracted with three portions of ethyl acetate, washed with brine, dried over magnesium sulfate, and concentrated under reduced pressure. The reside was purified via flash column chromatography (4:1 hexanes/ethyl acetate to ethyl acetate) pre-treated with 0.5% triethylamine to afford 31 as a clear, colorless oil in 73% yield as approximately a 10:1 mixture of diastereomers. $^1$H NMR (500 MHz, C$_6$D$_6$) δ 5.43 (d, J=2.5 Hz, NH), 4.93 (dd, J=3.7, 3.4 Hz, 1H), 3.82 (ddd, J=12.5, 7.7, 5.6 Hz, 1H), 3.61 (ddd, J=8.7, 6.4, 4.4 Hz, 1H), 3.52 (app dt, J=13.1, 4.1 Hz, 1H), 3.16 (dd, J=6.2, 3.9 Hz, 1H), 1.63 (s, 3H), 1.17 (m, 10H), 0.84 (t, J=8.4 Hz, 3H); $^{13}$C NMR (125 MHz, C$_6$D$_6$) δ 168.8, 157.9, 66.5, 63.3, 58.6, 56.3, 34.9, 33.4, 30.5, 26.6, 22.1, 20.0, 13.5. HRMS (ESI) m/z calculated for C$_{13}$H$_{22}$NO$_4$Br [M+Na]$^+$ 358.0625, found 358.0609.

Stereochemical Rationale for the Major Product: Although the stereochemical relationship amongst all three heteroatom-bearing carbons has not been conclusively proven by X-ray crystallography, the identity of the major diastereomer is rationalized by the following observations. First, the major diastereomer appears to have a syn relationship between the carbamate and acetate groups. A coupling constant between the two protons a and b of about 4 Hz suggests a dihedral angle of 70° or 110° according to the Karplus equation. The high diastereoselectivity observed when an acetate group is present suggests the likelihood of anchimeric assistance. One proposed mechanism, as illustrated below, involves shielding of one of the faces of the enecarbamate by the acetate group. This may be due to a number of factors, including conformational stability, intramolecular hydrogen-bonding or electrostatic interactions. Nonetheless, formation of the intermediate bromonium ion then occurs on the opposite face of the double bond from the acetate group. Acetate-assisted opening of the bromonium ion, followed by stereoselective reduction, yields 31. There are several other possibilities, yet these would also be likely to give rise to the same relative stereochemistry. Studies are underway to obtain an improved understanding of the factors that control this highly stereoselective reaction.

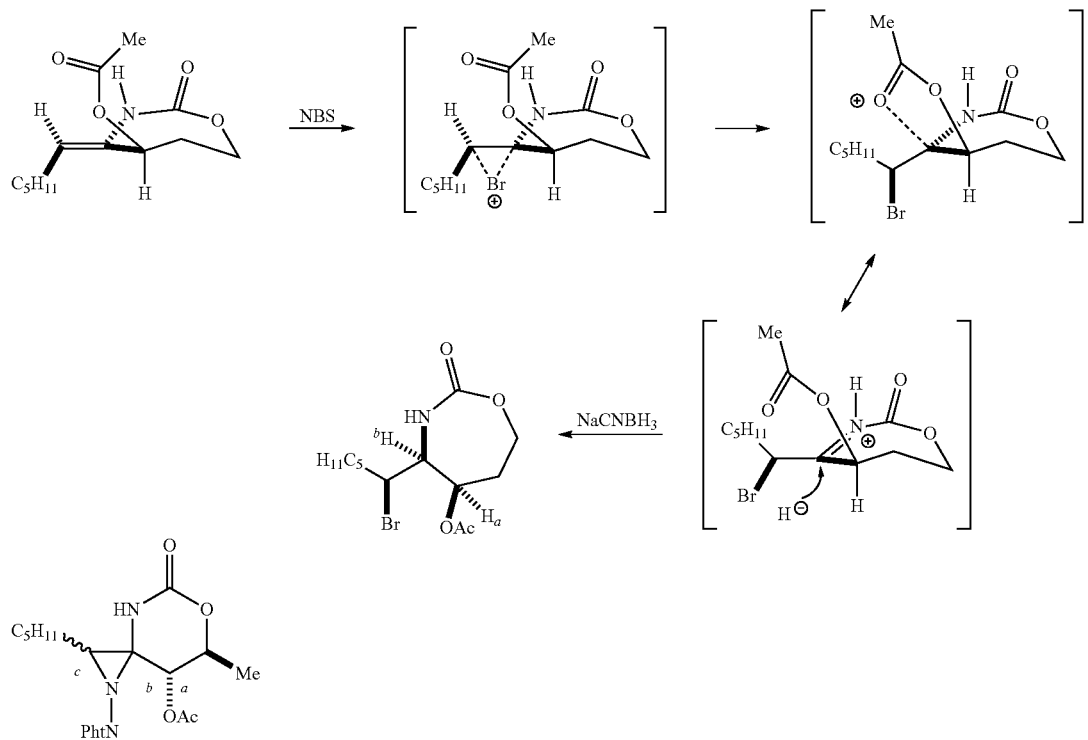

Compound 32 (General Procedure). The allenic carbamate 13 (1.00 mmol, 1.0 equiv) and 10 mL of dry $CH_2Cl_2$ were added to a dry 50 mL Schlenk flask. The solution was kept under an atmosphere of nitrogen and charged with MgO (2.60 mmol, 2.6 equiv) and $Rh_2esp_2$ (0.0250 mmol, 0.025 equiv). The resulting blue-green mixture was stirred for 10 min at rt, then $PhI(OPiv)_2$ or $PhI(OAc)_2$ (1.00 mmol, 1.0 equiv) was added and the flask was fitted with a reflux condenser and heated to 35° C. in an oil bath for 1 h. Two additional portions of oxidant (2×0.51 mmol, 1.02 equiv) were added at 1 h intervals. The reaction was monitored by TLC until it was complete, then cooled to 0° C. in an ice bath. A portion of N-aminophthalimide (1.5 mmol, 1.5 equiv) and dry potassium carbonate (3.5 mmol, 3.5 equiv), followed by additional $PhI(OAc)_2$ (1.6 mmol, 1.6 equiv) were added and the resulting light yellow slurry allowed to warm slowly to rt. The reaction was monitored by TLC and additional portions of $PhtNNH_2$ and $PhI(OAc)_2$ were added as necessary to complete the reaction. A non-aqueous workup was preferred, but the products from the tandem reactions were less sensitive to water than the MAs. The dichloromethane was removed under reduced pressure on a vacuum line, the residue diluted with dry $Et_2O$ and the organics decanted. The residual salts were washed two more times with $Et_2O$ and the volatiles removed under reduced pressure on a vacuum line. A silica gel column was packed using 99.5:0.5 hexanes/triethylamine, followed by flushing with four column volumes of hexanes prior to loading the sample onto the column. The residue was loaded onto the column and initially eluted using a hexanes/ethyl acetate gradient. Depending on the polarity of the products, 5-10% methanol was added to the eluant towards the end of the column to remove any highly polar materials. Phenyl iodide eluted first from the column, followed by unreacted MA (if present), N-aminophthalimide/hydrolysis products and finally the products of nucleophilic ring-opening of the intermediate MA. The product was obtained in 46% yield as approximately a 2.4:1 ratio of diastereomers. Major diastereomer: $^1$H NMR (300 MHz, $CDCl_3$) δ 7.88-7.63 (Ar, 4H), 6.68 (br s, 1H), 4.78 (m, 1H), 4.15 (dd, 1H, J=9.6, 4.2 Hz), 3.70 (d, 1H, J=6.6 Hz), 1.89 (s, 3H), 1.51 (d, 3H, J=7.0 Hz), 1.81-1.2 (several signals, 8H), 0.90 (t, 3H, J=6.5 Hz). Minor diastereomer: $^1$H NMR (300 MHz, $CDCl_3$) δ 7.88-7.63 (Ar, 4H), 6.37 (br s, 1H), 4.78 (m, 1H), 3.63 (br dd, 1H, J=6.6, 6.0 Hz), 3.47 (d, 1H, J=3.3 Hz), 1.95 (s, 3H), 1.43 (d, 3H, J=6.0 Hz), 1.81-1.21 (several signals, 8H), 0.90 (t, 3H, J=6.5 Hz). Both diastereomers: $^{13}$C NMR (75 MHz, $CDCl_3$) δ 170.1, 168.5, 165.7, 160.0, 158.9, 134.6, 134.5, 134.3, 134.2, 129.9, 123.7, 123.6, 123.5, 123.2, 76.4, 74.8, 74.6, 74.3, 73.6, 62.2, 61.3, 53.1, 31.6, 31.5, 29.7, 29.4, 28.9, 26.1, 26.0, 22.4, 21.3, 20.7, 20.6, 14.9, 14.0. HRMS (ESI) m/z calculated for $[M+Na]^+$ 438.1636, found 438.1623.

Example 2

Stereocontrolled N,N-Aminal Synthesis Via Allene Oxidation

Chiral N,N-aminals are structural motifs found in a number of biologically active natural products and pharmaceuticals that exhibit promising anti-cancer, anti-inflammatory, anti-plasmodial and anticholinesterase activities. Among the molecules containing this functionality are the pyrroloindoline alkaloids, the phakellin-type pyrrole-imidazole alkaloids, the lycoposerramines, as well as the challenging synthetic targets (+)-haplophytine and stemoxazolidinone F.

The most straight-forward method to access N,N-aminals involves treatment of a ketone or an aldehyde with an excess of amine in the presence of an acid catalyst. Enamine formation is a competing process when an α hydrogen is present, however the stereochemical outcome of the reaction is difficult to control. These issues can sometimes be circumvented by the diastereoselective intramolecular addition of a tethered amine to a pre-formed iminium ion (eq. 1), a process that has been showcased in a number of indole alkaloid natural product syntheses. The asymmetric preparation of N,N-aminals from an unsaturated substrate such as a tryptamine derivative (eq. 2) is much more challenging, as protonation serves as the enantiodetermining step. Intermolecular preparations of enantioenriched N,N-aminals are also limited, although Antilla and co-workers (*Chem. Commun.* 2007, 4477-4479) have reported the asymmetric addition of nitrogen nucleophiles to imines using a VAPOL phosphoric acid catalyst (eq. 3).

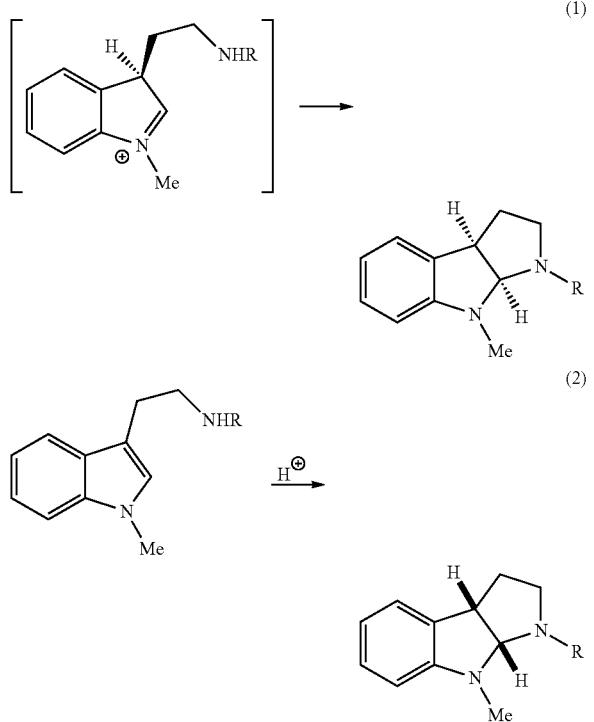

The development of new methods for the rapid and stereoselective introduction of multiple heteroatoms into readily available synthetic intermediates is important for drug discovery and for improving current synthetic routes to known therapeutic agents. Compared to state-of-the-art olefin oxidations, use of allene substrates offers several advantages, including the ability to form three new carbon-heteroatom bonds in a single flask, increased flexibility in the choice of heteroatoms employed and the capability of transferring a single element of axial chirality to three new stereodefined sp³ carbon-heteroatom bonds. This example describes the diastereoselective bis-aziridination of allenes to strained 1,4-diazaspiro[2.2]pentanes (DASPs) and the transformation of these reactive intermediates to chiral N,N-aminals, resulting in the formation of four new carbon-heteroatom bonds in a single reaction flask. The axial chirality of the allene can be transferred to all four new C—X bonds in the N,N-aminal product, where X is a heteroatom, with good fidelity (eq. 4).

(4)

N,N-aminals from allenes

To gain a better understanding of the unexplored chemical behavior of potentially highly reactive 1,4-diazaspiro[2.2] pentanes, the scope of intermolecular bis-aziridination of allenes was briefly examined. Treatment of 5 with PhthNNH$_2$ in the presence of PhI(OAc)$_2$ as the oxidant gave a 59% yield of the desired DASP 5a as one major diastereomer (Table 2-1, entry 1). Pyramidal inversion of the aziridine nitrogens of 5a gave rise to a mixture of three invertomers in a 100:21:11 ratio. Dynamic NMR experiments showed that only a single compound was present at rt, although a coalescence temperature could not be reached before the DASP underwent thermal rearrangement. The phthalimido group of the terminal aziridine and the ester maintain a cis relationship in the solid state, as demonstrated by an X-ray crystal structure of 3a (see the Experimental Details section below for additional information).

TABLE 2-1

Intermolecular DASP synthesis.

| entry | | $R^1, R^2, R^3$ | yield | dr |
|---|---|---|---|---|
| 1 | 5 | H, Me, CO$_2$Et | 59%[a] 5a | >9:1 |
| 2 | 6a | C$_5$H$_{11}$, H, (CH$_2$)$_2$OTBS | 65% 7a | 1:1 |

TABLE 2-1-continued

| 3 | 6b | $C_5H_{11}$, H, $CH_2CO_2Et$ | 73% 7b | 1.6:1 |
| 4 | 6c | $C_5H_{11}$, H, $C(Me)_2CO_2Et$ | 51% 7c, 19% 8c | 1.3:1 |
| 5 | 6d | $C_4H_9$, H, $C_4H_9$ | 46% 7d, 7% 8d | >9:1 |
| 6 | 6e | Me, Me, $CO_2Et$ | 62% 7e | 1:1 |
| 7 | 6f | Me, Me, Me, Me | 0% | — |

[a]One major diastereomer as a mixture of invertomers.

The remaining examples in Table 2-1 summarize the effect of allene substitution on the yield and diastereoselectivity of DASP formation. In general, 1,3-disubstituted allene substrates (entries 2-5) gave moderate yields of the corresponding DASPs as mixtures of diastereomers, as opposed to the invertomers seen for terminal allene precursors such as 5 (entry 1). Slightly better selectivity was seen when a $CO_2Et$ group was attached to the carbon α to the allene (entries 3-4), perhaps due to secondary interactions of the ester with one of the NPhth groups or better regioselectively in the first allene aziridination. An increase in the steric bulk around the allene 6c (entry 4) also resulted in a 19% recovery of the intermediate MA 8c as a mixture of regioisomers. Eliminating a stereochemical element through the use of a symmetric 1,3-disubstituted allene 6d (entry 5) yielded only one major DASP diastereomer 7d. The reaction of a 1,1',3-trisubstituted allene (entry 6) gave a 62% yield of 7e as a 1:1 mixture of diastereomers. An attempt to use a tetrasubstituted allene 6f met with no success.

Differentiation in the electronics of the two DASP aziridines was difficult to achieve using a purely intermolecular aziridination of the allene substrate. The intermediate methylene aziridine was even more reactive than the allene and significant amounts of DASPs were formed. Thus, to further develop this chemistry and control the subsequent reactivity of DASPs, the electronic differentiation of the two aziridine rings using an intra/intermolecular bis-aziridination approach was explored. The syntheses and preliminary reactivities of an unusual class of compounds, the bicyclic methylene aziridines (MAs), obtained from the Rh-catalyzed intramolecular aminations of allenes (Scheme 2-1, 1 to 2) is described above in Example 1.

Treatment of 2 with N-aminophthalimide ($PhtNNH_2$) as a second nitrene precursor would be expected to form a highly strained and reactive 1,4-diazaspiro[2.2]pentane 3 (Atkinson and Malpass, *Tetrahedron Lett.* 1975, 48, 4305-4306). In contrast to traditional methods for N,N-aminal formation, the key intermediate 3 allows for the introduction of additional functionality into the molecule via aziridine ring-opening. The differentiation in the ring strain and electronic environment of the two aziridines of 3 would be expected to promote regioselective nucleophilic ring-opening of the more strained aziridine to yield the N,N-aminal 4.

A carbamate group was utilized as a robust and atom-economical nitrogen protecting group for the first ring formed through intramolecular allene aziridination. The resulting [6,3]-bicyclic MAs were then treated with $PhtNNH_2$ in the presence of PhIO to form the corresponding DASPs in moderate to good yields (Table 2-2).

TABLE 2-2

The preparation of electronically differentiated 1,4-diazaspiro[2.2]pentane aminals.

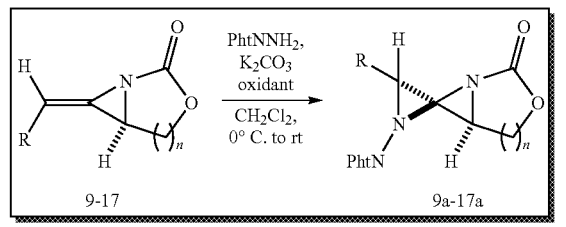

9-17 → 9a-17a

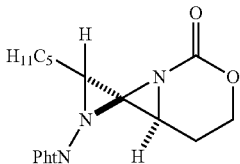

58% (65%)[a] 9a      (1)

Scheme 2-1. N,N-aminals via allene bis-aziridination.

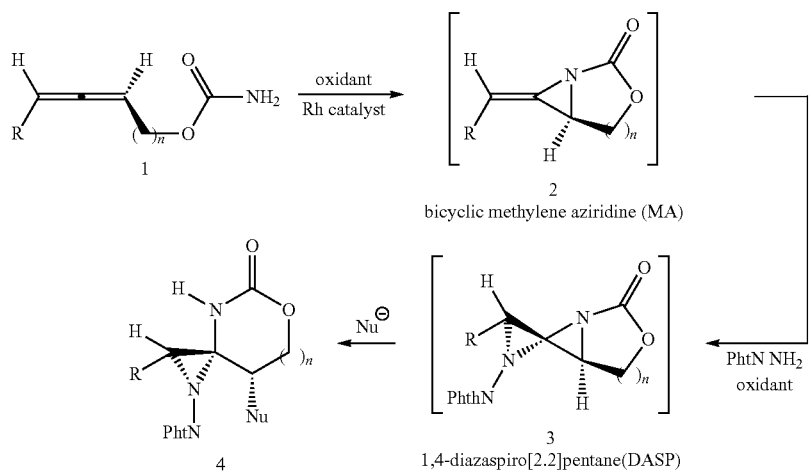

TABLE 2-2-continued

The preparation of electronically differentiated 1,4-diazaspiro[2.2]pentane aminals.

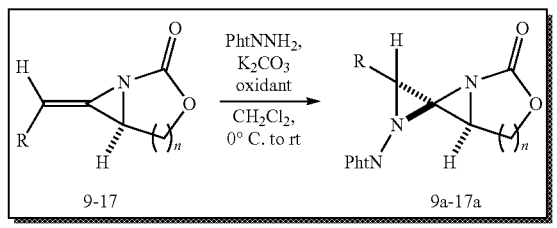

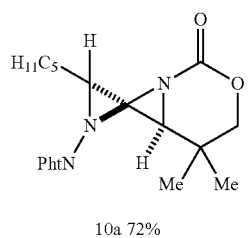

10a 72%

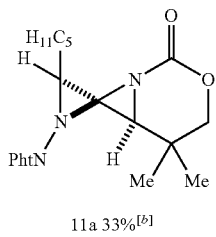

11a 33%[b]

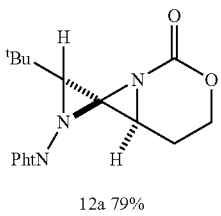

12a 79%

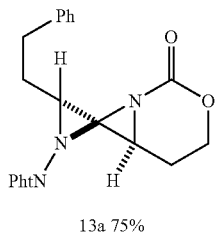

13a 75%

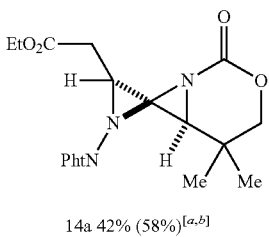

14a 42% (58%)[a,b]

TABLE 2-2-continued

The preparation of electronically differentiated 1,4-diazaspiro[2.2]pentane aminals.

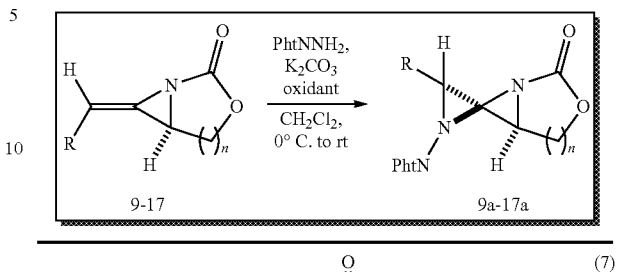

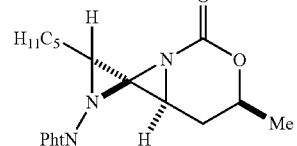

15a 66% (71%)[b]

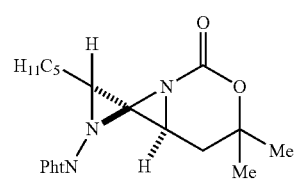

16a 40% (56%)[c]

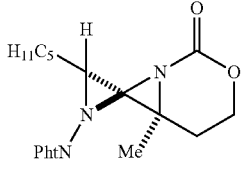

17a 46%

[a]Yield based on recovered starting material.
[b]The starting material was the Z methylene aziridine.
[c]Yield based on the E methylene aziridine.

Figure 3:
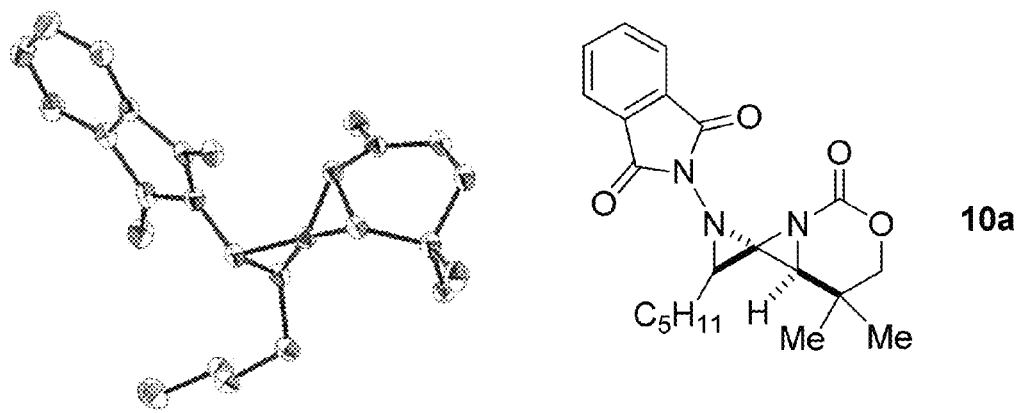

Substitution in the carbamate linker did not greatly affect the second aziridination event, as both the unsubstituted 9 and the gem-dimethyl substituted 10 gave similar yields of 9a and 10a (entries 1 and 2). However, the olefin geometry of the substrate MA was important. The E isomer 9 gave a 72% yield of the DASP, while the Z isomer 11 gave only a 33% yield and reacted much more slowly. Examination of the X-ray crystal structure of 10a (FIG. 3) indicated that the second aziridination occurred on the face of the MA opposite that of the first aziridine, as might be expected on steric grounds. The nitrene transfer appears to be stereoselective, as only one diastereomer was observed by $^1$H NMR. The E stereochemistry from the intermediate MA 10 translated into a syn relationship between the $C_5H_{11}$ side chain and the C—C bond of the central aziridine in 10a. Conversely, the DASP product 11a from the Z MA isomer 11 indicated the $C_5H_{11}$ chain and the C—C bond of the central aziridine are in an anti relationship. This forces a steric clash between the phthalimide group of the aziridine and the alkyl side chain, which may explain the slower reaction rate and lower yields as compared to the E methylene aziridines (Table 2-2, entries 3 and 8). These results also indicate that either the second aziridination occurs via a singlet nitrene, or the intermediate generated from addition of a triplet nitrene does not have time to rotate before ring closure to the DASP.

The stereoselective nature of the DASP formation ensured that the axial chirality from an enantioenriched allene could be transferred to the intermediate MA, and subsequently to the DASP, with good fidelity (Scheme 2-3). The er of the product 21 could be increased to 96:4 after one recrystallization. The plethora of new methods available for accessing enantioenriched allenes makes this approach a convenient way to access synthetic motifs containing three stereodefined and contiguous carbon-heteroatom bonds from simple precursors (for selected reviews on the synthesis of enantioenriched allenes, see M. Ogasawara, *Tetrahedron: Asymmetry* 2009, 20, 259; and Kim and Williams, *Curr. Opin. Drug Disc.* 2006, 11, 870).

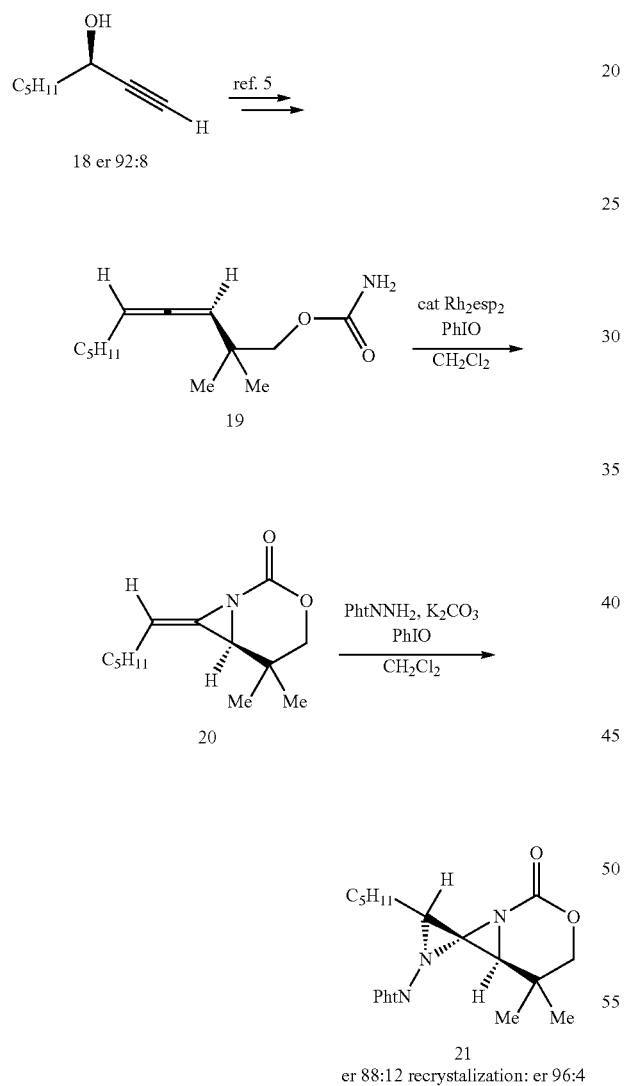

Scheme 2-3. Transfer of axial chirality to a 1,4-diazaspiro[2.2]pentane.

Another advantage of utilizing 1,4-diazaspiro[2.2]pentanes as reactive intermediates is the ability to further manipulate the molecule while still maintaining the N,N-aminal functionality. As illustrated in Table 2-3, weak nucleophiles gave almost exclusive ring-opening at the internal aziridine. For example, acetic acid opened the DASP 9a in 95% yield to give one regioisomer 22 (Table 2-3, entry 1).

TABLE 2-3

Nucleophilic ring-opening of tricyclic DASPs.

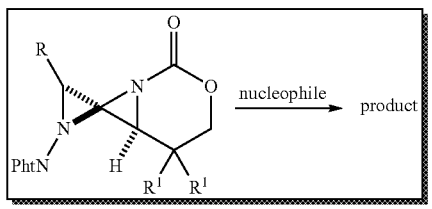

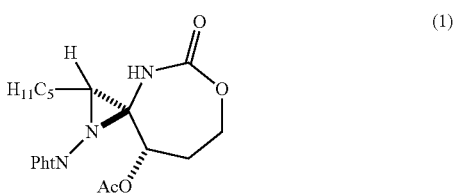

AcOH, 95% 22 (1)

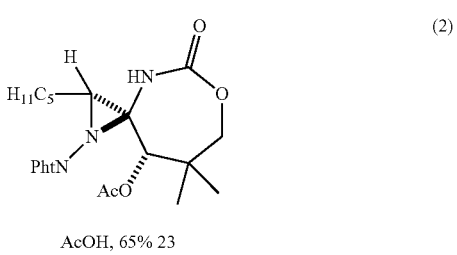

AcOH, 65% 23 (2)

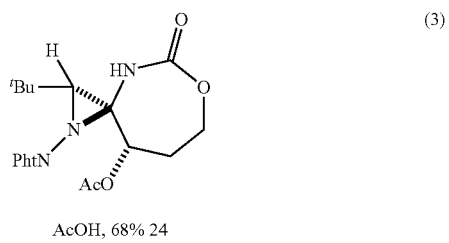

AcOH, 68% 24 (3)

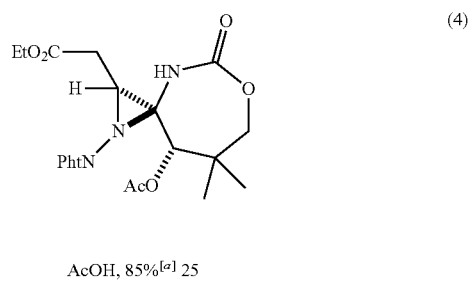

AcOH, 85%[a] 25 (4)

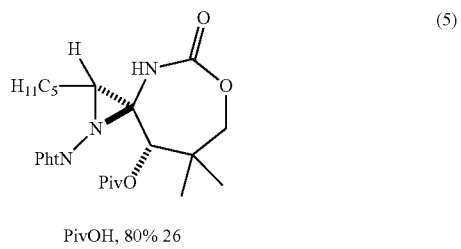

PivOH, 80% 26 (5)

TABLE 2-3-continued

Nucleophilic ring-opening of tricyclic DASPs.

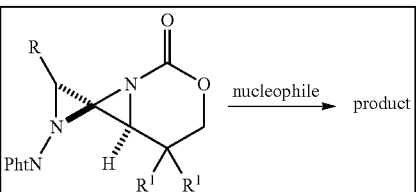

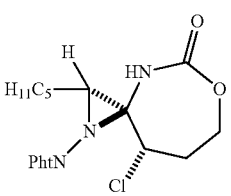

LiCl, 84% 27

(7)

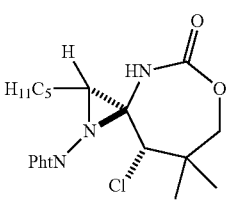

TMSCl, 93% 28

(8)

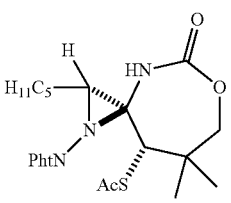

AcSH, 82% 29

(9)

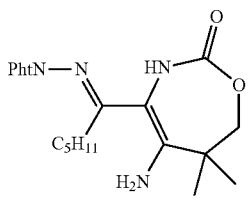

TMSN$_3$, 74% 30

TABLE 2-3-continued

Nucleophilic ring-opening of tricyclic DASPs.

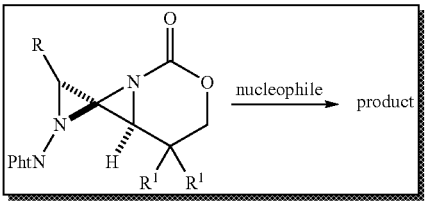

(10)

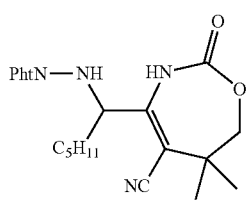

48%[b] 31

[a]The substrate was the DASP generated from aziridination of the Z methylene aziridine.
[b]The remainder of the mass balance was unreacted starting material.

The gem-dimethyl DASP 10a also gave only one product 23 (entry 2). For DASPs derived from Z-methylene aziridines (entry 4), reaction with acetic acid gave even better yields of the ring-opened product 25, perhaps due to less steric hindrance during the approach of the nucleophile. However, even the bulky pivalic acid gave good yields of the N,N-aminal 26 (entry 5). Chloride was also a good nucleophile, opening both DASPs 9a and 10a in excellent yields using either LiCl or TMSCl as the halogen source (entries 6 and 7). A new C—S bond could be introduced into the N,N-aminal by treatment of 10a with thioacetic acid to give 29 (entry 8) in 82% yield. Stronger nucleophiles, including cyanide and azide (entries 9 and 10) successfully opened the DASPs with good regioselectivity at the internal aziridine carbon. However, the basicity of the nucleophile and/or the increased acidity of the proton α to the newly introduced group promoted deprotonation and subsequent ring-opening of the Pht-protected aziridine to give the unusual heteroatom-substituted olefins 30 and 31.

Finally, the allenic carbamate substrates can be converted directly to functionalized N,N-aminals in one flask as a single diastereomer (Table 2-4). Four new carbon-heteroatom bonds and three chiral centers are generated in a stereoselective fashion using operationally simple procedures under mild reaction conditions.

TABLE 2-4

One-pot stereocontrolled synthesis of N,N-aminals from allenes.

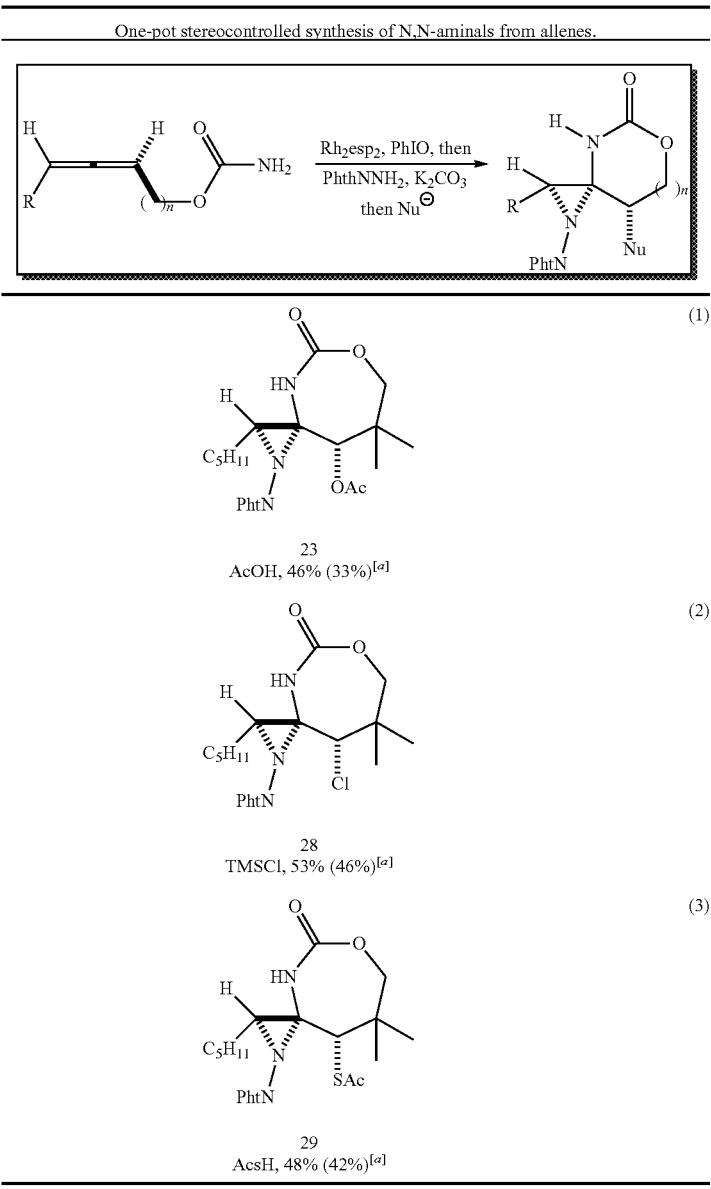

[a] Combined yield of the three individual steps. The yields were also increased significantly in the one-pot reaction; for example, the yield of 23 (Table 2-4, entry 1) improved to 46%, compared to 33% for the three-step process.

Accordingly, allene aziridination can be used as a key step for the preparation of stereodefined N,N-spiroaminals. The axial chirality of the substrate can be translated into three new heteroatom-bearing asymmetric centers in the final product. Allenic carbamates can also undergo an efficient and stereocontrolled one-pot amination to yield functionalized N,N-aminals. This efficient transformation generates four new carbon-heteroatom bonds in a single flask, where the axial chirality of the allene can be translated into the product with good fidelity.

General Procedure for Tandem Allene Oxidations to N,N-Aminals. A 50 mL flame-dried round bottom flask was charged with 3 Å molecular sieves, followed by $Rh_2esp_2$ (0.041 mmol, 0.025 equiv). The allenic carbamate (1.6 mmol, 1.0 equiv) in 15 mL of dry $CH_2Cl_2$ was added to the reaction flask. The resulting blue-green mixture was stirred for 10 min at rt under a flow of nitrogen, then iodosobenzene (4.1 mmol, 2.5 equiv) was added in one portion. The reaction was monitored by TLC until it was complete, then cooled to 0° C. in an ice bath. A portion of N-aminophthalimide (3.1 mmol, 1.9 equiv) and dry potassium carbonate (6.4 mmol, 4.0 equiv), followed by additional oxidant (3.0 mmol, 1.9 equiv) were added and the resulting light yellow slurry allowed to warm slowly to rt. The reaction mixture was monitored by TLC and additional portions of $PhtNNH_2$ and oxidant were added until no further conversion to the 1,4-diazaspiro[2.2]pentane was noted. The desired nucleophile was then added (15.0 equiv) and the reaction stirred at rt until complete. The reaction mixture was passed through a plug of silica gel to remove solids using first $Et_2O$, then EtOAc to flush the plug. The solvents were removed under reduced pressure and the residue was purified via silica gel column chromatography (hexanes/ethyl acetate gradient). Phenyl iodide eluted first from the column, followed by the Rh catalyst, unreacted methylene aziridine (if present), unreacted 1,4-diazaspiro[2.2]pentane(s) (if present), products of the hydrolysis of the excess N-aminophthalimide and finally, the desired N,N-aminal product as a single diastereomer.

Experimental Details. See the General Experimental Information section of Example 1 for details regarding materials and instrumentation, and for the preparation of allene substrates.

I. Intermolecular Synthesis of 1,4-Diazaspiro[2.2]pentanes.

General Procedure. A solution of the allene (1.0 mmol, 1.0 equiv) in 10 mL of dry dichloromethane was treated with N-aminophthalimide (2.8 mmol, 2.8 equiv) and dry potassium carbonate (7.0 mmol, 7.0 equiv), followed by PhIO (3.0 mmol, 3.0 equiv). The resulting light yellow slurry was stirred at rt for 2 h, during which time the yellow color darkened. Additional portions of N-aminophthalimide (1.0 mmol, 1.0 equiv) and PhIO (1.0 mmol, 1.0 equiv) were added if necessary and the reaction monitored by TLC until no starting material remained. If the DASP product was sensitive to ring-opening by acetate, the reaction could be stopped prior to completion and the allene starting material recovered. A non-aqueous workup was preferred, as many of the DASPs were sensitive to water. The salts were filtered off and washed with several small portions of dry dichloromethane. The volatiles were removed under reduced pressure either on a vacuum line or using a rotary evaporator with the water bath kept at rt or below. For less reactive DASPs, the reaction mixture was diluted with water and the aqueous layer quickly extracted three times with portions of dichloromethane. The combined organics were washed with brine, dried over sodium sulfate and the volatiles removed under reduced pressure. The residue was loaded onto a silica gel column packed with hexanes and eluted using a hexanes/ethyl acetate gradient. For sensitive DASPs, the column was pre-treated with a 99.5:0.5 mixture of hexanes/triethylamine, then further eluted with 4 column volumes of hexanes before loading the column. In most cases, phenyl iodide eluted first from the column, followed by unreacted allene (if present), any intermediate methylene aziridines, then the desired 1,4-diazaspiro[2.2]pentane(s) and finally, N-aminophthalimide and its hydrolysis products. The order of elution of DASP and N-aminophthalimide was variable depending on the polarity of the product.

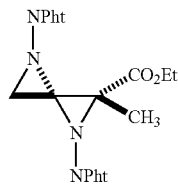

Compound 5a. The light yellow solid was obtained in 59% yield after column chromatography (hexanes/EtOAc gradient). The compound was further recrystallized from EtOAc/CHCl$_3$ to obtain crystals suitable for X-ray crystallography. Proton NMR showed approximately a 100:22:11 mixture of invertomers at rt. The identity of the invertomers was not established, as variable temperature NMR studies indicated only a single diastereomer was present. Major invertomer: $^1$H NMR (600 MHz, CDCl$_3$) δ 7.79-7.65 (Ar, 8H), 4.15 (d, 1H, J=1.2 Hz), 3.97 (m, 1H), 3.89 (m, 1H), 3.63 (d, 1H, J=1.2 Hz), 1.78 (s, 3H), 0.94 (t, 3H, J=7.3 Hz). Minor invertomer: $^1$H NMR (600 MHz, CDCl$_3$) δ 7.79-7.65 (Ar, 8H), 4.63 (d, 1H, J=3.5 Hz), 4.34 (m, 2H), 3.29 (d, 1H, J=3.5 Hz), 1.59 (s, 3H), 1.32 (t, 3H, J=6.4 Hz). Mixture of invertomers: $^{13}$C NMR (150 MHz, CDCl$_3$) δ 167.4, 165.9, 165.8, 164.9, 134.5, 134.4, 134.3, 134.0, 133.9, 130.5, 130.3, 130.2, 129.7, 123.4, 123.3, 123.2, 62.8, 62.4, 62.1, 52.9, 35.5, 35.2, 14.1, 13.7, 13.5, 12.8. HRMS (ESI) m/z calculated for [M+Na]$^+$ 469.1119, found 469.1130.

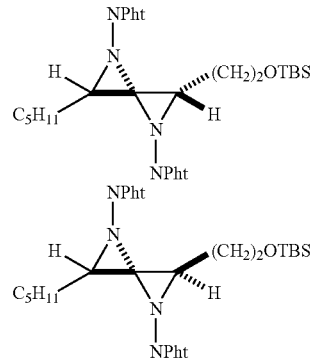

Compound 7a. The light yellow solid was obtained in 65% yield after column chromatography as approximately a 1:1 mixture of diastereomers. Both diastereomers: $^1$H NMR (500 MHz, CDCl$_3$) δ 7.83-7.60 (Ar, 8H total), 4.29 (overlapping signals, 0.8H total), 4.04 (m, 0.5H total), 3.87 (overlapping signals, 1.9H total), 3.68 (dd, 0.8H total, J=6.5, 6.5 Hz), 2.67 (m, 0.5H total), 2.44 (m, 1.0H total), 2.20 (overlapping signals, 1.5H total), 1.88 (m, 1.0H total), 1.78-1.60 (overlapping signals, 2.5H total), 1.40-1.28 (br m, 3.5H total), 0.88-0.80 (2 t, 3H total), 0.82-0.72 (2 s, 9H total), 0.08 and 0.06 (2 s, 3H total), −0.08 and −0.09 (2 s, 3H total). $^{13}$C NMR (125 MHz, CDCl$_3$) δ 167.9, 165.5, 165.4, 165.2, 165.1, 134.4, 134.2, 134.1, 134.0, 133.8, 132.6, 130.5, 130.4, 130.3, 123.5, 123.1, 123.0, 70.5, 69.9, 60.5, 60.2, 50.3, 47.4, 47.3, 45.6, 34.1, 31.8, 31.7, 31.6, 30.6, 28.1, 26.3, 26.0, 25.9, 25.7, 25.6, 22.5, 22.4, 18.2, 18.1, 14.0, 13.9, −5.4 (2), −5.5, −5.6. HRMS (ESI) m/z calculated for [M+Na]$^+$ 611.2661, found 611.2637.

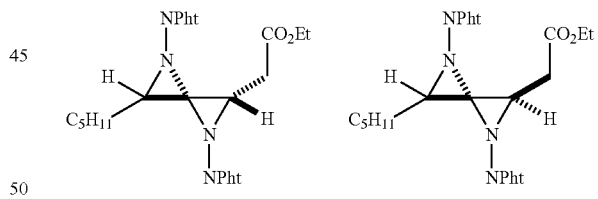

Compound 7b. The light yellow solid was obtained in 73% yield as a 1.6:1 mixture of diastereomers following column chromatography. Major diastereomer: $^1$H NMR (500 MHz, CDCl$_3$) δ 7.90-7.64 (Ar, 8H), 4.37 (dd, 1H, J=7.1, 5.8 Hz), 4.23 (q, 2H, J=7.4 Hz), 4.01 (dd, 1H, J=8.3, 5.2 Hz), 3.55 (dd, 1H, J=17.5, Hz), 3.49 (dd, 1H, J=17.5, 8.0 Hz), 1.91 (m, overlapping signals, 2H), 1.69-1.44 (m, overlapping signals, 6H), 1.31 (t, 3H, J=7.2 Hz), 0.85 (t, 3H, J=7.2 Hz). Minor diastereomer: $^1$H NMR (500 MHz, CDCl$_3$) δ 7.9-7.64 (Ar, 8H), 4.55 (dd, 1H, J=8.5, 5.5 Hz), 4.05 (dq, 2H, J=7.2, 1.3 Hz), 3.80 (dd, 1H, J=6.3, 6.3 Hz), 3.30 (dd, 1H, J=16.9, 5.5 Hz), 2.58 (dd, 1H, J=17.1, 8.7 Hz), 2.45 (m, 1H), 2.20 (m, 1H), 1.69-1.44 (br m, 6H), 1.08 (t, 3H, J=7.2 Hz), 0.94 (t, 3H, J=7.2 Hz). Both diastereomers: $^{13}$C NMR (125 MHz, CDCl$_3$) δ 170.6, 169.5, 167.9, 165.4, 165.3, 165.2, 165.0, 163.4, 135.1, 134.3, 134.2, 134.1, 133.9, 132.6, 130.5, 130.2, 130.0, 124.4, 123.6, 123.5, 123.3, 123.1, 123.0, 69.6, 69.5, 60.9 (2), 49.8, 48.1, 45.2, 43.0, 35.9, 33.6, 31.7, 31.6, 30.2, 28.2, 26.3, 25.7, 22.5, 22.4, 14.2, 14.0, 13.9 (2). HRMS (ESI) m/z calculated for [M+Na]⁺ 539.1902, found 539.1906.

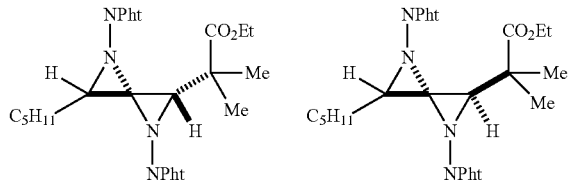

Compound 7c. The compound was obtained in 51% yield as a light yellow solid as an apparent 1.3:1 mixture of diastereomers (or possibly invertomers). A 19% yield of a mixture of the intermediate methylene aziridines 6c was also obtained. ¹H NMR (500 MHz, CDCl₃) δ 8.11-7.59 (Ar, 8H), 4.58 and 2.69 (2 s in a ratio of 1.3:1, 1H total), 3.91 and 3.84 (q, J=7.2 Hz and app dd, J=7.6, 5.9 Hz, 2H), 2.52 (m, 1H), 2.22 (m, 1H), 2.08 (s, 1H), 1.79 (m, 2H total), 1.61 (s, 3H), 1.51-1.37 (overlapping signals, 4H total), 1.14 (s, 3H), 0.94 (t, 3H, J=7.3 Hz), 0.89 (t, 3H, J=7.3 Hz). ¹³C NMR (125 MHz, CDCl₃) δ 175.2, 168.0, 165.4, 165.2, 136.0, 135.5, 135.1, 134.3, 134.1, 133.8, 130.5, 130.3, 124.5, 123.6, 123.1 (2), 68.8, 60.9, 50.8, 50.7, 42.9, 31.9, 28.2, 26.4, 23.9, 22.6, 20.7, 14.1, 14.0. HRMS (ESI) m/z calculated for [M+N+H₂O]⁺ 585.2320, found 585.2307. The methylene aziridine 8c was also isolated as a mixture of regioisomers. HRMS (ESI) m/z calculated for [M+Na]⁺ 407.1942, found 407.1932.

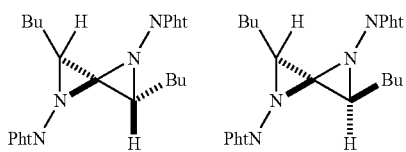

Compound 7d. The desired product was obtained in 46% yield as one major diastereomer (dr>9:1 by ¹H NMR). ¹H NMR (500 MHz, CDCl₃) δ 7.96-7.62 (Ar, 8H), 4.25 (dd, 1H, J=6.5, 6.2 Hz), 3.65 (t, 1H, J=6.9 Hz), 2.46 (m, 1H), 2.21 (m, 1H), 1.75-1.34 (several overlapping signals, 10H), 0.96 (t, 3H, J=7.5 Hz), 0.86 (t, 3H, J=7.5 Hz). ¹³C NMR (125 MHz, CDCl₃) δ 165.4, 165.2, 135.9, 134.5, 134.2, 134.1, 130.5, 130.2, 125.6, 123.4, 123.0, 122.9, 70.4, 49.8, 47.2, 30.3, 28.8, 27.8, 27.6, 22.5, 22.4, 13.8, 13.7. HRMS (ESI) m/z calculated for [M+Na]⁺ 495.2003, found 495.1995.

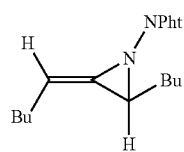

Compound 8d. The methylene aziridine was obtained in 7% yield. ¹H NMR (300 MHz, CDCl₃) δ 7.78-7.63 (Ar, 4H), 6.23 (ddd, 1H, J=7.4, 7.2, 1.9 Hz), 3.36 (dd, 1H, J=5.4, 5.3 Hz), 2.15 (2 d, 2H, J=7.3 Hz), 1.81-1.58 (m, 2H), 1.48-1.20 (several signals, 8H), 0.92 (t, 3H, J=7.2 Hz), 0.87 (t, 3H, J=7.2 Hz). ¹³C NMR (75 MHz, CDCl₃) δ 165.2, 134.3, 133.9, 131.5, 130.6, 123.5, 122.9, 113.3, 49.5, 31.6, 31.4, 28.8, 28.5, 22.6, 22.2, 13.9, 13.8. HRMS (ESI) m/z calculated for [M+H]⁺ 313.1911, found 313.1914.

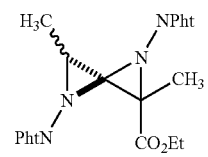

Compound 7e. The DASPs were obtained in 62% yield as approximately a 1:1 mixture of diastereomers. Less polar diastereomer: ¹H NMR (500 MHz, CDCl₃) δ 7.90-7.67 (Ar, 8H), 4.18 (m, 1H), 3.78 (m, 1H), 3.64 (m, 1H), 1.89 (s, 3H), 1.81 (d, 3H, J=4.5 Hz), 0.87 (t, 3H, J=7.4 Hz). ¹³C NMR (125 MHz, CDCl₃) δ 167.9, 166.0, 165.3, 164.5, 135.5, 134.3, 134.2, 133.8, 132.7, 130.8, 130.1, 129.8, 124.7, 123.9, 123.6, 123.1, 123.0, 68.0, 62.1, 51.8, 39.4, 18.5, 13.5, 13.2. HRMS (ESI) m/z calculated for [M+Na]⁺ 483.1276, found 483.1269. More polar diastereomer: ¹H NMR (600 MHz, CDCl₃) δ 8.04-7.81 (Ar, 8H), 4.89 (q, 1H, J=5.7 Hz), 4.89 (m, 2H), 1.75 (s, 3H), 1.66 (d, 3H, J=5.9 Hz), 1.37 (t, 3H, J=7.6 Hz). ¹³C NMR (150 MHz, CDCl₃) δ 168.0, 167.8, 165.8, 165.6, 161.5, 135.5, 134.4, 134.3, 133.9, 132.7, 130.4, 130.1, 124.7, 123.9, 123.6, 123.4, 123.1, 66.6, 62.4, 62.1, 52.6, 44.1, 14.8, 14.1, 12.8. HRMS (ESI) m/z calculated for [M+Na]⁺ 483.1276, found 483.1270.

II. Differentially Protected 1,4-Diazaspiro[2.2]pentanes

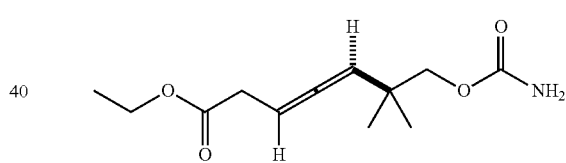

Precursor for Compound 14. Chlorosulfonyl isocyanate (10.8 mmol, 1.5 equiv) was dissolved in dry CH₂Cl₂ (25 mL) and placed in an ice bath. The homo-allenic alcohol (7.2 mmol, 1 equiv) was then added slowly, and once the addition was complete the ice bath was removed and stirred at rt until the starting material was consumed by TLC. The reaction was then placed in an ice bath and THF (6 mL) and water (3 mL) were added to the reaction. The vessel was fitted with a reflux condenser and refluxed until TLC indicated the reaction was complete. Brine (50 mL) was added to the reaction mixture and the solution was extracted with CH₂Cl₂ (2×50 mL), dried with Mg₂SO₄, and the solvents removed under reduced pressure. The residue was subjected to silica gel chromatography (0 to 50% EtOAc in hexanes gradient increased in increments of 10%) to give the product in 87% yield. ¹H NMR (300 MHz, CDCl₃) δ 5.34 (m, 1H), 4.83 (br, 2H), 4.16 (q, J=7.3 Hz, 2H), 3.86 (s, 2H), 3.02 (dd, J=7.0, 2.8 Hz, 2H), 1.27 (t, J=7.3 Hz, 3H), 1.05 (s, 6H). ¹³C NMR (75.5 MHz, CDCl₃) δ 203.8, 171.73, 157.3, 99.7, 86.5, 72.8, 61.0, 35.8, 35.4, 25.0, 24.8, 14.4. HRMS (ESI) m/z calculated for [M+Na]⁺ 264.1207, found 264.1214.

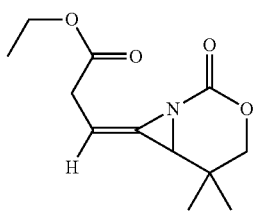 [SMILES: CCOC(=O)C/C=C1/C2N1C(=O)OCC2(C)C]

Compound 14. Dry CH$_2$Cl$_2$ (20 mL) was added to a flask that containing 4 Å molecular sieves (1.5 g) and Rh$_2$(esp)$_2$ (0.062 mmol, 0.03 equiv). The material prepared above (2.07 mmol, 1 equiv) was added and the reaction mixture was stirred for 10 min. PhIO (4.14 mmol, 2 equiv) was then added in one portion and the reaction was stirred vigorously until the starting material was consumed by TLC. The mixture was filtered through a silica gel pad and washed several times with EtOAc. The filtrate was then concentrated under reduced pressure. Crude NMR indicated a ratio of 1:2.8 of the E:Z olefin isomers. The crude material was purified by silica gel chromatography (the column was pre-treated with 1% triethylamine in hexanes). A gradient of 0% to 20% EtOAc in hexanes was used, increasing the more polar component by increments of 10%. The column was eluted with 80/20 hexanes/ethyl acetate until the green band corresponding to Rh$_2$(esp)$_2$ was collected. The polarity of the eluant was then increased to 20% ethyl acetate and slowly increased to 50% EtOAc in hexanes to give 14 in 86% yield as a 36% yield of a mixture of E:Z and 50% isolated as the pure Z isomer. Z isomer: $^1$H NMR (300 MHz, C$_6$D$_6$) δ 5.40 (t, J=7.4 Hz, 1H), 3.91 (q, J=7.2 Hz, 2H), 3.65 (dd, J=18.1, 7.2 Hz, 1H), 3.55 (dd J=18.1 Hz, 1H), 3.42 (d, J=10.6 Hz, 1H), 3.13 (d, J=10.6 Hz, 1H), 2.47 (s, 1H), 0.91 (t, J=7.2 Hz, 3H), 0.49 (s, 3H), 0.37 (s, 3H). $^{13}$C NMR (125 MHz, C$_6$D$_6$) δ 171.3, 154.8, 126.9, 97.3, 60.9, 49.0, 33.1, 28.9, 23.5, 20.6, 14.5. HRMS (ESI) m/z calculated for [M+Na]$^+$ 262.1050, found 262.1050.

General Procedure. The bicyclic methylene aziridines 9-16 and 17 were prepared as described in Example 1 (see also Grigg et al., Tetrahedron 2011, 67, 4318). If necessary, the E and Z bicyclic methylene aziridines were separated by column chromatography before initiating the DASP formation. A solution of the methylene aziridine (1.0 mmol, 1.0 equiv) in 10 mL of dry dichloromethane was cooled to 0° C. and treated with N-aminophthalimide (1.5 mmol, 1.5 equiv) and dry potassium carbonate (3.5 mmol, 3.5 equiv), followed by PhI(OAc)$_2$ or PhIO as the oxidant (1.6 mmol, 1.6 equiv). The resulting light yellow slurry was allowed to warm slowly to rt and monitored carefully by TLC. In some cases, the DASP product was sensitive to ring-opening by acetate and it was best to stop the reaction when conversion of the methylene aziridine to the DASP stalled. When reaction was complete, the dichloromethane was removed under reduced pressure on a vacuum line, the residue diluted with dry Et$_2$O and the organics decanted. The residual salts were washed two more times with Et$_2$O and the volatiles removed under reduced pressure on a vacuum line. A silica gel column was packed using 99.5:0.5 hexanes/triethylamine, followed by flushing with four column volumes of hexanes prior to loading the sample onto the column to improve the separation and prevent the decomposition of sensitive DASPs. The residue was loaded onto the column and eluted using a hexanes/ethyl acetate gradient. Phenyl iodide eluted first from the column, followed by unreacted MA (if present), then the desired 1,4-diazaspiro[2.2]pentane(s) and finally, N-aminophthalimide/hydrolysis products and/or products arising from DASP ring-opening. The DASPs were stored in a freezer at −20° C. It was best to run NMRs in deuterated benzene if the sample was to be recovered, as any residual acid in the CDCl$_3$ caused decomposition of the product.

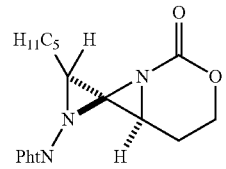

Compound 9a. The E methylene aziridine 9 was utilized as the starting material. The product was obtained in 58% yield after column chromatography as a single diastereomer; the yield based on recovered starting material was 65%. $^1$H NMR (600 MHz, CDCl$_3$) δ 7.75-7.65 (Ar, 4H), 4.56 (dd, 1H, J=11.0, 1.2 Hz), 4.46 (dd, 1H, J=5.4, 4.8 Hz), 3.93 (2 overlapping signals, 2H), 2.46 (m, 1H), 2.03-1.08 (several signals, 9H), 0.86 (t, 3H, J=7.2 Hz). $^{13}$C NMR (150 MHz, CDCl$_3$) δ 165.3, 157.7, 134.3, 130.8, 123.5, 68.8, 66.9, 45.9, 42.2, 31.8, 29.6, 26.1, 22.8, 22.7, 14.2. $^1$H NMR (500 MHz, C$_6$D$_6$) δ 7.25 (Ar, 2H), 6.71 (Ar, 2H), 4.28 (dd, 1H, J=5.9, 5.9 Hz), 3.52-3.46 (2 overlapping signals, 2H), 3.36 (ddd, 1H, J=10.9, 4.0, 1.9 Hz), 1.66-1.60 (overlapping signals, 4H total), 1.39-1.28 (br m, 4H total), 1.05 (dd, 1H, J=14.0, 6.5 Hz), 0.9 (t, 3H, J=6.5 Hz), 0.8 (overlapping m, 1H). $^{13}$C NMR (125 MHz, C$_6$D$_6$) δ 165.1, 157.1, 133.4, 130.9, 122.8, 68.0, 67.0, 45.5, 41.9, 31.9, 29.5, 26.2, 22.8, 22.3, 14.2. HRMS (ESI) m/z calculated for [M+Na]$^+$ 378.1425, found 378.1421.

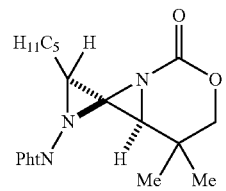

Compound 10a. The product was obtained as a single diastereomer in 72% yield using PhIO as the oxidant and the E methylene aziridine 10 as the substrate. $^1$H NMR (500 MHz, CDCl$_3$) δ 7.74-7.65 (Ar, 4H), 4.34 (d, 1H, J=10.6 Hz), 4.11 (dd, 1H, J=9.2, 3.5 Hz), 3.79 (d, 1H, J=11.3 Hz), 3.66 (s, 1H), 1.92 (m, 1H), 1.86-1.79 (br m, 2H), 1.58-1.22 (overlapping signals, 5H total), 1.29 (s, 3H), 0.93 (s, 3H), 0.90 (t, 3H, J=7.2 Hz). $^{13}$C NMR (125 MHz, CDCl$_3$) δ 165.2, 157.5, 134.1, 130.5, 123.2, 78.0, 65.0, 51.1, 46.0, 31.6, 31.2, 29.6, 25.8, 24.0, 22.5, 21.0, 14.0. HRMS (ESI) m/z calculated for [M+H]$^+$ 384.1918, found 384.1926.

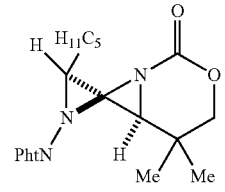

Compound 11a. The compound was obtained in 33% yield as a single diastereomer using PhIO as the oxidant and the Z methylene aziridine 11 as the substrate. The remainder of the mass balance was unreacted starting material, but the addition of additional aliquots of PhtNNH$_2$ and PhIO did not push the reaction to completion. $^1$H NMR (500 MHz, CDCl$_3$) δ 7.84-7.72 (Ar, 4H), 4.31 (d, J=12.0 Hz, 1H), 3.87-3.83 (m(overlapping signals), 2H), 3.33 (s, 1H), 2.18-1.99 (m, 2H), 1.77-1.59 (m, 2H), 1.43-1.33 (m, 4H), 1.26-1.22 (m(overlapping signals), 4H), 1.05 (s, 3H), 0.90 (t, J=7.3 Hz, 3H). $^{13}$C NMR (125 MHz, CDCl$_3$) δ 165.6, 155.8, 134.4, 130.2, 123.4, 77.6, 63.3, 48.7, 48.6, 31.5, 29.4, 29.2, 26.7, 24.0, 22.4, 19.9, 14.0. HRMS (ESI) m/z calculated for [M+Na]$^+$ 406.1738; found 406.1744.

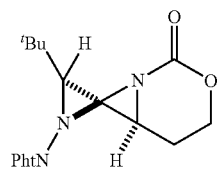

Compound 12a. The product was obtained in 79% yield. $^1$H NMR (500 MHz, CDCl$_3$) δ 7.77-7.67 (Ar, 4H), 4.60 (ddd, J=12.8, 11.5, 2.1 Hz, 1H), 4.40 (ddd, J=10.6, 4.7, 1.7 Hz, 1H), 3.97 (overlapping signals, 2H total), 2.50 (dddd, J=14.9, 6.8, 2.6, 2.1 Hz, 1H), 1.72 (m, 1H), 1.14 (s, 9H). $^{13}$C NMR (125 MHz, CDCl$_3$) δ 165.1, 157.5, 134.0, 130.5, 123.1, 68.4, 65.5, 53.6, 42.2, 31.3, 27.1, 23.8. HRMS (ESI) m/z calculated for C$_{18}$H$_{19}$N$_3$O$_4$ [M+H$^+$] 342.1449, found 342.1451.

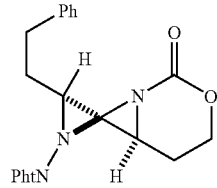

Compound 13a. The product was obtained in 75% yield. $^1$H NMR (500 MHz, CDCl$_3$) δ 7.80-7.68 (Ar, 4H), 7.33-7.19 (Ar, 5H), 4.50 (ddd, J=12.1, 10.9, 2.5 Hz, 1H), 4.25 (ddd, J=10.5, 4.0, 2.2 Hz, 1H), 4.00 (dd, J=6.2, 6.2 Hz, 1H), 3.84 (dd, J=8.7, 7.1 Hz, 1H), 3.05 (m, 2H), 2.19 (overlapping signals, 3H total), 1.09 (m, 1H). $^{13}$C NMR (125 MHz, CDCl$_3$) δ 165.1, 157.2, 141.0, 134.1, 130.5, 128.7, 128.5, 126.2, 123.2, 68.5, 66.5, 45.4, 41.8, 32.7, 31.8, 21.6. HRMS (ESI) m/z calculated for C$_{22}$H$_{19}$N$_3$O$_4$ [M+H$^+$] 390.1449, found 390.1463.

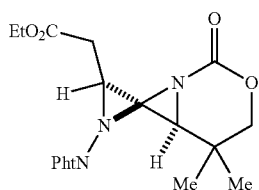

Compound 14a. The compound was obtained in 42% yield as a single diastereomer using PhIO as the oxidant and the Z methylene aziridine 14 as the substrate. The remainder of the mass balance was unreacted starting material and the yield based on recovered starting material was 58%. $^1$H NMR (300 MHz, CDCl$_3$) δ 7.82 (m, 2H), 7.75 (m, 2H), 4.33 (d, J=10.5 Hz, 1H), 4.26 (t, J=6.6 Hz, 1H), 4.19 (q, J=7.0 Hz, 2H), 3.88 (d, J=10.5 Hz, 1H), 3.38 (s, 1H), 3.35 (dd, J=18.0, 6.6 Hz, 1H), 3.12 (dd, J=18.0, 6.6 Hz, 1H) 1.27 (s, 3H), 1.27 (t, J=7.0 Hz, 3H), 1.16 (s, 3H). $^{13}$C NMR (75.5 MHz, CDCl$_3$) δ 170.8, 165.7, 156.3, 134.7, 130.3, 123.7, 78.1, 62.2, 61.3, 49.5, 43.4, 34.8, 29.8, 24.4, 20.1, 14.3. HRMS (ESI) m/z calculated for [M+Na]$^+$ 422.1323, found 422.1323.

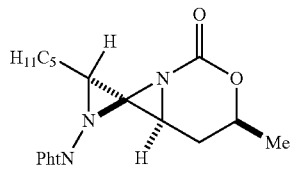

Compound 15a. The product was obtained in 66% isolated yield and 71% yield based on recovered and unreacted Z methylene aziridine. $^1$H NMR (500 MHz, CDCl$_3$) δ 7.78-7.67 (Ar, 4H), 4.77 (m, 1H), 3.94 (dd, J=7.0, 4.4 Hz, 1H), 3.86 (dd, J=9.3, 7.0 Hz, 1H), 2.45 (ddd, J=14.4, 6.0, 2.1 Hz, 1H), 1.95-1.88 (m, 1H), 1.78-1.67 (overlapping signals, 3H total), 1.42-1.27 (m, 8H), 0.92 (t, J=6.5 Hz, 3H). $^{13}$C NMR (125 MHz, CDCl$_3$) δ 165.0, 157.9, 134.0, 130.5, 123.1, 76.7, 66.9, 45.5, 41.4, 31.5, 29.4, 29.2, 25.8, 22.4, 20.6, 13.9. HRMS (ESI) m/z calculated for C$_{20}$H$_{23}$N$_3$O$_4$ [M+Na$^+$] 392.1581, found 392.1586.

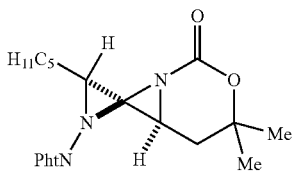

Compound 16a. The product was obtained in 40% isolated yield and 56% yield based on unreacted Z methylene aziridine. $^1$H NMR (500 MHz, CDCl$_3$) δ 7.78-7.67 (Ar, 4H), 3.93 (dd, J=7.8, 4.2 Hz, 1H), 3.83 (dd, J=9.1, 6.8 Hz, 1H), 2.31 (dd, J=14.9, 7.1 Hz, 1H), 1.94-1.89 (m, 1H), 1.73-1.67 (m, 3H), 1.64 (s, 3H), 1.58-1.20 (m, 8H), 0.92 (t, J=6.8 Hz, 3H). $^{13}$C NMR (125 MHz, CDCl$_3$) δ 167.7, 160.5, 136.7, 133.3, 125.9, 87.2, 70.8, 48.2, 42.7, 35.6, 34.3, 32.4, 32.0, 32.0, 28.6, 27.8, 25.1, 16.7. HRMS (ESI) m/z calculated for C$_{21}$H$_{25}$N$_3$O$_4$ [M+Na$^+$] 406.1738, found 406.1730.

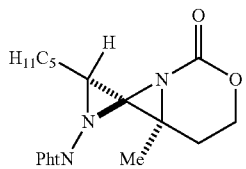

Compound 17a. The product was obtained in 46% yield. $^1$H NMR (500 MHz, CDCl$_3$) δ 7.78-7.67 (Ar, 4H), 4.59 (ddd, J=14.2, 11.4, 1.8 Hz, 1H), 4.38 (ddd, J=11.4, 3.8, 2.6 Hz, 1H), 3.96 (dd, J=7.0, 4.6 Hz, 1H), 2.14 (ddd, J=15.0, 3.4, 2.0 Hz, 1H), 2.00 (s, 3H), 1.95-1.90 (m, 1H), 1.74-1.65 (m, 4H), 1.42-1.34 (m, 4H), 0.92 (t, J=7.0 Hz, 3H). $^{13}$C NMR (125 MHz, CDCl$_3$) δ 165.3, 158.0, 134.0, 130.4, 123.1, 71.3, 67.4, 48.8, 46.1, 31.6, 29.3, 29.3, 25.7, 22.4, 18.2, 13.9. HRMS (ESI) m/z calculated for C$_{20}$H$_{23}$N$_3$O$_4$ [M+Na$^+$] 392.1581, found 392.1570.

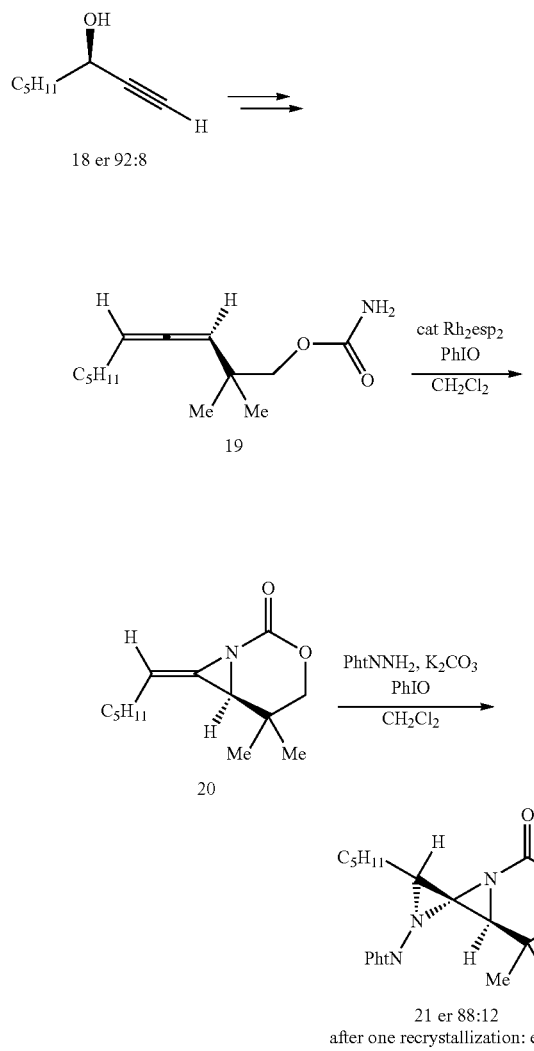

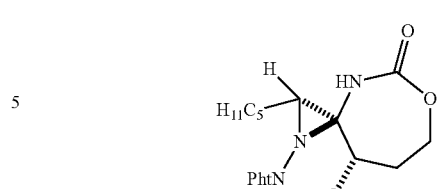

Compound 22. DASP 22 was obtained in 95% yield. $^1$H NMR (500 MHz, $C_6D_6$) δ 7.85-7.74 (Ar, 4H), 7.28 (NH, 1H), 4.35 (dt, J=11.1, 4.3 Hz, 1H), 4.22 (dd, J=11.9, 11.9 Hz, 1H), 3.64 (dd, J=11.9, 5.1 Hz, 1H), 3.59 (dd, J=6.0, 6.0 Hz, 1H), 2.09-2.04 (m, 1H), 1.98 (s, 3H), 1.93-1.68 (m, 5H), 1.43-1.36 (m, 4H), 0.93 (t, J=7.7 Hz, 3H). $^{13}$C NMR (125 MHz, $CDCl_3$) δ 170.0, 165.9, 153.7, 134.5, 130.0, 123.5, 74.9, 65.1, 53.9, 53.6, 31.5, 28.6, 26.2, 23.9, 22.4, 20.8, 14.0. HRMS (ESI) m/z calculated for $C_{21}H_{25}N_3O_6$ [M+H$^+$] 416.1817, found 416.1821.

Compound 21. The enantioenriched propargyl alcohol 18 was prepared according to literature procedure (Larock and Babu, *Tetrahedron* 1987, 43, 2013). The same procedure previously reported for the synthesis of racemic 21 was used to prepare the enantioenriched sample. High-pressure liquid chromatography (HPLC) analyses were performed at 224 and 254 nm using Shimadzu HPLC, Model LC-20AB. An AD-H column (4.6 μm diameter×258 mm) at a temperature of 40° C. was employed, using a flow rate of 1 mL/min and a gradient starting at 10% isopropanol in hexanes for 10 min and increasing to 30% isopropanol in hexanes. The eluant was then held at 30% isopropanol in hexanes until the run was completed. For the recrystallized 21, the HPLC run was started at 5% isopropanol in hexanes.

III. Reactions of 1,4-Diazaspiro[2.2]pentanes.

General Procedure for Acetic Acid DASP Ring Openings: The DASP was dissolved in enough THF to prepare a 0.1 M solution and cooled to 0° C. Glacial acetic acid (50.0 equivalents) was added dropwise to the reaction mixture over 2 min, ensuring that the reaction temperature remained at 0° C. The reaction was warmed to room temperature and monitored by TLC until complete (3-10 h). After consumption of the starting material, the reaction mixture was concentrated under reduced pressure and purified via column chromatography (hexanes/ethyl acetate gradient) to afford the desired ring-opened DASP as white solids.

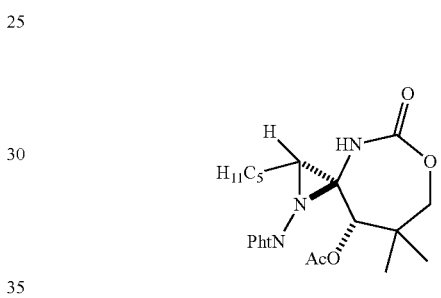

Compound 23. $^1$H NMR (300 MHz, $CDCl_3$) δ 7.84 (m, 2H), 7.75 (m, 2H), 7.72 (br, 1H), 4.06 (dd, J=9.7, 3.8 Hz, 1H), 3.93 (d, J=10.9 Hz, 1H), 3.78 (d, J=10.9 Hz, 1H), 3.30, (s, 1H), 2.01 (m, 1H), 1.90 (s, 3H), 1.76 (m, 2H), 1.39 (m, 5H), 1.16 (s, 3H), 1.15 (s, 3H), 0.93 (t, J=6.8 Hz, 3H). $^{13}$C NMR (75.5 MHz, $CDCl_3$) δ 169.6, 166.3, 153.4, 134.8, 129.9, 123.7, 77.6, 75.3, 61.8, 54.6, 31.8, 31.2, 30.2, 26.3, 22.6, 21.6, 18.6, 14.2. HRMS (ESI) m/z calculated for [M+Na]$^+$ 466.1949, found 466.1937.

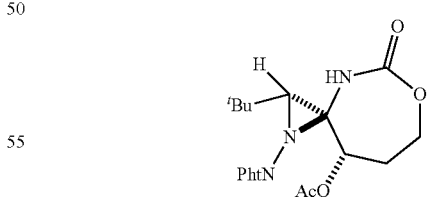

Compound 24. $^1$H NMR (500 MHz, $CDCl_3$) δ 7.84-7.73 (Ar, 4H), 7.54 (NH, 1H), 4.30 (ddd, J=11.1, 4.6, 2.3 Hz, 1H), 4.18 (ddd, J=11.7, 11.7, 2.6 Hz, 1H), 3.86 (dd, J=10.7, 5.2 Hz, 1H), 3.70 (s, 1H), 2.13-2.08 (m, 1H), 1.97-1.92 (overlapping signals, 4H total), 1.20 (s, 9H). $^{13}$C NMR (125 MHz, $CDCl_3$) δ 169.9, 165.9, 153.8, 134.6, 129.8, 123.5, 75.6, 64.8, 60.8, 53.7, 32.1, 29.6, 28.4, 24.4, 20.9. HRMS (ESI) m/z calculated for $C_{20}H_{23}N_3O_6$ [M+Na$^+$] 424.1580, found 424.1572.

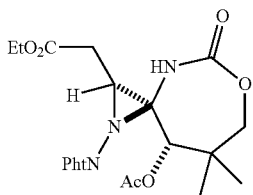

Compound 25. $^1$H NMR (300 MHz, CDCl$_3$) δ 7.85 (m, 2H), 7.77 (m, 2H), 6.77 (s, 1H), 4.24 (q, J=7.1 Hz, 2H), 3.89 (d, J=10.9 Hz, 1H), 3.81 (d, J=10.9 Hz, 1H), 3.70 (dd, J=7.4, 4.6 Hz, 1H), 3.28 (d, J=0.7 Hz, 1H), 3.18 (dd, J=17.3, 4.6 Hz, 1H), 2.64 (dd, J=17.3, 7.4 Hz, 1H), 2.16 (s, 3H), 1.31 (t, J=7.1 Hz, 3H), 1.22 (s, 3H), 1.20 (s, 3H). $^{13}$C NMR (75 MHz, CDCl$_3$) δ 170.3, 168.7, 152.6, 135.0, 130.3, 123.9, 76.3, 61.4, 61.1, 44.5, 33.1, 32.3, 23.7, 21.5, 20.2, 14.4. HRMS (ESI) m/z calculated for [M+Na]$^+$ 482.1534, found 482.1519.

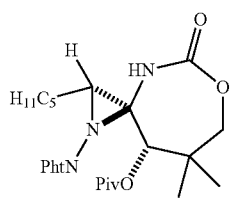

Compound 26. DASP 10a (0.13 mmol, 1 equiv) was dissolved in dry THF (1.5 mL) and pivalic acid (1.3 mmol, 10 equiv) was added. The reaction was stirred until complete by TLC (~72 h). The reaction was quenched with a saturated solution of NaHCO$_3$ (15 mL) and extracted with EtOAc (3×15 mL), dried with Na$_2$SO$_4$, and concentrated under reduced pressure. The residue was purified by silica gel chromatography (gradient 0→100% EtOAc in hexanes in increments of 20%) to give 26 in 80% yield. $^1$H NMR (500 MHz, CDCl$_3$) δ 7.82 (s, 1H), 7.78 (m, 4H), 3.92 (d, J=10.9 Hz, 1H), 3.87 (dd, J=9.6, 3.3 Hz, 1H), 3.76 (d, J=10.9 Hz, 1H), 3.32 (s, 1H), 2.03 (m, 1H), 1.78 (m, 2H), 1.42 (m, 5H), 1.19 (s, 3H), 1.13 (s, 3H), 0.93 (overlapping signals, 12H). $^{13}$C NMR (125 MHz, CDCl$_3$) δ 177.0, 166.0, 153.4, 134.8, 129.9, 123.6, 77.4, 75.5, 62.3, 55.1, 39.4, 31.2, 30.5, 26.7, 26.4, 23.0, 22.6, 19.1, 14.2. (line broadening set at 10 to observed the quaternary carbons). HRMS (ESI) m/z calculated for [M+Na]$^+$ 508.2419, found 508.2413.

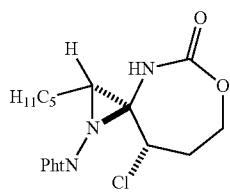

Compound 27. DASP 22 (0.14 mmol, 1 equiv) was dissolved in acetone (1.4 mL) and dry, powdered LiCl (1.4 mmol, 10 equiv) was added to the reaction mixture. The suspension was stirred at rt until TLC indicated complete consumption of 22. Water (15 mL) was added and the reaction mixture extracted with EtOAc (3×15 mL), dried with Na$_2$SO$_4$, and concentrated under reduced pressure. The residue was purified by silica gel chromatography (gradient 0→100% EtOAc in hexanes in increments of 20%) to give 27 in 84% yield. $^1$H NMR (300 MHz, CDCl$_3$) δ 7.80 (m, 4H), 7.10 (s, 1H), 4.41 (m, 1H), 4.26 (m, 1H), 3.71 (m, 2H), 2.22 (m, 1H), 1.99 (m, 1H), 1.70 (m, 4H), 0.93 (m, 3H). $^{13}$C NMR (125 MHz, CDCl$_3$) δ 164.0 (indirectly observed by HMBC), 153.9, 134.8, 130.0 (indirectly observed by HMBC), 124.0, 71.0, 64.7, 55.1, 54.3, 31.8, 29.0, 26.5, 24.4, 22.6, 14.2. HRMS (ESI) m/z calculated for [M+Na]$^+$ 466.1949, found 466.1937.

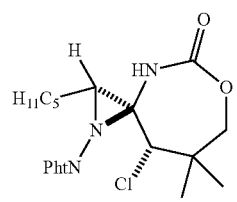

Compound 28. Chlorotrimethylsilane (150 μL, 1.18 mmol, 14 equiv) was dissolved in 1 mL THF and cooled to −78° C. The DASP 10a (33.2 mg, 0.086 mmol, 1.0 equiv) in 2.5 mL of THF was added dropwise over 2 min. After the addition was complete, the reaction mixture was warmed to 0° C. for 2 h and then to room temperature for an additional 2 h. The reaction mixture was concentrated under reduced pressure and the residue purified via column chromatography (hexanes/ethyl acetate gradient) to afford 28 in 93% yield as a white solid. $^1$H NMR (500 MHz, CDCl$_3$) δ 7.88-7.73 (Ar, 4H), 7.00 (NH, 1H), 4.39 (d, J=11.2 Hz, 1H), 4.12 (dd, J=11.2, 3.9 Hz, 1H), 3.74 (d, J=10.8 Hz, 1H), 3.32 (s, 1H), 2.00-1.94 (m, 1H), 1.76-1.67 (m, 2H), 1.43-1.34 (m, 5H), 1.25 (s, 3H), 1.22 (s, 3H), 0.93 (t, J=6.9 Hz, 3H). $^{13}$C NMR (125 MHz, CDCl$_3$) δ 166.6, 165.0, 153.2, 134.6, 130.4, 129.1, 123.8, 123.3, 73.9, 70.8, 62.8, 54.2, 31.6, 31.0, 30.5, 26.5, 26.4, 22.5, 20.5, 14.0. HRMS (ESI) m/z calculated for C$_{21}$H$_{26}$N$_3$O$_4$Cl [M+H$^+$] 1420.1685, found 420.1666.

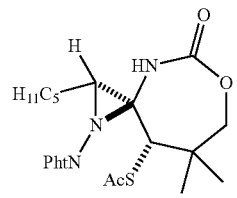

Compound 29. Thioacetic acid (600 μL, 8.4 mmol, 105 equiv) was dissolved in 1.5 mL of THF and cooled to −78° C. The DASP 10a (30.5 mg, 0.080 mmol, 1.0 equiv) dissolved in 2.5 mL THF was added dropwise to the solution over 2 min. The reaction mixture was maintained at −78° C. for an additional 15 min, warmed to 0° C. for 2 h and then left to warm to rt overnight. After TLC indicated complete consumption of the starting materials, the volatiles were removed under reduced pressure and the crude material was purified via column chromatography (hexanes/ethyl acetate gradient) to afford 29 in 82% yield as an off-white solid. $^1$H NMR (500 MHz, CDCl$_3$) δ 7.89-7.73 (Ar, 4H), 7.25 (NH, 1H), 4.07 (d, J=10.5 Hz, 1H), 3.88 (dd, J=10.1, 3.8 Hz, 1H), 3.80 (d, J=11.4 Hz, 1H), 3.35 (s, 1H), 2.27 (s, 3H), 2.19-2.12 (m, 1H), 1.89-1.75 (m, 2H), 1.62-1.53 (m, 1H), 1.46-1.37 (m, 4H), 1.17 (s, 3H), 1.14 (s, 3H), 0.94 (t, J=6.9 Hz, 3H). $^{13}$C NMR (125 MHz, CDCl$_3$) δ 193.3, 167.0, 165.1, 153.2, 134.6, 130.4, 129.3, 123.7, 123.5, 76.1, 63.4, 60.9, 56.8, 31.8, 31.5, 31.2, 31.1, 26.7, 24.6, 22.5, 19.7, 14.1 (line broadening set at 5 in order to observe quaternary carbons). HRMS (ESI) m/z calculated for $C_{23}H_{29}N_3O_5S$ [M+H$^+$] 1460.1901, found 460.1897.

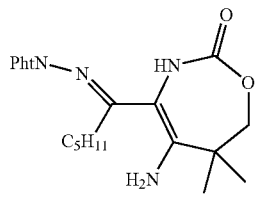

Compound 30. Sodium azide (0.44 mmol, 1.7 equiv) was dissolved in dry DMF (1.5 mL) and placed in an ice bath. Chlorotrimethylsilane (0.4 mmol, 1.5 equiv) was then added slowly to the solution and the reaction mixture was stirred for 30 min. The DASP 10a (0.26 mmol, 1 equiv) was dissolved in dry DMF (1 mL) and added to the reaction. The mixture was then heated to 50° C. overnight (12 h) and cooled back to rt. Water (10 mL) was added and the mixture extracted with $CH_2Cl_2$ (3×25 mL). The organic layer was washed with water (3×20 mL), dried with $Na_2SO_4$, and concentrated under reduced pressure. The residue was purified by silica gel chromatography (gradient 0→60% EtOAc in hexanes in increments of 10%) to give 30 in 74% yield. $^1$H NMR (300 MHz, CDCl$_3$) δ 7.89 (m, 2H), 7.76 (m, 2H), 7.21 (br, 2H), 6.09 (br, 1H), 4.21 (s, 2H), 2.41 (m, 1H), 1.40 (overlapping signals, 9H), 1.19 (m, 5H), 0.77 (m, 3H). $^{13}$C NMR (125 MHz, CDCl$_3$) δ 182.7, 167.8, 159.3, 157.3, 136.8, 133.7, 126.1, 104.9, 81.9, 42.6, 34.4, 33.3, 29.4, 26.5, 24.7, 16.4. HRMS (ESI) m/z calculated for [M+Na]$^+$ 421.1847, found 421.1859.

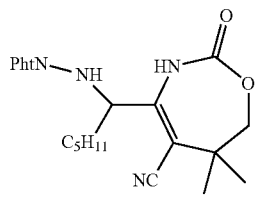

Compound 31. The DASP 10a (0.13 mmol, 1 equiv) and KCN (0.13 mmol, 1 equiv) were dissolved in dry acetonitrile (0.7 mL). Tetramethylethylenediamine (0.026 mmol, 0.2 equiv) was added to the solution, followed by TMSCN (0.16 mmol, 1.2 equiv). The reaction flask was fitted with a reflux condenser and placed in an oil bath pre-heated to 60° C. The reaction mixture was stirred overnight (12 h) and cooled to rt. Water was added (15 mL) and the mixture extracted with EtOAc (3×15 mL), dried with $Na_2SO_4$, and concentrated under reduced pressure. The residue was purified by silica gel chromatography (gradient 0→60% EtOAc in hexanes in increments of 10%) to give 31 in 48% yield. $^1$H NMR (300 MHz, CDCl$_3$) δ 8.07 (s, 1H), 7.87 (m, 2H), 7.79 (m, 2H), 4.70 (s, 1H), 4.41 (t, J=6.6 Hz, 1H), 4.10 (d, J=12.1 Hz, 1H), 4.02 (d, J=12.1 Hz, 1H), 1.73 (m, 3H), 1.38 (m, 5H), 1.23 (s, 3H), 1.11 (s, 3H), 0.92 (t, J=6.6 Hz, 3H). $^{13}$C NMR (75 MHz, CDCl$_3$) δ 166.2, 155.1, 145.6, 134.9, 129.9, 124.1, 117.0, 101.6, 75.1, 64.1, 38.5, 32.9, 31.4, 25.5, 25.3, 24.3, 22.6, 14.1. HRMS (ESI) m/z calculated for [M+Na]$^+$ 433.1847, found 433.1841.

IV. Tandem Reactions Involving 1,4-Diazaspiro[2.2]pentane Intermediates.

General Procedure for Tandem Reactions. A 50 mL flame-dried round bottom flask was charged with 3 Å molecular sieves (500 mg), followed by $Rh_2(esp)_2$ (0.041 mmol, 0.025 equiv). The allenic carbamate (1.6 mmol, 1.0 equiv) in 15 mL of dry $CH_2Cl_2$ was added to the reaction flask. The resulting blue-green mixture was stirred for 10 min at rt under a flow of nitrogen, then iodosobenzene (4.1 mmol, 2.5 equiv) was added in one portion. The reaction was monitored by TLC until it was complete, then cooled to 0° C. in an ice bath. A portion of N-aminophthalimide (3.1 mmol, 1.9 equiv) and dry potassium carbonate (6.4 mmol, 4.0 equiv), followed by additional oxidant (3.0 mmol, 1.9 equiv) were added and the resulting light yellow slurry allowed to warm slowly to rt. The reaction mixture was monitored by TLC and additional portions of PhtNNH$_2$ and oxidant were added until no further conversion to the 1,4-diazaspiro[2.2]pentane was noted. The desired nucleophile was then added (3.0-15.0 equiv) and the reaction stirred at rt until complete. The reaction mixture was passed through a plug of silica gel to remove solids using first Et$_2$O, then EtOAc to flush the plug. The solvents were removed under reduced pressure and the residue was purified via silica gel column chromatography (hexanes/ethyl acetate gradient). Phenyl iodide eluted first from the column, followed by the Rh catalyst, unreacted methylene aziridine (if present), unreacted 1,4-diazaspiro[2.2]pentane(s) (if present), products of the hydrolysis of the excess N-aminophthalimide and finally, the desired N,N-aminal product as a single diastereomer.

Example 3

Synthesis of 1,3-Diamines Via Allene Oxidation

Functionalized 1,3-diamines and 1,3-diamino-2-ols are valuable synthetic motifs for the construction of biologically active compounds. This example describes a one-pot bis-aziridination of allenes, followed by a Lewis acid-promoted rearrangement to yield 1,3-diamino-2-ones as one major diastereomer. The ketone undergoes reduction to the 1,3-diamino-2-ol with good diastereoselectivity.

Chiral 1,3-diamines are important building blocks for the preparation of a variety of natural products, pharmaceutically important compounds and ligands for transition metal catalysts. Approaches towards these motifs include the addition of enecarbamates to imines to yield anti 1,3-diamines, the diastereoselective reduction of ketimines, diastereoselective C—H amination and the addition of the α-carbanion of imines to N-protected imines, but there is still much interest in developing new stereoselective approaches to these molecules.

The development of new methods that can flexibly and stereoselectively introduce new sp$^3$ carbon-heteroatom bonds at the three consecutive carbons of an allene, preferably in a single pot, is important for efficient and economical preparation of therapeutic compounds. Example 2 above describes the synthesis and reactivity of an unusual class of heterocycles, the 1,4-diazaspiro[2.2]pentanes (DASPs, Scheme 3-1, 3) via the bis-aziridination of allenes. The reactive nature of these highly strained intermediates, and the ability to easily obtain them in enantioenriched form, prompted exploration of the conversion of allenes directly to 1,3-diamino-2-ones (Scheme 3-1).

Scheme 3-1. 1,3-diamino-2-ols via allene oxidation.

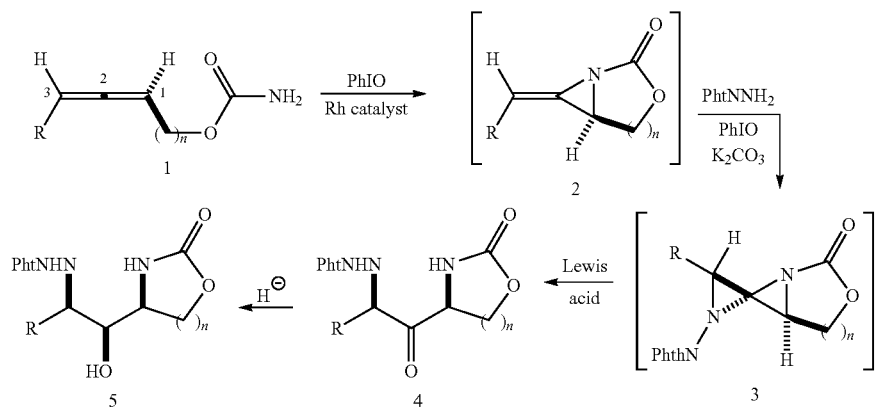

Simple hydrolysis of the N,N-aminal functionality of 3 (Scheme 3-1) should yield the 1,3-diamino-2-one 4. Attempts to transform the 1,4-diazaspiro[2.2]pentane 7 (entry 1, Table 3-2) directly to the 1,3-diamino-2-one 6 using a variety of Lewis acids, both in the presence and absence of water, resulted in either no reaction or decomposition of the substrate. It was postulated that relieving the ring strain might make one of the nitrogens more accessible for binding to the Lewis acid and facilitate the desired reaction. Treatment of the ring-opened 5 with a series of Lewis and Brønsted acids (Table 3-1) was investigated to facilitate the rearrangement of 5 to 6. Weak Lewis acids, including $CeCl_3$, $Ti(O^iPr)_4$ and $ZnCl_2$ (entries 1-4), gave no reaction and the starting material was recovered unchanged. $InCl_3$ (entry 6) gave slow conversion to the desired product, while $Cu(OTf)_2$ and $Sc(OTf)_3$ (entries 5 and 7) yielded a mixture of products. $BF_3OEt_2$, TsOH and $Bi(OTf)_3$ (entries 8-12) all gave complete conversion of the starting material, with the mild $Bi(OTf)_3$ resulting in an 96% isolated yield of 6.

TABLE 3-1

Investigation of Lewis acids for the rearrangement.

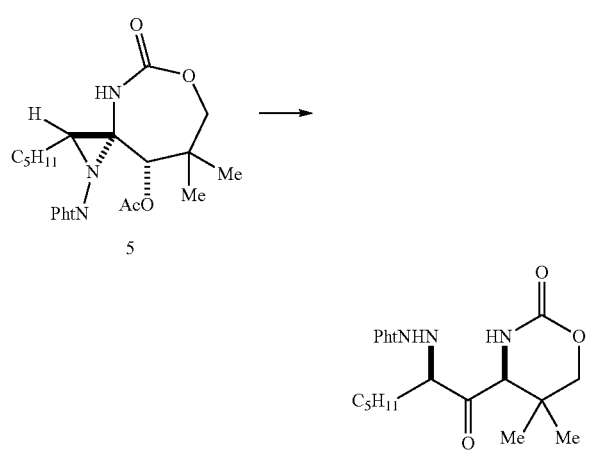

| entry | additives[a] | conversion |
|---|---|---|
| 1 | $CeCl_3 \cdot 7H_2O$ | 0% |
| 2 | $NiCl_2 \cdot 6H_2O$ | 0% |
| 3 | $Ti(O^iPr)_4$ | 0% |
| 4 | $ZnCl_2$ | 0% |
| 5 | $Cu(OTf)_2$ | 100%[b] |
| 6 | $InCl_3$ | 33% |
| 7 | $Sc(OTf)_3$ | 100%[b] |
| 8 | $BF_3OEt_2$ | 100% |
| 9 | TsOH | 100% |
| 10 | $Bi(OTf)_3$ | 96%[c] |
| 11 | $Bi(OTf)_3$ (0.2 equiv) | 100% |
| 12 | $Bi(OTf)_3$ (0.05 equiv) | 100% |

[a]1.0 equiv unless otherwise indicated.
[b]Complete conversion with several side products.
[c]Isolated yield.

$Bi(OTf)_3$ was chosen to further optimize the conversion of the 1,4-diazaspiro[2.2]pentane 7 directly to the 1,3-diamino-2-one using a catalytic amount of the Lewis acid. Treatment of 7 with AcOH, followed by addition of the Lewis acid (Table 3-2, entry 2) gave complete conversion of the DASP, but the ring-opening with AcOH was slow. Interestingly, ring-opening with TMSCl, followed by treatment with the Lewis acid (entry 3) gave only the ring-opened product and none of the desired rearrangement. This indicates that the ester was playing an important role in promoting the rearrangement. To significantly decrease the reaction time, AcOH was added to 7 at 35° C. and the mixture heated for 8 h prior to addition of the $Bi(OTf)_3$ (entry 4) to give 6 in 88% isolated yield over the two steps.

TABLE 3-2

One-pot ring-opening/rearrangement of DASP.

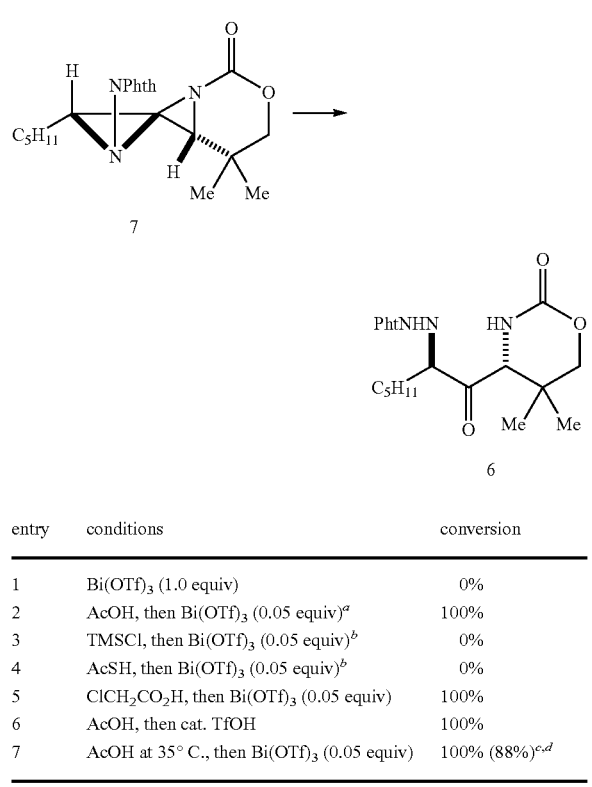

| entry | conditions | conversion |
|---|---|---|
| 1 | Bi(OTf)$_3$ (1.0 equiv) | 0% |
| 2 | AcOH, then Bi(OTf)$_3$ (0.05 equiv)$^a$ | 100% |
| 3 | TMSCl, then Bi(OTf)$_3$ (0.05 equiv)$^b$ | 0% |
| 4 | AcSH, then Bi(OTf)$_3$ (0.05 equiv)$^b$ | 0% |
| 5 | ClCH$_2$CO$_2$H, then Bi(OTf)$_3$ (0.05 equiv) | 100% |
| 6 | AcOH, then cat. TfOH | 100% |
| 7 | AcOH at 35° C., then Bi(OTf)$_3$ (0.05 equiv) | 100% (88%)$^{c,d}$ |

$^a$40 h reaction time.
$^b$The product was the ring-opened DASP.
$^c$12 h reaction time.
$^d$Isolated yield with a dr >19:1.

Using relatively optimized conditions, a variety of DASPs were converted to the corresponding 1,3-diamino-2-ones (Table 3-3). There was only a slight difference in yield between the use of the DASP 7 or the ring-opened DASP 5 (entries 1-2). DASPs formed from Z bicyclic methylene aziridines also underwent the desired rearrangement with high stereoselectivity (entries 3 and 4). The stereospecific nature of the reaction is illustrated by a comparison of the 1,3-diaminated ketone 6, obtained in 88% yield from the rearrangement of a DASP 7 derived from an E methylene aziridine, with the distinct product ketone 8c, obtained in 90% yield from the rearrangement of a DASP formed from a Z-methylene aziridine (Table 3-3, entries 2 and 4, respectively). The rearrangement was not affected by the absence of alkyl substitution in the tether (entries 5-9) or limited to the formation of six-membered rings, as a five-membered ring-containing product (entry 8) was obtained in 78% yield. The dr of the two nitrogen-bearing stereocenters was high in most cases (>19:1) and none of the other diastereomer was detected by $^1$H NMR spectroscopy. Not surprisingly, if the product was allowed to remain under the acidic conditions for extended periods of time, significant isomerization to a mixture of diastereomers did occur.

TABLE 3-3

Rearrangement of DASPs to 1,3-diaminated ketones.

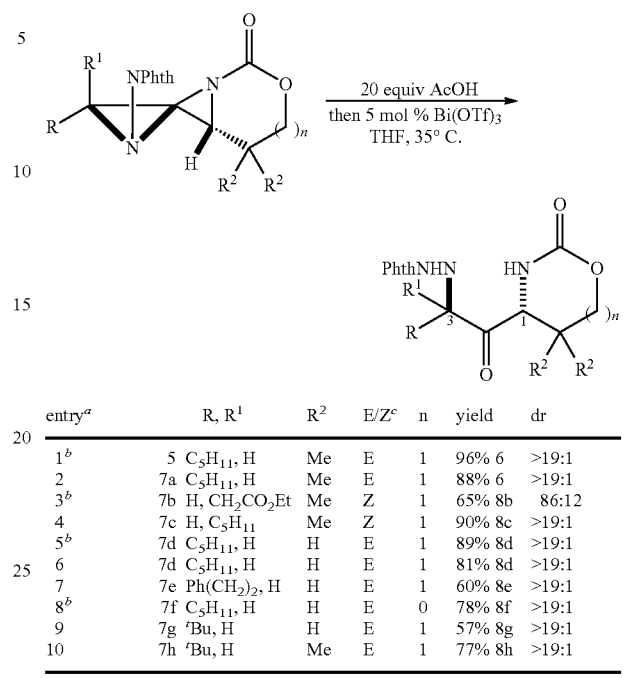

| entry$^a$ | R, R$^1$ | R$^2$ | E/Z$^c$ | n | yield | dr |
|---|---|---|---|---|---|---|
| 1$^b$ | 5 C$_5$H$_{11}$, H | Me | E | 1 | 96% 6 | >19:1 |
| 2 | 7a C$_5$H$_{11}$, H | Me | E | 1 | 88% 6 | >19:1 |
| 3$^b$ | 7b H, CH$_2$CO$_2$Et | Me | Z | 1 | 65% 8b | 86:12 |
| 4 | 7c H, C$_5$H$_{11}$ | Me | Z | 1 | 90% 8c | >19:1 |
| 5$^b$ | 7d C$_5$H$_{11}$, H | H | E | 1 | 89% 8d | >19:1 |
| 6 | 7d C$_5$H$_{11}$, H | H | E | 1 | 81% 8d | >19:1 |
| 7 | 7e Ph(CH$_2$)$_2$, H | H | E | 1 | 60% 8e | >19:1 |
| 8$^b$ | 7f C$_5$H$_{11}$, H | H | E | 0 | 78% 8f | >19:1 |
| 9 | 7g $^t$Bu, H | H | E | 1 | 57% 8g | >19:1 |
| 10 | 7h $^t$Bu, H | Me | E | 1 | 77% 8h | >19:1 |

$^a$The dr of the starting DASPs was >19:1 in all cases.
$^b$The starting material was the acetate-opened DASP with a dr >19:1.
$^c$Stereochemistry of the methylene aziridine used to form the DASP.

One convenient advantage of this methodology arises as a result of the ability to transfer the axial chirality of an enantioenriched allene to the 1,3-diaminated products. The fidelity of this transfer was verified by subjecting an enantioenriched DASP to the reaction conditions for the rearrangement to the ring opened product (eq 1). No degradation of the enantiopurity was indicated by chiral HPLC.

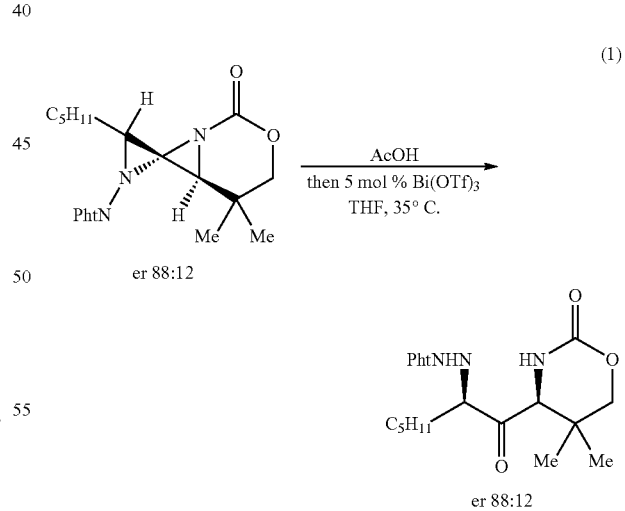

(1)

Verification was also sought for the relative stereochemistry of the two amine-bearing stereocenters. Attempts to prepare a rigid derivative of 6 were not successful. Whether the carbonyl could be reduced stereoselectively was then investigated. Obtaining X-ray crystal data on the resulting product would then reveal the relative configuration of the 1,3-diamino-2-ol stereotriad. Treatment of 6 (eq 2) with an excess of Na(OAc)$_3$BH gave a 70% yield of 19 as a single diastereomer, upon initial investigation.

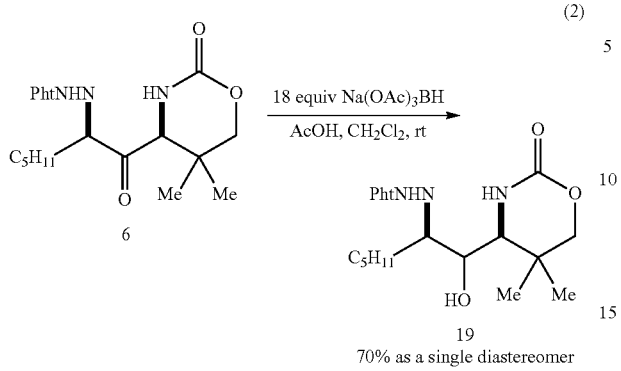

(2)

19
70% as a single diastereomer

The conversion of an allene to the resulting 1,3-diamine can be achieved in a single pot (eq. 3). Although the yields were only moderate (ca. 80% per step), the reaction introduces significant complexity into a simple, readily available substrate. The major loss in yield occurs in the first allene aziridination, where the formation of the Z methylene aziridine (MA) competes with that of the desired E MA. Fortunately, the Z methylene aziridine reacts much more slowly in the subsequent reactions and can be easily separated from the final desired product.

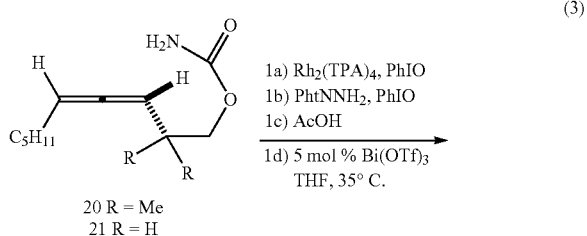

(3)

20 R = Me
21 R = H

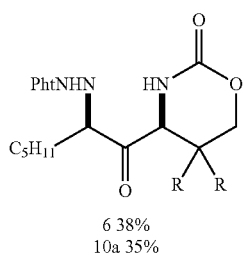

6 38%
10a 35%

Interestingly, it appeared that a relatively electron-rich acetate group was necessary to facilitate the rearrangement. When chloride (Table 3-1, entry 3) or chloroacetic acid (entry 4) was used to open the DASP 7, reaction to the 1,3-diamino-2-one did not occur and the ring-opened DASP was recovered unchanged. This indicates that the rearrangement may be passing through an acetoxonium ion.

This example demonstrates that 1,4-diazaspiro[2.2]pentanes, formed via the bis-aziridination of allenes, can serve asuseful reactive intermediates for the highly stereoselective synthesis of 1,3-diamines. The reaction also produces a ketone that can be stereoselectively reduced to yield 1,3-diamino-2-ols. These transformations and methodology can be applied to the total synthesis of biologically active natural products.

Example 4

Modular Functionalization of Allenes to Aminated Stereotriads

Nitrogen-containing stereotriads—compounds with three adjacent stereodefined carbons—are commonly found in biologically important molecules. However, the preparation of molecules bearing these motifs can be challenging. This example describes a modular oxidation protocol that converts a substituted allene to a triply functionalized amine of the form C—X/C—N/C—Y. A key step includes a Rh-catalyzed intramolecular conversion of the allene to a strained bicyclic methylene aziridine. This reactive intermediate can be further elaborated to the target products, often in one reaction vessel and with effective transfer of the axial chirality of the allene to point chirality in the stereotriad.

Figure 4:
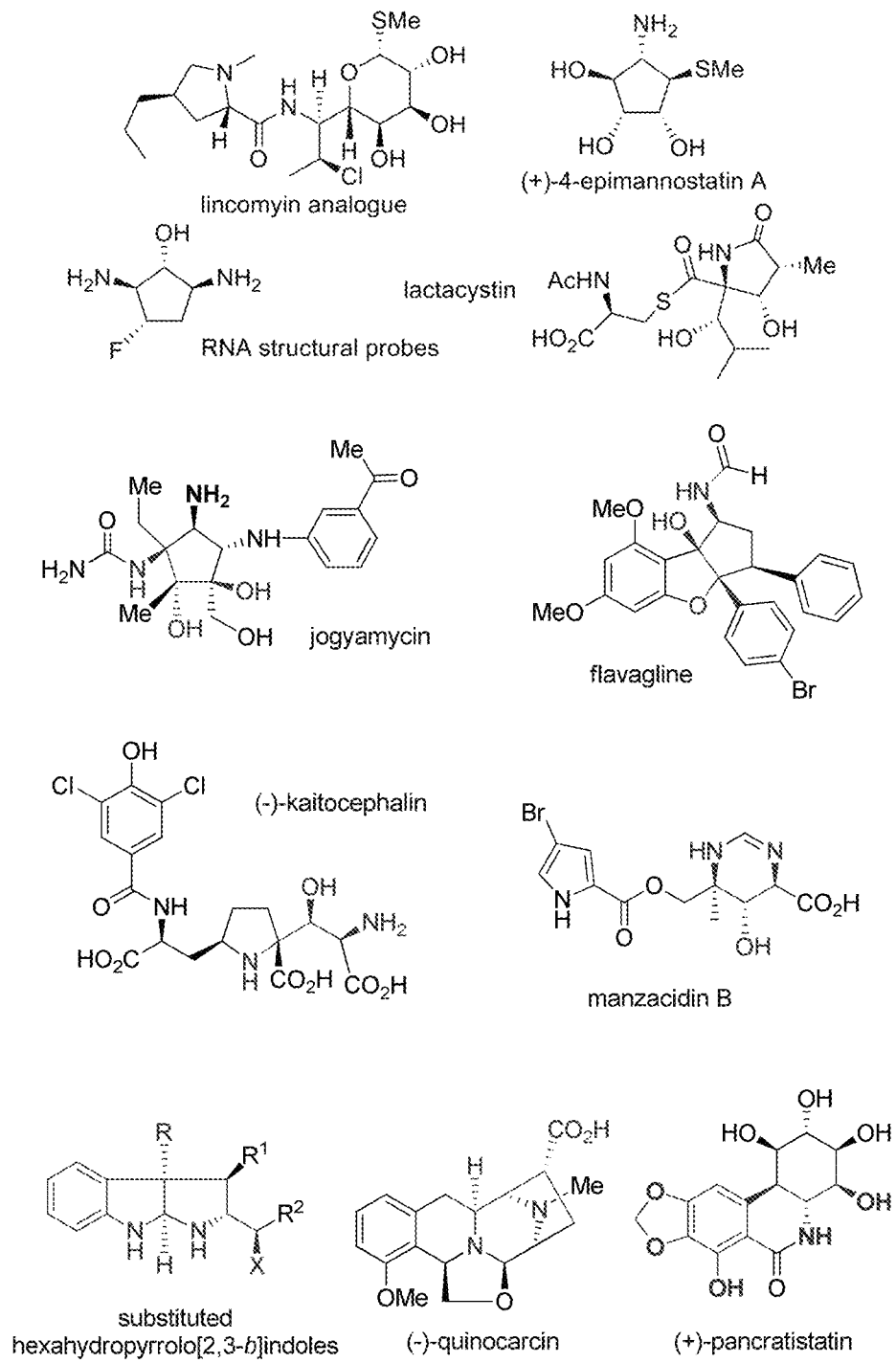
FIG. 4. Natural products and biologically active molecules having densely functionalized amines bearing stereodefined heteroatom groups located adjacent to the chiral nitrogen-bearing carbon occur frequently; and bioactive molecules with complex N/O/O and N/O/N stereotriads.

Densely functionalized amines bearing stereodefined heteroatom groups located adjacent to the chiral nitrogen-bearing carbon (X/N/Y stereotriads, for example, where X and Y represent a halogen, oxygen, nitrogen or sulfur-containing group) occur frequently in natural products and biologically active molecules (FIG. 4). Highly modular and streamlined methods for the chemo-, regio- and stereoselective construction of these motifs were developed as described herein. This example reports the modular preparation of X/N/Y stereotriads from allenes. These chiral hydrocarbons were chosen as precursors due to their ease of preparation, potential for introducing three new heteroatoms in a single reaction vessel and the ability to transfer readily available axial chirality to point chirality in the products.

Allene bis-epoxidation has been the only major approach thus far to introduce multiple heteroatoms into these chiral hydrocarbons. Previous efforts to transform allenic N-tosyloxycarbamates or carbamates 1 to bicyclic methylene aziridines 2 gave poor to moderate chemo- and stereoselectivities (Scheme 4-1, top). However, switching to an allenic sulfamate 4 gave a highly reactive methylene aziridine 5 that, in the presence of nucleophiles, underwent regioselective ring-opening to yield the E-enesulfamate 6 exclusively. The cyclic nature of 6 can impart good facial selectivity in its subsequent reaction with an electrophile, as conformation B minimizes the $A^{1,3}$ strain present in 6. The favored conformation of the resulting iminium ion 7 would again minimize $A^{1,3}$ strain. As the majority of electrophiles utilized by the inventors have A values smaller than that of $C_5H_{11}$, additional shielding of the top face of 7 can result in stereoselective reduction to yield the 1,2-syn:2,3-syn product 8 as the major diastereomer.

Scheme 4-1. Allene oxidation strategy for the preparation of nitrogen-containing stereotriads

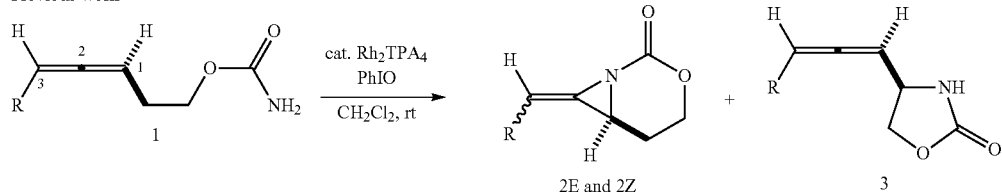

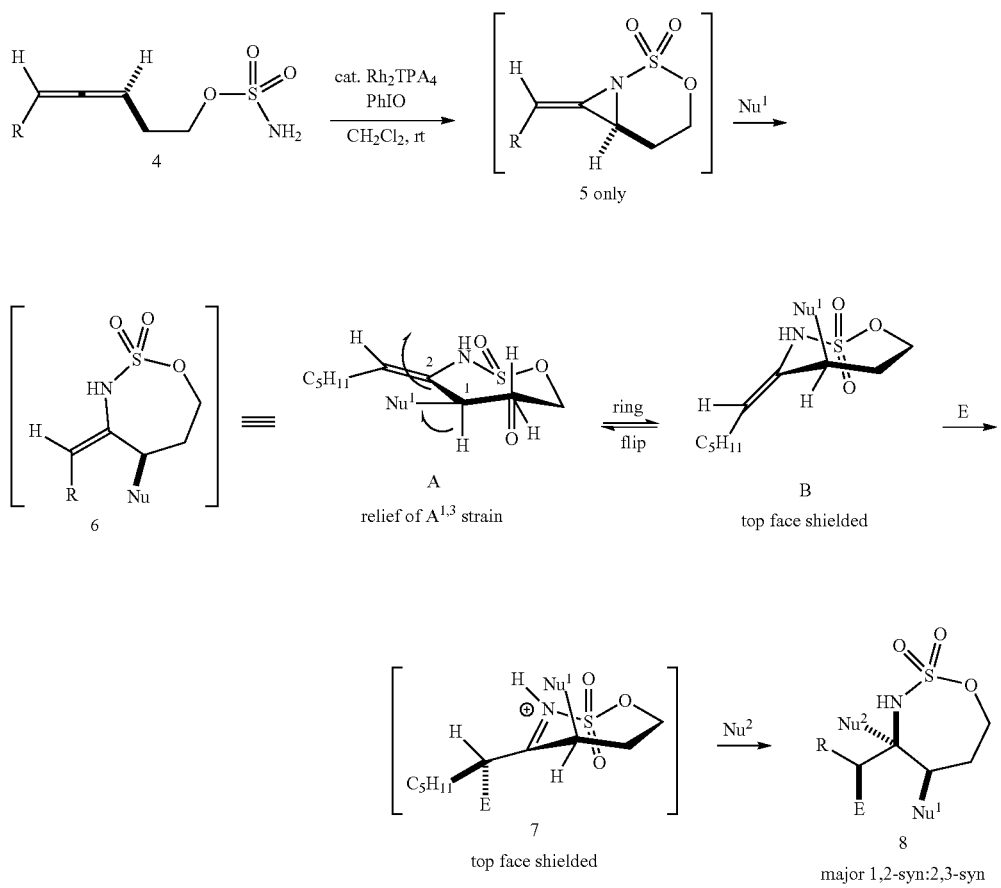

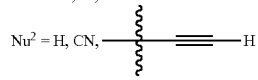

Treatment of an allenic sulfamate 9 (Table 4-1) with PhIO and catalytic $Rh_2TPA_4$ (TPA=triphenylacetate) cleanly yielded the desired E bicyclic methylene aziridine 5 (Scheme 4-1, R=$C_5H_{11}$) as observed by $^1H$ NMR. A series of weak nucleophiles promoted ring-opening of this methylene aziridine in situ to yield the corresponding E enesulfamates. Successful oxygen nucleophiles included AcOH, methanol and $H_2O$ (entries 1-3) and gave the products 10-12 in good yields.

The unusually activated nature of the bicyclic methylene aziridine was demonstrated by its facile reaction with amines that typically do not open aziridines in the absence of an exogenous Lewis acid (entries 4-6). Finally, PhSH and TMSCl (entries 7, 8) were also shown to be competent nucleophiles under these mild conditions.

TABLE 4-1

Tandem aziridination/ring-opening.

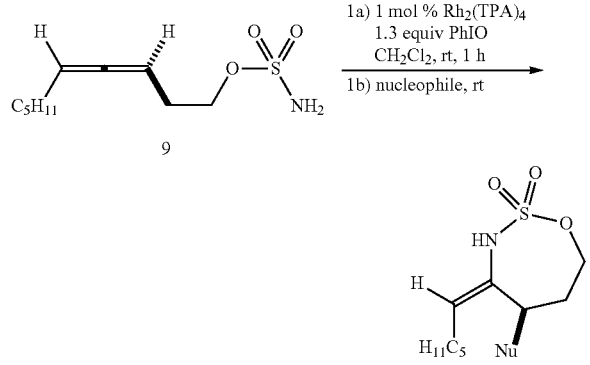

| entry | Nu—X | equiv | solvent[a] | temp (°C.) | time (h)[b] | yield | product |
|---|---|---|---|---|---|---|---|
| 1[c] | AcO—H | 6 | CH$_2$Cl$_2$ | rt | 5 | 75% | 10 |
| 2 | MeO—H | 50 | CH$_2$Cl$_2$ | rt | 1 | 77% | 11 |

TABLE 4-1-continued

| 3 | HO—H | 20 | CH$_3$CN[a] | rt | 0.7 | 74% | 12 |
|---|---|---|---|---|---|---|---|
| 4 | PhNH—H | 1.3 | CH$_2$Cl$_2$ | rt | 2 | 68% | 13 |
| 5 | morpholine | 1.6 | CH$_2$Cl$_2$ | rt | 2.5 | 71% | 14 |
| 6 | piperidine | 1.3 | CH$_2$Cl$_2$ | rt | 1 | 75%, 90%[d] | 15 |
| 7 | PhS—H | 10 | CH$_2$Cl$_2$ | rt | 1 | 69% | 16 |
| 8 | Cl—TMS | 1.5 | THF[a] | 0° C. to rt | 8 | 56% (62%)[e] | 17 |

[a]solvent exchange
[b]time for MA ring-opening only
[c]0.3 mol % catalyst was used
[d]$^1$H NMR yield based on the use of mesitylene as an internal standard
[e]based on recovered starting material The enesulfamates proved sufficiently nucleophilic to react with a range of standard electrophiles. The intermediate iminium ion 7 (see Scheme 4-1) was sensitive to hydrolysis, thus, the dr of the product resulting from the initial nucleophilic addition step was not determined. Rather, the reductant was added to the same reaction vessel to supply the final desired stereotriad and the overall dr of the reaction recorded (Table 4-2). For example, treatment of 10 with N-bromosuccinimide (NBS), followed by NaBH$_3$CN (entry 1) gave 18 in 71% isolated yield and a dr of 12.5:1. The relative stereochemistry of 18 was confirmed as 1,2-syn-2,3-syn by X-ray crystallography and the minor diastereomer was assigned as 1,2-anti-2,3-syn based on $^1$H NMR coupling constants. The relative stereochemistries of the remaining products in Table 4-1 were assigned by analogy to 18.

TABLE 4-2

Stereotriads from enesulfamates.

| entry | reagents | product | X | E | yield | dr |
|---|---|---|---|---|---|---|
| 1 | NBS, NaBH$_3$CN | 18 | H | Br | 71% | 12.5:1 |
| 2 | NCS, NaBH$_3$CN | 19 | H | Cl | 65%[a] | 5:1 |
| 3 | TCICA, NaBH$_3$CN | 19 | H | Cl | 76% | >19:1[b] |
| 4 | Selectfluor ®, NaBH$_3$CN | 20 | H | F | 57% | 2:1 |
| 5 | DIAD,[c] NaBH$_3$CN | 21 | H | NN(CO$_2^i$Pr)$_2$ | 69% | >19:1 |
| 6 | PhSCl, NaBH$_3$CN | 22 | H | SPh | 80% | 2.9:1[d] |
| 7 | DMDO, STABH | 23 | H | OH | 44% | 2:1[d] |
| 8 | NBS, H—≡—MgBr | 24 | ⌇—≡—H | Br | 59% | >19:1 |
| 9 | NBS, Me$_3$SiCN, cat I$_2$ | 25 | CN | Br | 73% | 3.3:1 |

[a]NMR yield using mesitylene as the internal standard.
[b]dr of the product after purification.
[c]10 mol % Cu(OTf)$_2$ and 11 mol % Me$_2$N(CH$_2$)$_2$NMe$_2$ were also added to the reaction.
[d]Minor amounts of other diastereomers were formed.

Modifying the nature of the electrophile allowed for control of the dr of the stereotriad (Table 4-2, compare entries 2 and 3). When N-chlorosuccinimide (NCS) was employed, 19 was obtained in 65% NMR yield and a dr of 5:1. However, the more electrophilic trichloroisocyanuric acid (TCICA, entry 3), improved both the yield and dr of 19 to 72% and >19:1.

Selectfluor® (entry 4) resulted in a 2:1 dr of 20, possibly due to increased epimerization at C3 caused by the electron-withdrawing fluorine. The stereochemistry of the major diastereomer could be assigned by analogy to 18 as 1,2-syn:2,3-syn; however, the identity of the minor diastereomer was believed to be 1,2-syn:2,3-anti. Nitrogen was introduced at C3 using DIAD (entry 5) to provide the vicinal diaminated stereotriad 21 in 69% yield with a dr of >19:1. PhSCl (entry 6) gave 22 in 80% yield and a dr of 2.9:1, along with minor amounts of two other stereoisomers. Reaction of 10 with DMDO (entry 7) and sodium triacetoxyborohydride (STABH) as the reductant gave 23 in lower dr, in this case due to poor facial selectivity in the addition of the electrophile to the enesulfamate. As in the case of 20, the major diastereomer was assigned by analogy to 18 and the minor diastereomer as 1,2-syn:2,3-anti by $^1$H NMR coupling constants.

The challenging generation of a complex quaternary amine-bearing carbon was accomplished by adding carbon nucleophiles to the transient iminium ion 7 according to the model proposed in Scheme 4-1. For example, employing ethynyl magnesium bromide (entry 8) in the reaction at low temperature gave 24 in >19:1 dr, while a Strecker-type reaction employing TMSCN (entry 9) gave 25 in 73% yield and a dr of 3.3:1.

The allene amination chemistry was quite flexible, as demonstrated by the conversion of a variety of heteroatom-substituted enesulfamates to the corresponding X/N/Br stereotriads (Table 4-3). Ethers, alcohols, amines, mercaptans, and halogens were all tolerated in the reaction and gave moderate to good dr of the resulting stereotriads 26-30.

TABLE 4-3

Formation of X/N/Br stereotriads.

1) 1.5 equiv NBS, solvent
2) 2.0 equiv NaBH$_3$CN

| entry | X | yield | | crude dr | isolated dr |
|---|---|---|---|---|---|
| 1 | 11 | OMe | 65% | 26 | 8:1 | 19:1 |
| 2 | 12 | OH | 71% | 27 | 5.6:1 | 4:1[a] |
| 3 | 15 | piperidine | 44% | 28 | 10:1 | 19:1 |
| 4 | 16 | SPh | 67% | 29 | >19:1 | >19:1 |
| 5 | 17 | Cl | 77%[b] | 30 | >19:1[b] | >19:1 |

[a]After attempted separation of the two diastereomers.
[b]$^1$H NMR using mesitylene as the internal standard.

The mild reaction conditions, coupled with the high chemo-, regio- and diastereoselectivity of the allene oxidation, allowed for conversion of 9 directly to X/N/Y stereotriads in a single flask (Table 4-4). A key to obtaining high dr hinged on minimizing the time that the electrophile was allowed to react with the intermediate enesulfamate (entries 1, 2). The 61% overall yield for the O/N/Br stereotriad 18 (entry 2) obtained in one pot compared favorably with the yield that was obtained when the reaction was performed in two steps (53%, Table 4-1, entry 1 and Table 4-2, entry 1). When MeOH was utilized as the nucleophile (entries 3 and 4), the dr of 26 was lower compared to that obtained by initiating the stereotriad formation from the isolated enesulfamate (see Table 4-3, entry 1), but the one-pot yield of 58% compared favorably with the two-step yield of 50%. Enantioenriched 9 (entry 5 and Scheme 4-2) gave 29 in good yield and excellent dr. The use of DIAD and PhSCl as the electrophiles with MeOH as the nucleophile (entries 5 and 6) gave 31 and 32 in 64% and 74% yields, respectively, over the four consecutive reactions.

TABLE 4-4

One-pot stereotriad synthesis.

| entry | NuH | electrophile | rxn time/temp[b] | yield | dr |
|---|---|---|---|---|---|
| 1 | AcOH | NBS | 2 h, rt | 60% 18 | 5:1 |
| 2 | AcOH | NBS | 15 min, 0° C. | 61% 18 | 20:1 |
| 3 | MeOH | NBS | 45 min, 0° C. | 60% 26 | 1.7:1 |
| 4 | MeOH | NBS | 10 min, −10° C. | 58% 26 | 2.6:1 |
| 5[c] | PhSH | NBS | 10 min, 0° C. | 61% 29 | 15:1 |
| 6 | MeOH | DIAD[d] | 2 h, 70° C. | 64% 31 | 4.6:1 |
| 7 | MeOH | PhSCl | 30 min, rt | 74% 32 | 2.6:1 |

[a]Conditions:
1a) 0.5 mol % Rh$_2$TPA$_4$, 1.1 equiv PhIO, CH$_2$Cl$_2$, rt, 1 h, then NuH
1b) electrophile, NaBH$_3$CN.
[b]time and temperature for the addition of the electrophile
[c]see Scheme 2
[d]Celite filtration before addition of the DIAD.

The ability to transfer the axial chirality of the allene to point chirality in the stereotriad is an important aspect of this chemistry. As many convenient methods are available to convert enantioenriched propargyl alcohols to the corresponding allenes, this simplifies the formation of enantioenriched stereotriads to a diastereoselective process. As illustrated in Scheme 4-2, (R)-9 was smoothly converted into (S,S,R)-29 with no erosion in the ee.

Scheme 4-2. Transfer of axial to point chirality.

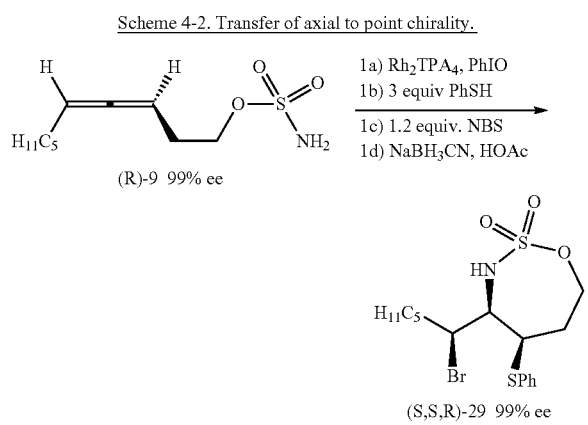

Finally, to demonstrate that the X/N/Y stereotriads could be easily deprotected (Scheme 4-3), the nitrogen of 32 (eq 2) was protected with a Boc group. Successive treatment of the N-protected 32 with Bu₄NCN and HCl provided 33 in 79% yield over the two steps.

Scheme 4-3. Deprotection of the X/N/Y stereotriads.

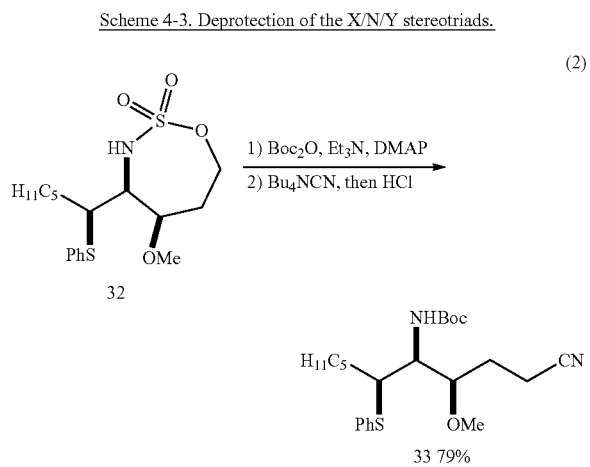

Thus, a new method for the syntheses of stereotriads containing three contiguous heteroatom-bearing carbons of the general pattern X/N/Y has been developed. These transformations utilize easily prepared sulfamoyl allenes and generally proceed with good chemo-, regio- and diastereoselectivity under mild reaction conditions. The axial chirality of an enantioenriched allene can be translated into point chirality in the product with good fidelity. The scope of the allene, the nucleophile and the electrophile, particularly in the context of generating X/N/C stereotriads and amines containing two or three contiguous quaternary carbons, are described throughout the specification.

Example 5

Allene Oxidation to N- and O-Containing Stereotriads

The potency and selectivity of bioactive molecules relies on the proper spatial orientation of a specific combination of functional groups towards its intended target. Stereodefined carbon-nitrogen bonds play an important role in determining both the binding affinity and the specificity of certain pharmacophores. These amine groups are often embedded in densely functionalized arrays of three or four contiguous stereocenters (termed "stereotriads" and "stereotetrads" in this specification). The development of general and operationally simple methods to prepare such motifs from readily accessible hydrocarbons is described in this example.

Figure 5:
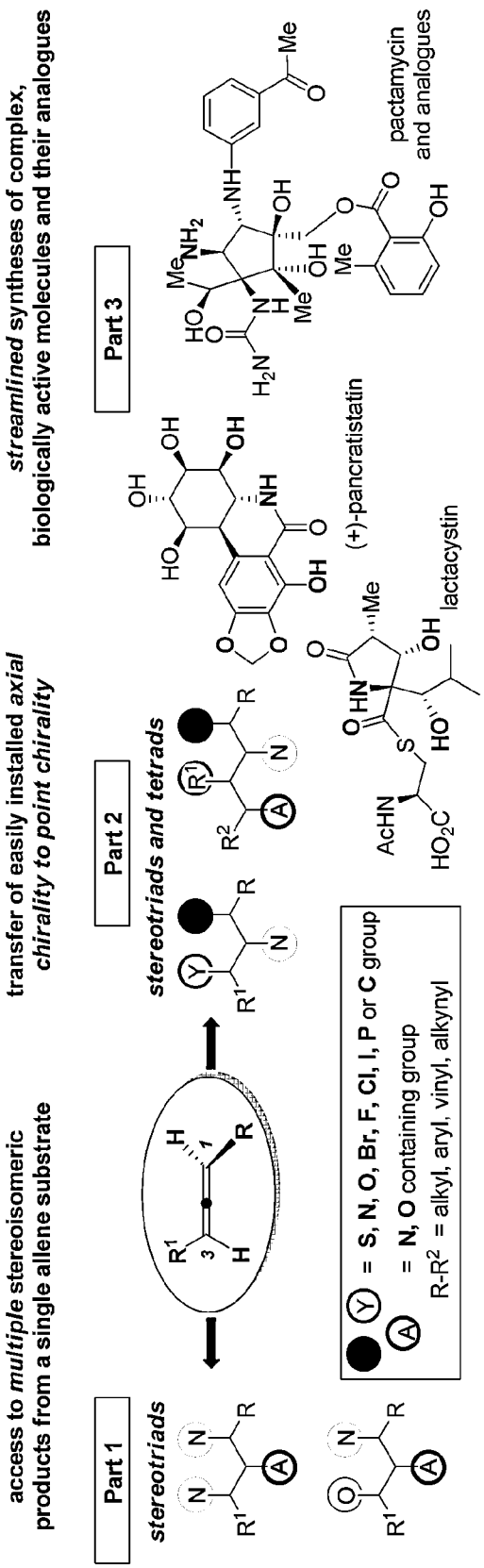
FIG. 5. New methods for allene oxidation and synthetic targets, where R, $R^1$, and $R^2$ are each independently an optionally substituted $R^1$ as described herein.

This example describes streamlined approaches to complex heteroatom-containing stereotriads and tetrads, which are difficult to obtain using currently available synthetic methodology. The significance and utility of these new methodologies can be demonstrated by the efficient syntheses of three important biologically active molecules: the protease inhibitor lactacystin, the anti-cancer agent (+)-pancratistatin and the antibiotic and antimalarial natural product pactamycin. The flexibility of this chemistry can enable preparation of unique analogues of pactamycin to initiate collaborative structure-activity relationship studies of this complex aminocyclopentitol (FIG. 5). In the various embodiments, the R, $R^1$, and $R^2$ of this example can each independently an optionally substituted $R^1$ as described in the Summary and Detailed Description above.

The stereocontrolled preparation of complex amines is far from trivial, especially when the nitrogen is contained in an array of three or more contiguous stereocenters. Typically, approaches to these motifs rely on reactions of chiral alkenes, which often results in poor regio- and stereocontrol. A method to reliably introduce multiple adjacent heteroatom-bearing chiral centers into a simple precursor in a single reaction vessel would provide a new, unified paradigm for executing the syntheses of complex amine arrays. Allenes are advantageous as hydrocarbon substrates because they are easily prepared from propargyl alcohols in either racemic or enantioenriched form; they offer the potential to introduce diverse combinations of three or four contiguous $sp^3$ stereocenters in one or two simple, stereochemically predictable synthetic manipulations; the axial chirality of an allene can be transferred to point chirality to generate diverse enantioenriched stereotriads and tetrads without the need to employ asymmetric catalysis; several diastereomeric stereotriads can potentially be obtained from a single allene through judicious choice of reaction conditions; and new allene oxidation methodologies can be used to streamline the synthesis of complex bioactive molecules and their analogues.

A key to this innovative approach lies in employing an unexplored regio-, chemo- and stereocontrolled allene aziridination to generate a highly reactive bicyclic methylene aziridine scaffold. The ring strain and differentiation of the hybridization of the two aziridine carbons in this intermediate provides the thermodynamic driving force to access a range of amine-containing stereotriads with high regio- and diastereocontrol, often in a single reaction vessel. The new methodologies for the introduction of nitrogen into allenes can provide transformative strategies for the total synthesis of densely functionalized amine motifs that occur frequently in important bioactive molecules and natural products.

Part 1: Allene oxidation to N- and O-containing stereotriads. Stereotriads containing combinations of N- and O-bearing chiral centers are prevalent in many pharmacologically useful molecules. The range and stereochemical diversity of such motifs that can be obtained from allene oxidation are described below.

Figure 6:
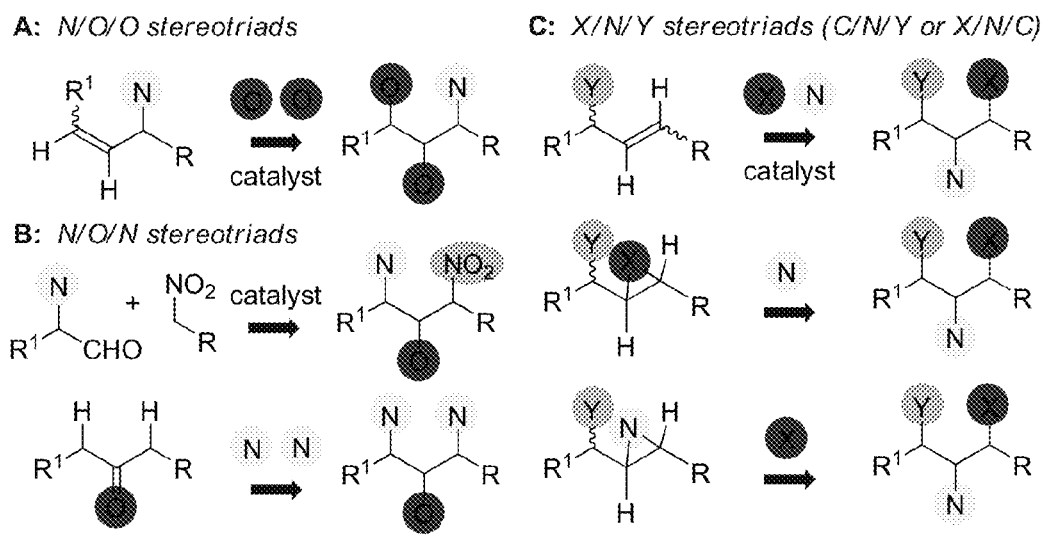
FIG. 6. Representative approaches to amine stereotriads where R, $R^1$, and $R^2$ are each independently an optionally substituted $R^1$ as described herein, and the catalyst can be a Rh catalyst as described herein.

The oxidation of chiral alkenes is among the most common ways to prepare amine-containing stereotriads (FIG. 6). While N/O/O stereotriads A are arguably the easiest targets due to lack of regiochemical issues in a dihydroxylation, the synthesis of highly substituted aminodiols is still complicated by reactivity and stereochemical issues. N/O/N motifs B are also traditionally obtained through alkene oxidation. While carbonyl compounds can serve as substrates, the methods are not general. Finally, for X/N/Y and related stereotriads in C, the regiocontrol in alkene oxidation becomes an issue, irrespective of whether a direct functionalization approach or an indirect epoxidation/aziridination, followed by nucleophilic ring-opening, is employed.

In contrast to the use of alkenes and carbonyls for stereotriad formation, allenes as precursors have received little attention, despite the potential for rapid access to complex amines. Much to our surprise, allene amination as a general strategy for the preparation of structurally complex amines had been neglected prior to the work described in this example.

In terms of feasibility, the results described herein show that the strategy to utilize allene aziridination as a key step indeed results in a range of complex amine stereotriads (Scheme 5-1).

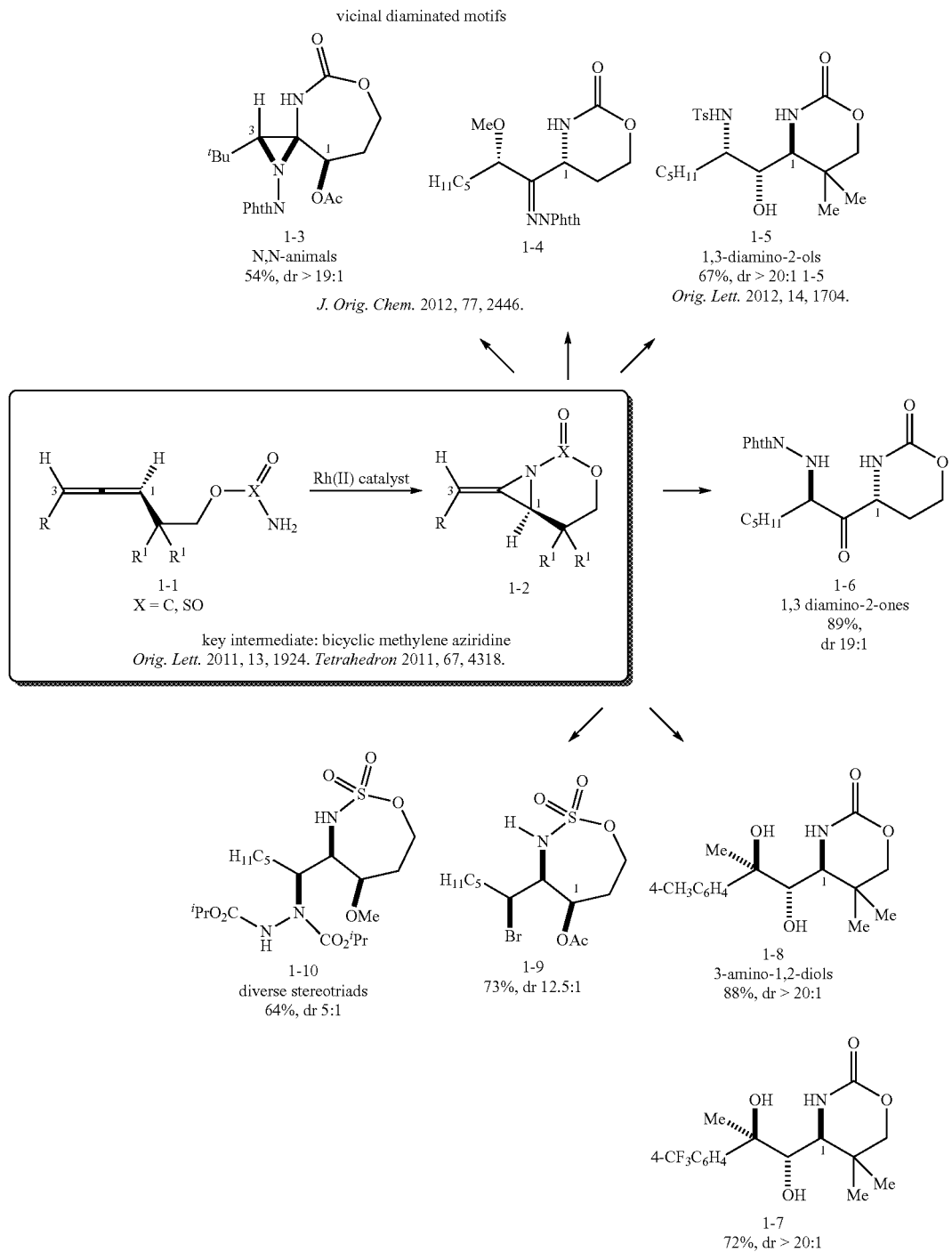

Scheme 5-1. Allene oxidation for synthesis of nitrogen-containing stereotriads.

Results. Early studies have shown that allene oxidation via aziridination (1-1 to 1-2 in Scheme 5-1) is a remarkably flexible way to construct a variety of nitrogen-containing stereotriads. Successful approaches to motifs including N,N-aminals 1-3 (X/N/N), vicinal diamines 1-4 and 1-10 (N/N/Y), 1,3-diamino-2-ols 1-5 have been devised and their precursors 1-6 (N/O/N) and 1-amino-2,3-diols 1-7 and 1-8 (N/O/O). A powerful demonstration of the range of allene oxidation has been the preparation of a series of diverse stereotriads of the form X/N/Y (1-9 and 1-10, where X, Y can be O, N, S, Br, Cl or F-containing substituents).

Allene Oxidation to N/O/O Stereotriads. Structurally complex and stereochemically dense N/N/O and N/O/N stereotriads are prevalent in many bioactive compounds (FIG. 4).

Developing predictable stereochemical models for oxidizing allenes to 1,2-anti:2,3-syn and 1,2-anti:2,3-anti N/O/O stereotriads. The installation of three new sp$^3$-heteroatom bearing carbons into an allene means there is a possibility of producing four diastereomeric pairs of enantiomers from a single racemic substrate. Understanding the factors that control the stereochemical outcome of allene aziridination and subsequent transformations allow one to select for any one diastereomer through judicious choice of reaction conditions.

Preliminary studies show that allenic carbamates, such as 2-1 (Scheme 5-2), undergo Rh(II)-catalyzed aziridination to yield predominantly E bicyclic methylene aziridines, such as 2-2. Ru-catalyzed dihydroxylation of the exocyclic alkene of 2-2 is highly diastereoselective and yields 1-amino-3-hydroxy-2-one 2-3 in dr>20:1. Careful reduction of 2-3 with NaBH$_4$ in the same pot yields the 1-amino-2,3-diol 2-4, also in >20:1 dr. The relative stereochemistry was established as 1,2-anti:2,3-syn by an X-ray crystal structure of 2-4. The high dr in 2-3 is believed to result from shielding of the top face of the alkene by the carbamate ring. Removal of the gem-dimethyl groups in 2-5 and 2-6 gave only single diastereomers (2-7 and 2-8) from the isomeric methylene aziridines. Both the hydroxyl and the amino groups of 2-9 can react with NaBH$_4$, locking the molecule into a conformation 2-10 that favors approach of the nucleophile (hydride in this case) from the top face of the carbonyl to yield 2-11. According to this model, the identities of R and R$^1$ should not greatly impact the stereochemical outcome.

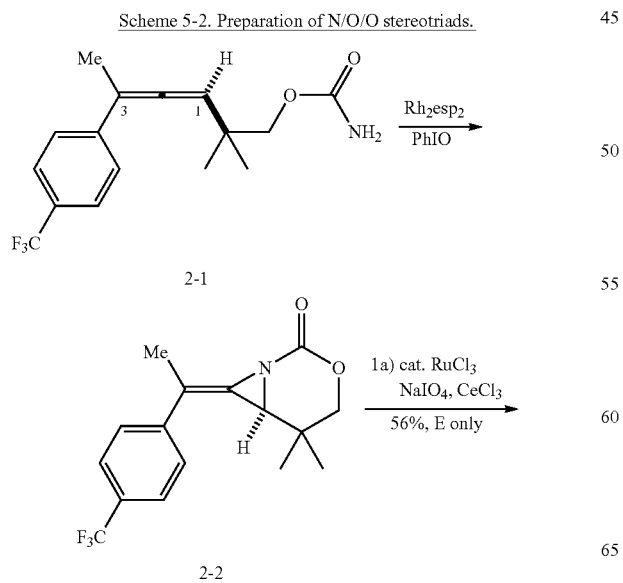

Scheme 5-2. Preparation of N/O/O stereotriads.

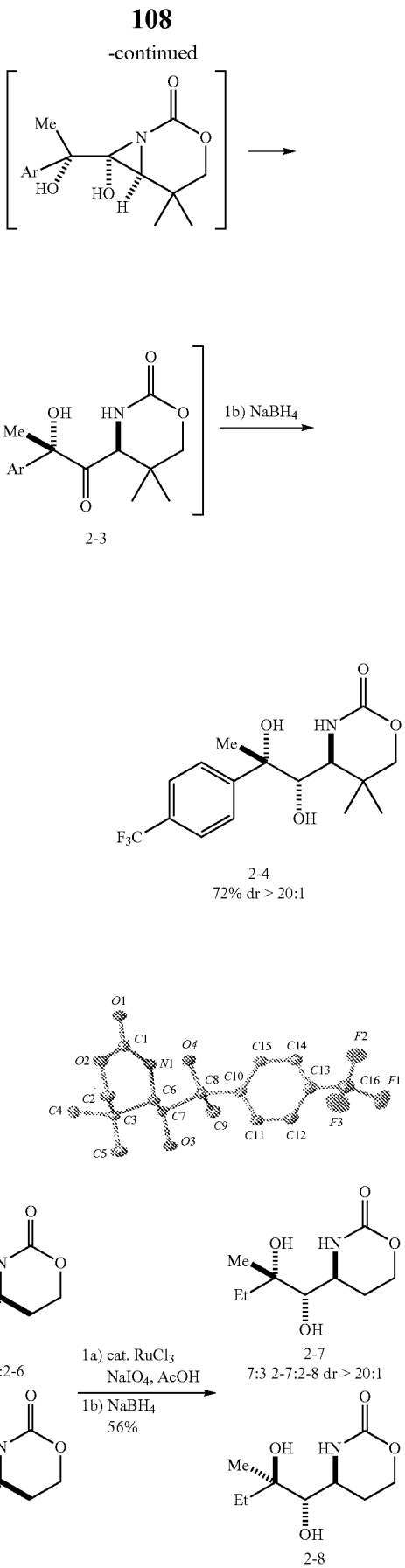

-continued stereochemical model
identity of R, R¹ is not a factor

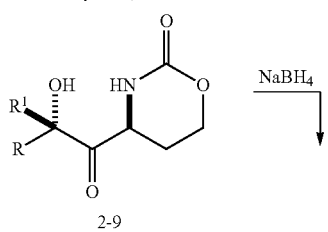
2-9

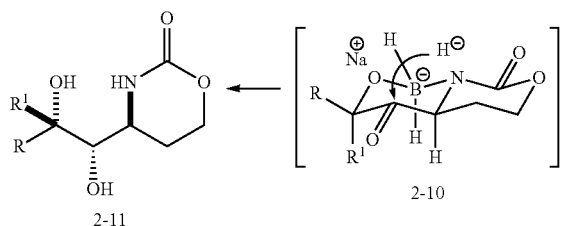
2-11 ← 2-10

Vicinal 1,2-anti-2,3-syn and 1,2-anti-2,3-anti quaternary heteroatom-bearing stereocenters. Attempts to add a series of Grignard reagents to 3-1 (Scheme 5-3, R,R¹=alkyl, aryl) resulted in a 1:1 mixture of diastereomers. The $Mg^{2+}$ ion did not appear to provide a sufficiently tight closed transition state to promote good stereocontrol. However, if another means to "lock" the 1,3-aminoalcohol into a rigid decalin conformation can be identified, the addition of carbon nucleophiles to 3-2 would yield stereotriads containing adjacent quaternary carbons similar to 3-3 in high dr. This can be achieved by organoboron compounds such as $Bu_2BOTf$ or $R_2BCl$, organosilicons ($R_2SiH_2$, $R_2SiCl_2$) and borohydride salts of the form $MB(OR)_2H_2$, where M can be Li, Na or K. Nucleophiles for the generation of the vicinal quaternary carbon centers can include Grignard reagents, allylboranes and silanes, cyanide and enolates. Both the 1,2-anti-2,3-syn and 1,2-anti-2,3-anti aminodiols can be obtained through this mode of allene aziridination. Successful transformation of a methylene aziridine such as 3-4 would yield a product 3-5 containing three contiguous, quaternary, heteroatom-bearing chiral centers. The hindrance imposed by an additional group at C1 should not greatly impact the dr of the dihydroxylation of 3-4, as the top face is still more sterically congested (geometry optimized structure 3-4a).

Scheme 5-3. Quaternary stereocenters via allene oxidation.

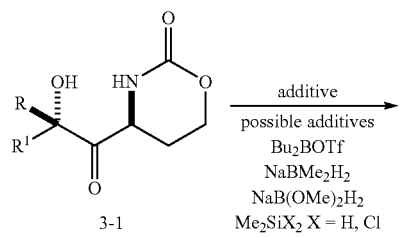

-continued

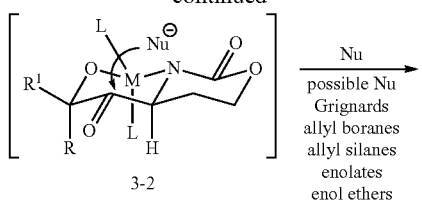
3-2 possible Nu
Grignards
allyl boranes
allyl silanes
enolates
enol ethers

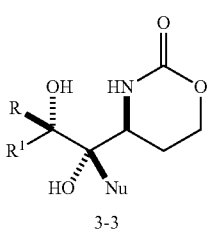
3-3

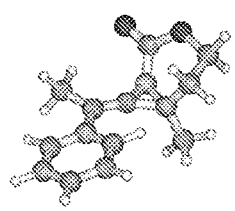
3-4a

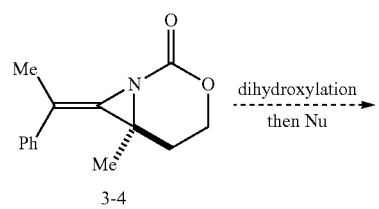
3-4 dihydroxylation
then Nu

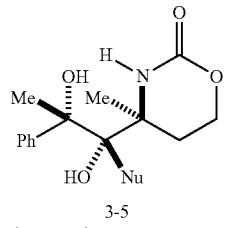
3-5
three contiguous quarternary
heteroatom-bearing stereocenters 1,2-Syn-2,3-anti and 1,2-syn-2,3-syn N/O/O stereotriads. Stereocontrolled syntheses of the remaining two diastereomeric N/O/O stereotriads 1,2-syn-2,3-anti 4-10 and 1,2-syn: 2,3-syn 4-13 require different modes of stereocontrol in the reduction of the ketones 4-4 and 4-5. Given sufficient steric differentiation between R and R¹ of 4-4, the hydroxyl group at C3 could induce chelation control to give 4-10 via 4-7. This chelation can be enhanced by the addition of oxophilic Lewis acids that would bind preferentially to the O at C3 over the N at C1. Such "hard" additives, including Brønsted acids, $Li^+$, $Na^+$, $BF_3OEt_2$ and $ZnCl_2$, can be combined with a reductant to favor generation of the 1,2-syn-2,3-anti diastereomer 4-10. The use of azaphilic additives ($Zn(OTf)_2$, $Ag^+$, $Cu(OTf)_2$) can favor the production of 4-6 and can be useful if $NaBH_4$ fails to give good dr in more complex substrates.

Scheme 5-4. Diastereomic 3-amino-1,2-diols.

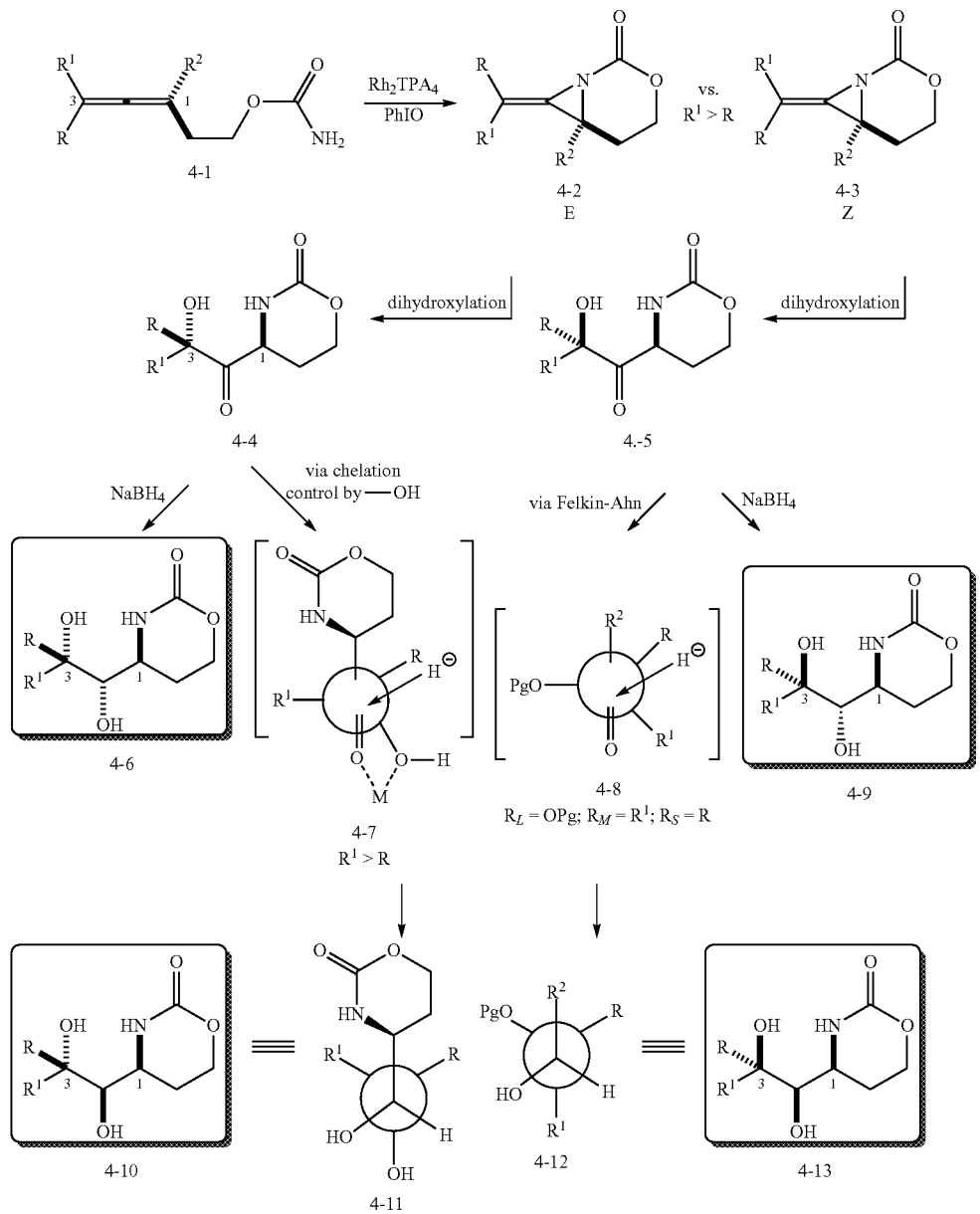

The 1,2-syn:2,3-syn diastereomer 4-13 is favored when Felkin-Ahn stereocontrol involving the substituents at C3 dominates in the reduction of ketone 4-5. Installation of a bulky protecting group on the OH group, such as trityl or diphenyl-tert-butylsilyl, can serve to discourage any competing chelation. The role the substituents on C1 play in determining the stereochemical outcome of the reduction have to be determined empirically by exploring the substrate scope of the bicyclic methylene aziridines in the dihydroxylation/reduction reaction.

Another challenge in the syntheses of 1,2-anti-2,3-anti and 1,2-syn-2,3-syn N/O/O stereotriads 4-9 and 4-13 is a Z-selective allene aziridination catalyst. $Rh_2(OAc)_4$ yields significant amounts of the Z methylene aziridine (ca. 50%). As an alternative approach, the E bicyclic methylene aziridine 5-2 can be epoxidized to the reactive 5-3 with high facial selectivity (Scheme 5-5). Selective ring-opening at C3 can give ketone 5-4, effectively inverting the stereochemistry at C3. The appropriate reduction can then yield either the 1,2-anti:2,3-anti 5-5 by the model of 2-10 or the 1,2-syn:2,3-syn 5-6 from Felkin-Ahn control by C3.

Scheme 5-5. 1,2-syn-2,3-anti and 1,2-syn-2,3-syn and N/O/O stereotriads from E-methylene aziridines.

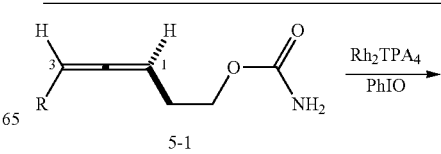

5-1

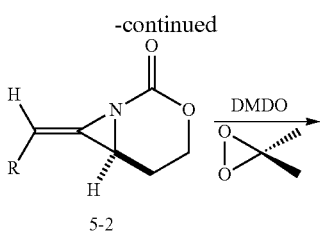

5-2

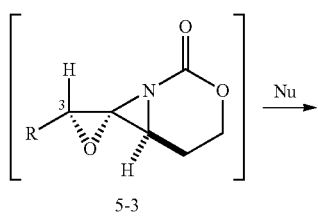

5-3

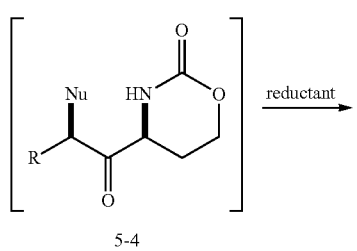

5-4

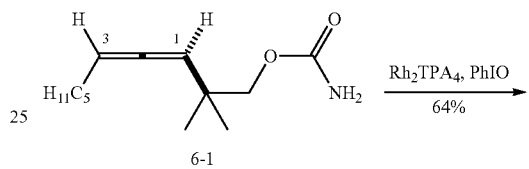

5-5 (4-9)   5-6 (4-13)

Allene Oxidation to N/O/N Stereotriads. Bicyclic methylene aziridines undergo regioselective aminohydroxylation, followed by reduction, to yield 1,3-diamino-2-ol motifs valuable for the construction of cholesterol-lowering statins, antibiotic aminoglycosides and protease inhibitors (FIG. 4). Both 6-2 and 6-4 (Scheme 5-6) were smoothly transformed into the 1,3-diamino-2-ols 6-3 and 6-5 with high regio- and diastereoselectivity. In contrast to the dihydroxylation of bicyclic methylene aziridines, removal of the gem dimethyl groups in 6-6 decreased the dr in the reduction of the ketone to 1.7:1 in 6-7. The electron-withdrawing sulfonamide group at C3 may make binding both the N and the O to $NaBH_4$ slower than the background reduction. Pre-formation of a diazaborolidine or a structure similar to 6-9 can improve stereocontrol in the reduction of 1,3-aminohydroxy-2-ones with both hydrides and carbon nucleophiles.

Allene Oxidation to N/N/O and N/N/N Stereotriads. The flexibility of allene oxidation can be further extended to include the preparation of N/N/N and N/N/O stereotriads from the 1,3-diamino-2-one 7-1 and 1-amino-3-hydroxy-2-one 7-2 intermediates that arise from aminohydroxylationand dihydroxylation of bicyclic methylene aziridines, respectively (Schemes 5-2 and 5-6). The stereochemical models developed for the ketone reduction can be applicable to reductive amination (7-3). This can provide the 1,2-anti:2,3-syn triamines 7-4 and the 1,2-anti:2,3-syn diamino alcohols 7-5 (Scheme 5-7).

Scheme 5-6. 1,3 Diamino-2-ols via aminohydroxylation of allenes.

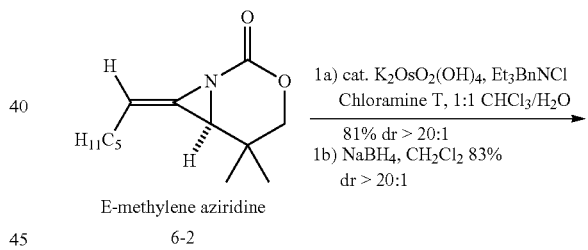

6-1

E-methylene aziridine
6-2

1a) cat. $K_2OsO_2(OH)_4$, $Et_3BnNCl$
Chloramine T, 1:1 $CHCl_3/H_2O$
81% dr > 20:1
1b) $NaBH_4$, $CH_2Cl_2$ 83%
dr > 20:1

6-3

Z-methylene aziridine
6-4

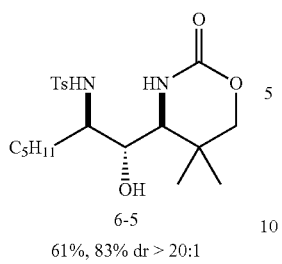
6-5
61%, 83% dr > 20:1
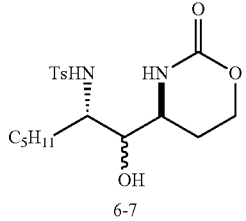
6-7
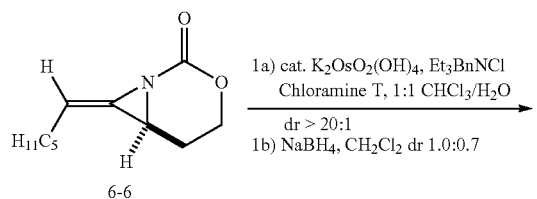
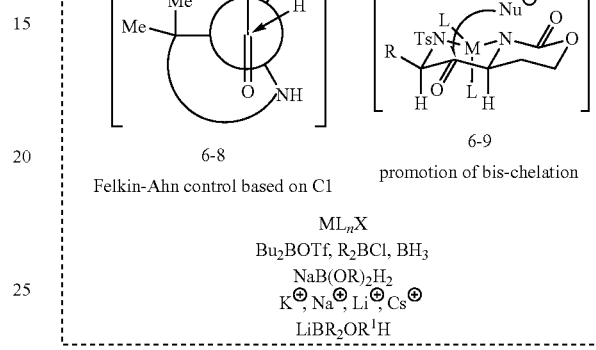
6-8
Felkin-Ahn control based on C1
6-9
promotion of bis-chelation
$ML_nX$
$Bu_2BOTf$, $R_2BCl$, $BH_3$
$NaB(OR)_2H_2$
$K^⊕$, $Na^⊕$, $Li^⊕$, $Cs^⊕$
$LiBR_2OR^1H$
Scheme 5-7. N/N/O and N/N/N stereotriads.
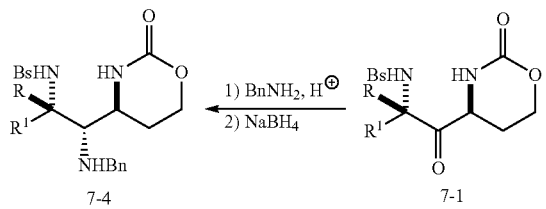
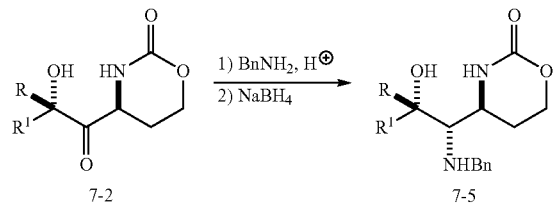
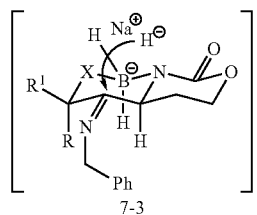
7-3

Thus, this example describes the ability to prepare complex nitrogen-containing synthetic motifs (N/O/O, N/O/N, N/N/O and N/N/N stereotriads) in a rapid and stereocontrolled fashion from allenes, and describes the general reactivity of bicyclic methylene aziridine scaffolds.

Part 2: Flexible preparation of more diverse stereotriads and tetrads from allenes and applications to the synthesis of lactacystin and (+)-pancratistatin. The analysis below describes the expansion of the range and stereochemical diversity of the motifs that can be obtained using the key allene aziridination strategy, focusing on the nucleophilic ring-openings of bicyclic methylene aziridines and their subsequent transformations to X/N/Y and C/N/Y stereotriads and related X/N/C/Y stereotetrads.

Numerous important natural products contain complex amine stereotriads of an X/N/Y or C/N/Y pattern, where X and Y is, for example, a N, O, S or halogen group (FIG. 4). In Part 1 above, the reactions focused on the double bond of a bicyclic methylene aziridine resulting from allene aziridination to provide N/O/O, N/O/N, N/N/O and N/N/N stereotriads. That approach was amenable for introducing O and N heteroatoms. This part describes nucleophilic ring-opening of methylene aziridines, followed by reaction of the resulting enamines, to introduce diverse heteroatoms into stereotriads.

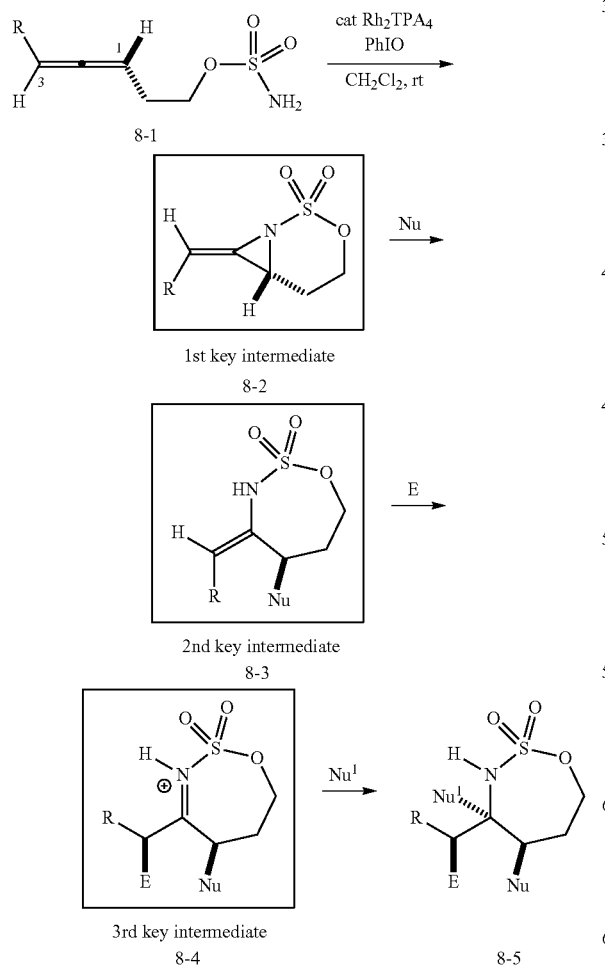

Scheme 5-8.
Synthesis of diverse stereotriads via allene aziridination as a key step.

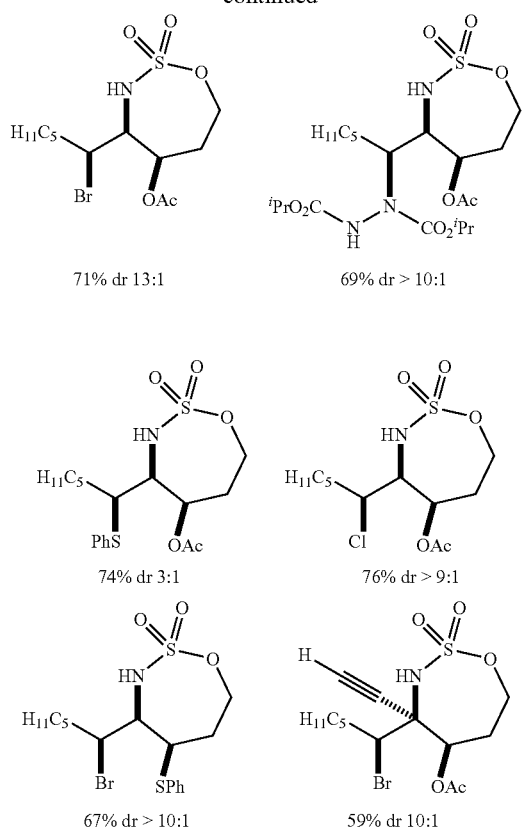

Results. The strategy of Scheme 5-8 was very successful and contains three different points in the synthetic sequence (8-2, 8-3, 8-4) where diversity can be introduced into the stereotriad. Other key results are shown in Scheme 5-9. As shown in eq 1, 9-1 can be converted to the X/N/Y stereotriad 9-2 in a single reaction vessel with good yield and excellent dr. The ability to deprotect the stereotriads is also important and eq 2 illustrates one of several ways to achieve this result. Finally, the ability to transfer the axial chirality of (R)-9-1 to point chirality in (S,S,R)-9-5 with excellent fidelity was verified.

Scheme 5-9. Key results for X/N/Y stereotriads.

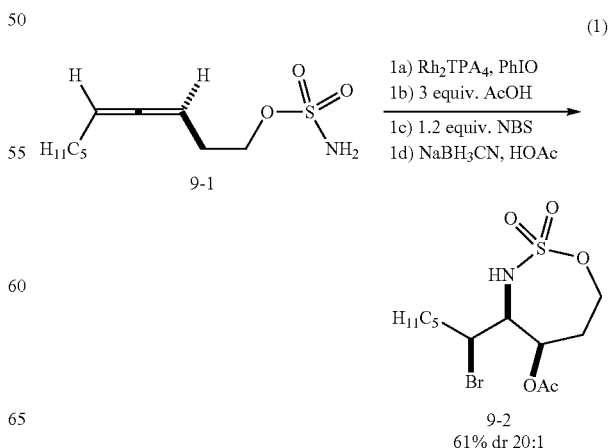

-continued (2)

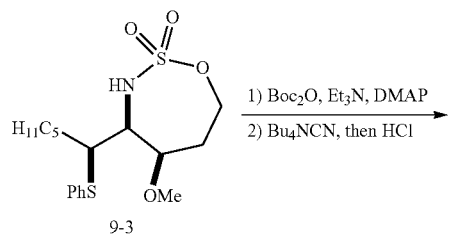

9-3

1) Boc₂O, Et₃N, DMAP
2) Bu₄NCN, then HCl

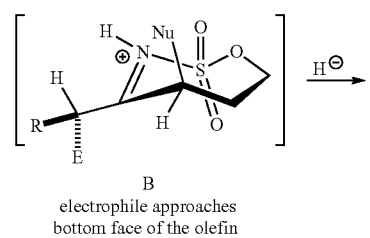

9-4
79% dr 20:1

(3)

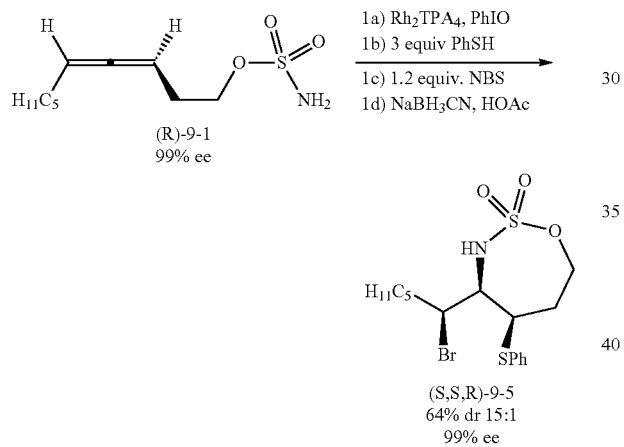

(R)-9-1
99% ee

1a) Rh₂TPA₄, PhIO
1b) 3 equiv PhSH
1c) 1.2 equiv. NBS
1d) NaBH₃CN, HOAc (S,S,R)-9-5
64% dr 15:1
99% ee Allene Oxidation to X/N/Y Stereotriads. Developing predictable stereochemical models for 1,2-syn:2,3-syn and 1,2-anti:2,3-anti X/N/Y stereotriads. Allenes can be transformed to a variety of X/N/Y stereotriads using the approach shown in Scheme 5-8. Interestingly, the major product contained the 1,2-syn:2,3-syn stereochemistry. This understanding of the factors controlling this stereochemical outcome allows access to the other three possible diastereomers of a given stereotriad.

The preference for the 1,2-syn-2,3-syn isomer 10-2 (Scheme 5-10) is consistent with A undergoing a conformational change to relieve $A^{1,3}$ strain. This places the Nu above the plane of the alkene, prompting the electrophile to approach from the more accessible bottom face, yielding B. Attack of the final nucleophile from the bottom face of the iminium ion then results in the observed 1,2-syn:2,3-syn 10-2. If the 1,2-anti-2,3-anti isomer 10-4 is desired, substrate control in the reduction step must be overridden. This can be accomplished through a directed, intramolecular delivery of the hydride to the iminium ion using an adjacent hydroxyl or amine group. Suitable reductants can include Red-Al, (RO)₂BH₂ and LiBH₄.

Scheme 5-10. 1,2-Syn:2,3-syn and 1,2-anti:2,3-anti X/N/Y motifs.

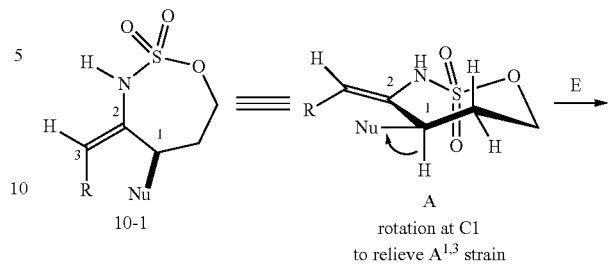

10-1

A
rotation at C1
to relieve $A^{1,3}$ strain

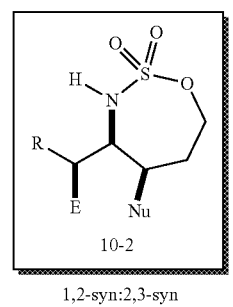

B
electrophile approaches
bottom face of the olefin

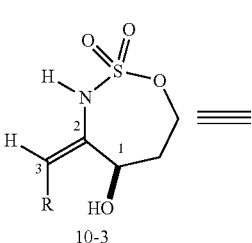

10-2
1,2-syn:2,3-syn 10-3

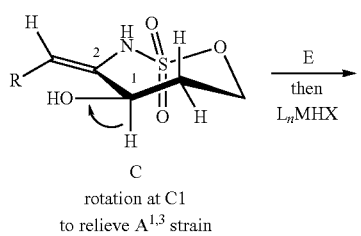

C
rotation at C1
to relieve $A^{1,3}$ strain

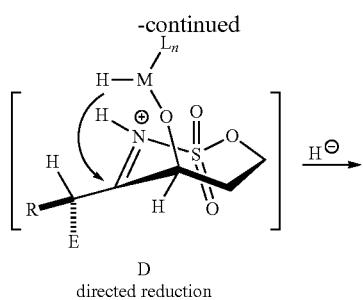

D
directed reduction

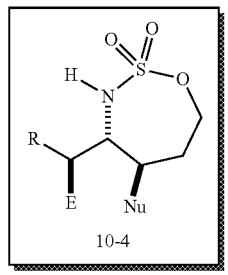

10-4
1,2-anti:2,3-anti

Preparation of 1,2-syn-2,3-anti and 1,2-anti-2,3-syn X/N/Y stereotriads. A straightforward approach to the remaining 1,2-syn:2,3-anti and 1,2-anti:2,3-syn diastereomers 11-7 and 11-9 can be achieved by accessing the bicyclic methylene aziridine 11-2. The E enesulfamate 11-1 can be isomerized to the Z enesulfamate 11-2 using N-iodosuccinimide/NaBH$_3$CN via 11-4. According to the stereochemical model outlined in Scheme 5-10, the lack of significant A$^{1,3}$ strain in 11-3 can allow the electrophile to approach from either the top or bottom face of the enesulfamate, leading to both 11-5a and 11-5b. The model also predicts that relief of A$^{1,3}$ strain in the iminium ion intermediates 11-5a and 11-5b can promote reduction from the bottom face in both cases, leading to the all syn product 10-2 (Scheme 5-10) and the desired 1,2-syn-2,3-anti product 11-7. Additional substitution in the tether between the allene and the sulfamate to discourage approach of electrophiles from the top face of the alkene can provide good dr in the reactions of Z-enesulfamates. Also, 1,3,3-trisubstituted allenes can be successful substrates because they provide the necessary A$^{1,3}$ strain in 11-3 for good dr.

Scheme 5-11. 1,2-Syn:2,3-anti and 1,2-anti:2,3-syn X/N/Y motifs.

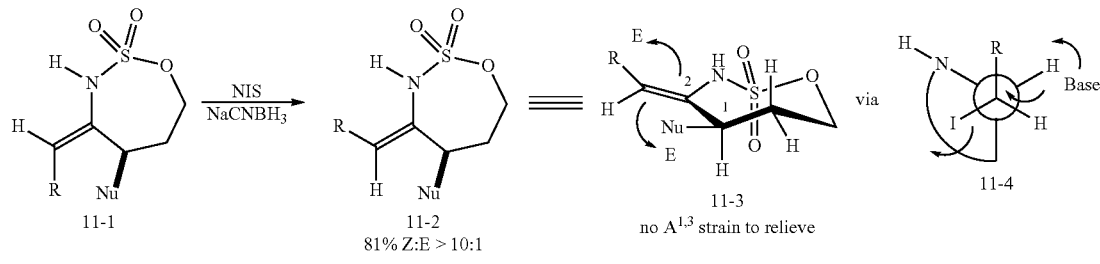

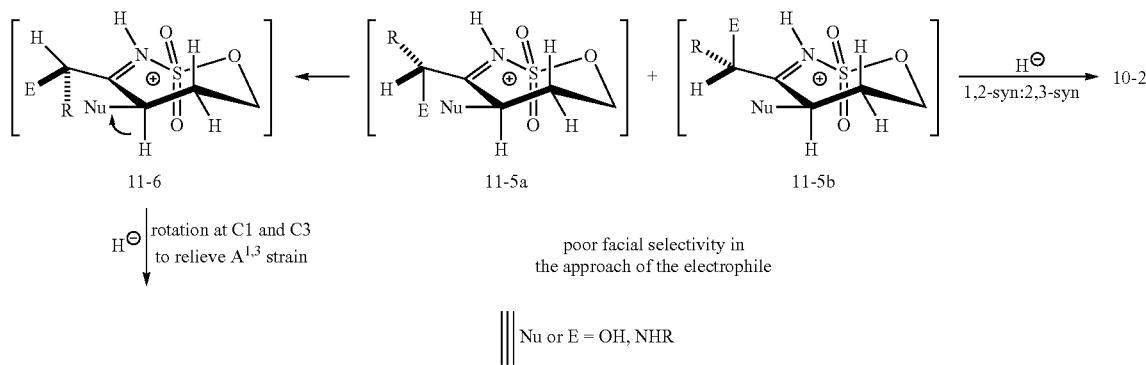

Nu or E = OH, NHR

-continued

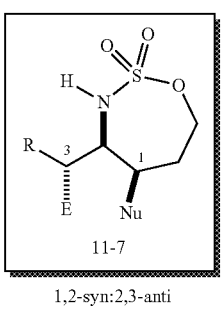

11-7
1,2-syn:2,3-anti

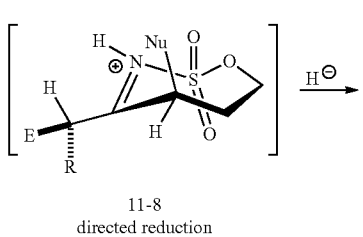

11-8
directed reduction

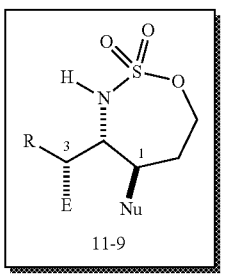

11-9
1,2-anti:2,3-syn

Obtaining the 1,2-anti:2,3-syn diastereomer 11-9 from the Z-enesulfamate is challenging because substrate control in both the electrophilic addition and reduction steps must be substantially overridden. Thus, an alternative approach can be more suitable (Scheme 5-12) in certain circumstances. Treatment of a Nu/N/Br stereotriad 12-1 (easily obtained as shown in Scheme 5-8) with a base can form an intermediate aziridine 12-2. Depending on the substitution pattern of 12-2, it can be opened with a nucleophile at C2 to yield the desired 1,2-anti:2,3-syn product 12-4 or at C3 to give the all syn 12-6. In the latter case, this permits the introduction of diverse heteroatoms at C3 using a nucleophile instead of an electrophile. Finally, direct $S_N2$ displacement of a secondary halide in 12-1 can be used for the synthesis of 1,2-syn:2,3-anti isomers 12-5. These reactions provide a series of predictable and selective methods to secure any one of the four possible diastereomers for a given stereotriad.

ring-opening of the bicyclic methylene aziridine, including F, Cl, Br, $CF_3$ and P-based anions and those based on O, N containing easily unmasked protecting groups can be used. Additional electrophilic sources of F, Cl, Br, I, N, O, S and P and other nucleophiles for addition to the iminium ion intermediate can also be used (e.g., Grignard and organozinc reagents, cyanide, allylsilanes and boranes, enolates, enamines). Current results (Scheme 5-9, eq 1) show that allene oxidation to form the X/N/Y stereotriad can be carried out in a single pot.

Total synthesis of lactacystin. The proteolytic degradation of cellular proteins is a crucial biological process. In particular, the breakdown of ubiquitinated proteins by the 20S proteasome plays a key role in regulating transcription factors and cell division. Diseases, including cancer and neurodegenerative disorders, can arise from malfunctions in the ubiquitin-proteasome system. As a result, proteasome inhibitors Scheme 5-12. Alternative approaches to the synthesis of 1,2-syn:2,3-anti and 1,2-anti:2,3-syn stereotriads.

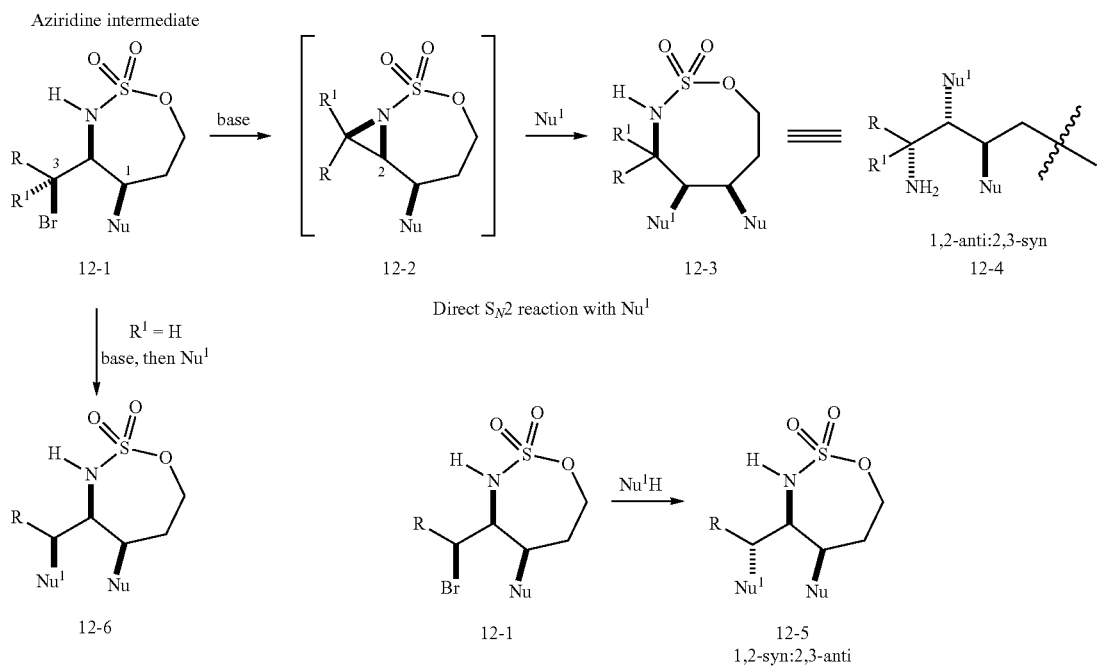

Expansion of the scope of heteroatom-containing nucleophiles and electrophiles for the synthesis of X/N/Y stereotriads. As illustrated in Scheme 5-8, there are three points of diversity in the approach to the preparation of X/N/Y stereotriads from allenes. A broader range of nucleophiles for the have received intense interest from the synthetic community. Lactacystin was the first natural 20S proteasome inhibitor to be identified and was isolated from the *Streptomyces* sp. in 1991. This "touchstone" molecule, for which several syntheses have been reported, would be suitable for a quick demonstration of the utility of allene aziridination in total synthesis prior to pursuing other targets.

The retrosynthesis shown in Scheme 5-13 installs the thioester side chain of lactacystin 13-1 as the penultimate step, a transformation that is well-precedented. The γ-lactam core of 13-1 arises from a Ru-catalyzed oxidation of a pyrrolidine 13-2. This heterocycle can be generated via a NaI-mediated ring-opening of the sulfamate 13-3, followed by intramolecular cyclization to the pyrrolidine. The sulfamate 13-3 can be accessible in a single pot from the enantioenriched allene 13-4, based on the precedent established in the inventors' earlier studies.

Scheme 5-13. Retrosynthesis for (+)-lactacystin using allene oxidation.

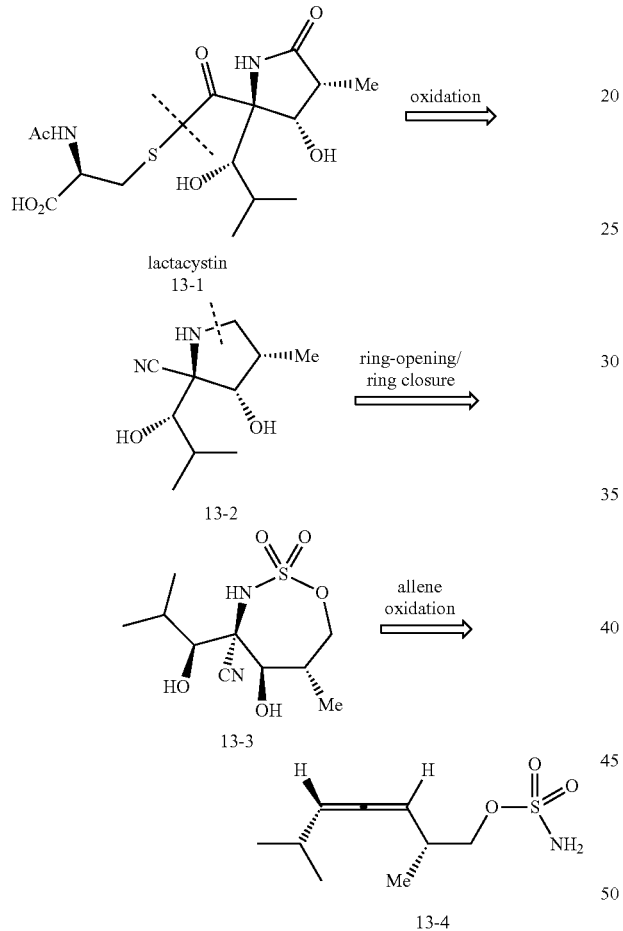

The forward synthesis can begin with allene 14-1 (Scheme 5-14), formed in four steps from an alkynyl ketone. Compound 14-1 can be subjected to aziridination and can yield 14-2a as a single stereoisomer. Ring-opening with AcOH, followed by treatment with DMDO can result in an iminium ion 14-2c, which can engage in a modified Strecker reaction to give 14-3. Results suggest the dr of 14-3 should be at least 3:1 (see Scheme 5-8), but increasing the electrophilicity of the dioxirane can improve the selectivity. Standard protections, followed by precedented ring-opening of the cyclic sulfamate with NaI and triggering of ring-closure with NaH, can lead to the pyrrolidine 14-4. Reaction of 14-4 with Red-Al reduces the nitrile to an aldehyde and removes the acetate protecting group from the hydroxyl group at C1. Subsequent treatment with catalytic RuCl₃ in the presence of an oxidant can accomplish four transformations in a single pot: the precedented conversion of the pyrrolidine to the lactam and oxidations of the benzyl to a benzoate, the alcohol to a ketone and the aldehyde to a carboxylic acid to give 14-5.

Scheme 5-14. Proposed total synthesis of (+)-lactacystin utilizing allene oxidation as a key step.

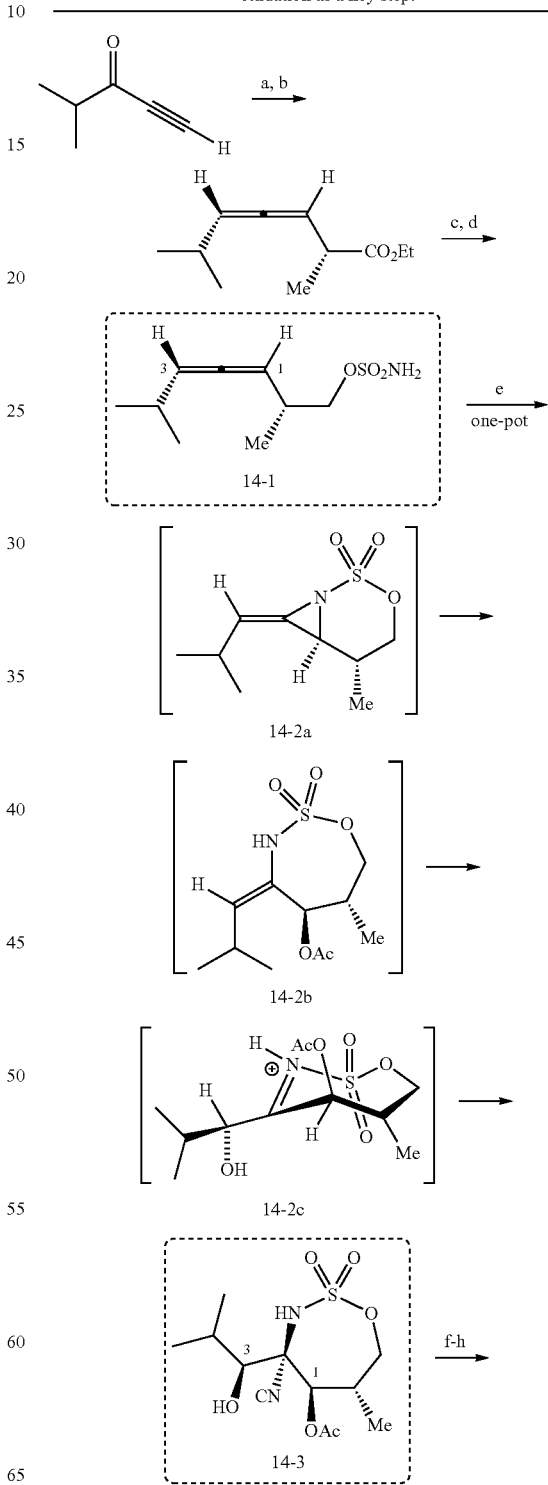

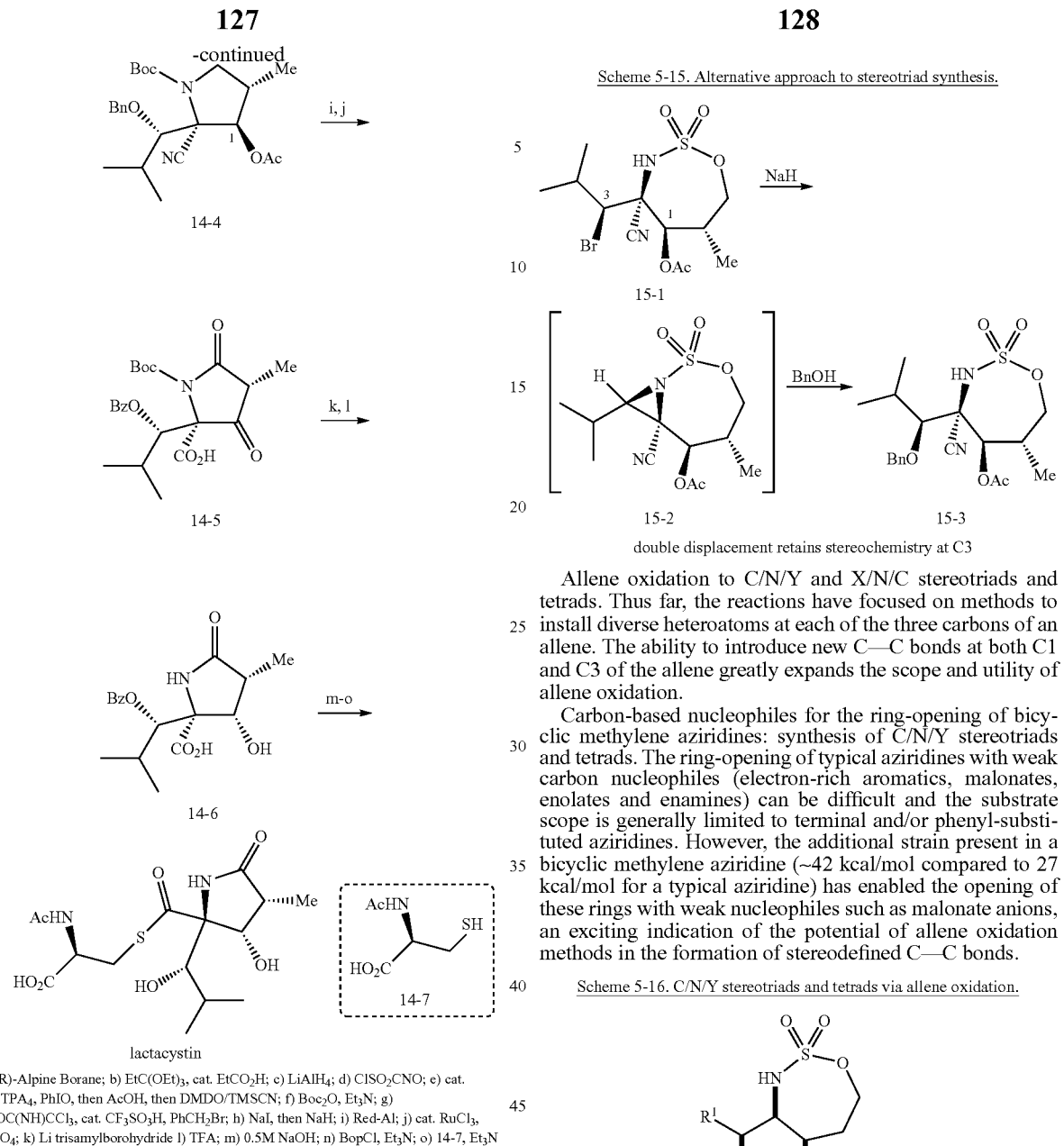

a) (R)-Alpine Borane; b) EtC(OEt)$_3$, cat. EtCO$_2$H; c) LiAlH$_4$; d) ClSO$_2$CNO; e) cat. Rh$_2$TPA$_4$, PhIO, then AcOH, then DMDO/TMSCN; f) Boc$_2$O, Et$_3$N; g) BnOC(NH)CCl$_3$, cat. CF$_3$SO$_3$H, PhCH$_2$Br; h) NaI, then NaH; i) Red-Al; j) cat. RuCl$_3$, NaIO$_4$; k) Li trisamylborohydride l) TFA; m) 0.5M NaOH; n) BopCl, Et$_3$N; o) 14-7, Et$_3$N The final sequence of steps involves substrate-controlled reduction of the ketone and deprotection to 14-6, followed by well-precedented transformations to the target lactacystin. The overall sequence can be carried out in 11 steps from the key allene substrate 14-1 and 15 steps from an inexpensive commercial starting material. In addition to being shorter than most existing syntheses, the approach uses an inherently more flexible strategy that does not rely on substrates from the chiral pool.

An alternative strategy can be invoked if the use of DMDO as the electrophile leads to low dr in the allene oxidation (Scheme 5-15). Installation of a Br at C3, which occurs in dr>20:1, can provide 15-1. Treatment of this stereotriad with NaH can trigger formation of the aziridine 15-2, which can be opened with BnOH in a double displacement reaction to retain the original stereochemistry at C3 of 15-3. A similar transformation using MeOH as the nucleophile provided an OAc/N/Br stereotriad in 10:1 dr with retention of the C3 stereochemistry.

Scheme 5-15. Alternative approach to stereotriad synthesis.

double displacement retains stereochemistry at C3

Allene oxidation to C/N/Y and X/N/C stereotriads and tetrads. Thus far, the reactions have focused on methods to install diverse heteroatoms at each of the three carbons of an allene. The ability to introduce new C—C bonds at both C1 and C3 of the allene greatly expands the scope and utility of allene oxidation.

Carbon-based nucleophiles for the ring-opening of bicyclic methylene aziridines: synthesis of C/N/Y stereotriads and tetrads. The ring-opening of typical aziridines with weak carbon nucleophiles (electron-rich aromatics, malonates, enolates and enamines) can be difficult and the substrate scope is generally limited to terminal and/or phenyl-substituted aziridines. However, the additional strain present in a bicyclic methylene aziridine (~42 kcal/mol compared to 27 kcal/mol for a typical aziridine) has enabled the opening of these rings with weak nucleophiles such as malonate anions, an exciting indication of the potential of allene oxidation methods in the formation of stereodefined C—C bonds.

Scheme 5-16. C/N/Y stereotriads and tetrads via allene oxidation.

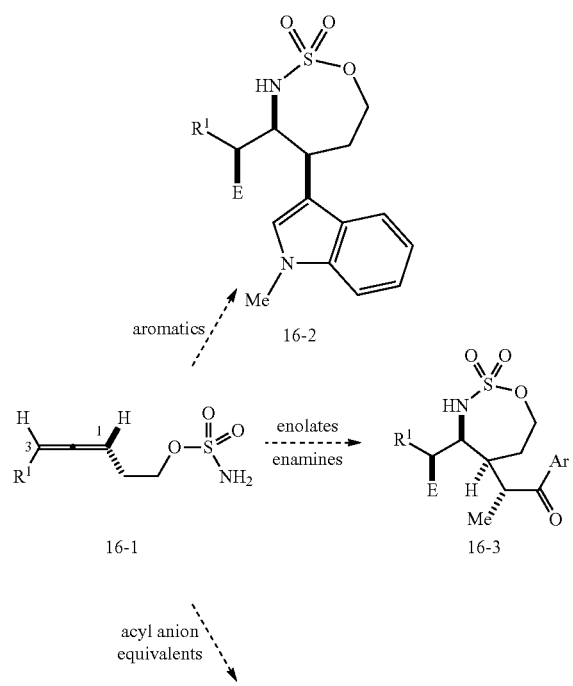

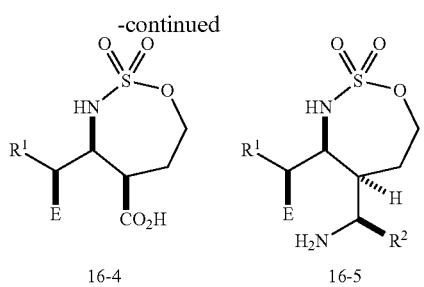

16-4

16-5

Carbon nucleophiles can lead to useful motifs for total syntheses (Scheme 5-16). This includes indoles en route to the preparation of hexahydropyrrolo[2,3-b]indoles via 16-2, electron-rich benzenes for the synthesis of (+)-pancratistatin, enolates and enamines leading to stereotetrads of the form 16-3, and acyl anion equivalents that can yield unnatural amino acids or 1,3-diamine motifs from 16-4 and 16-5.

X/N/C/N and X/N/C/O stereotetrads using electrophilic carbon species. Enesulfamates 17-1 and enecarbamates are produced by ring-opening of methylene aziridines. Reaction of these nucleophilic species with carbon electrophiles can offer access to aminated stereotetrads in high dr. An open transition state (Scheme 5-17) can provide access to all 8 possible diastereomeric stereotetrads, depending on the geometry of 17-1 or 17-7 (which can be controlled; see Schemes 5-10 and 5-11), the identity of the Lewis acid, and the conditions used to reduce the intermediate imines 17-3 and 17-5. These studies provide valuable information about stereocontrol in the reactions of cyclic enecarbamates and sulfamates with aldehydes and other carbon-based electrophiles, including imines/iminium ions, Michael acceptors and oxonium ions.

Scheme 5-17. Synthesis of stereotetrads via an open transition state.

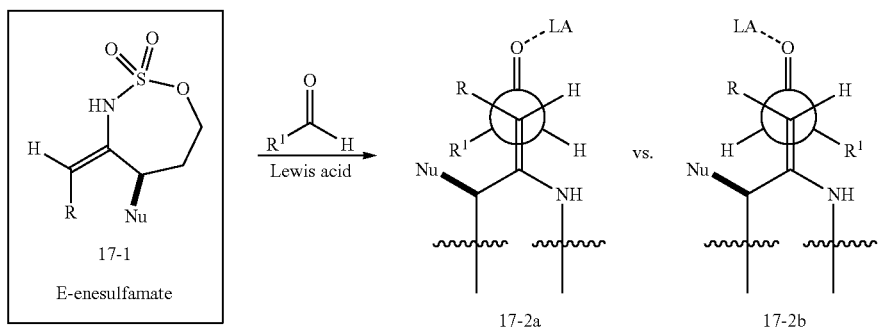

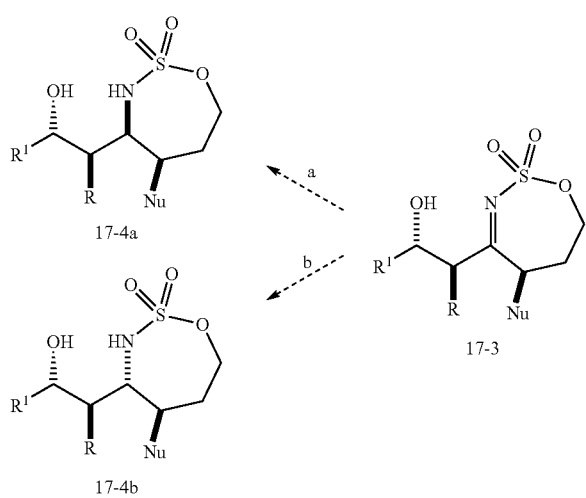

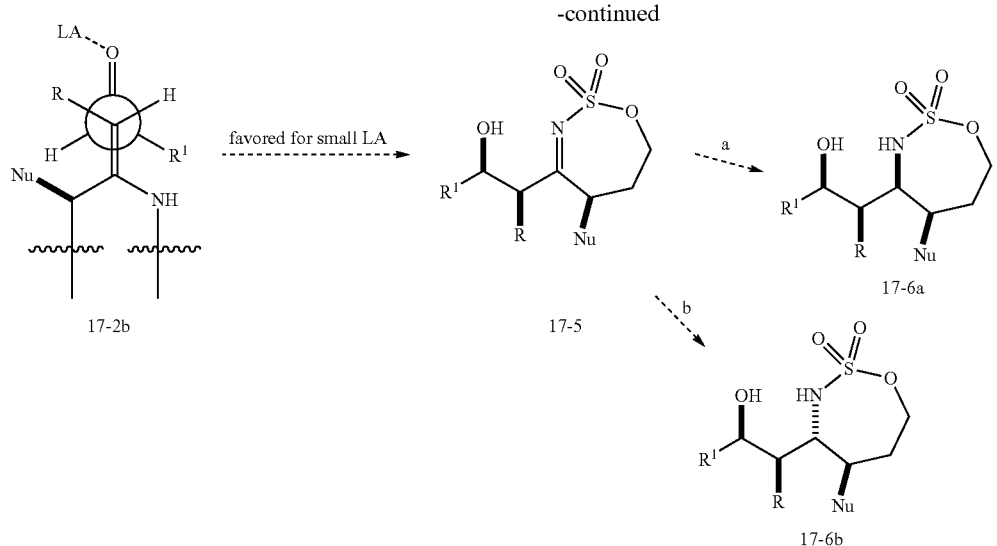

Total synthesis of (+)-pancratistatin. Pancratistatin was isolated in 1984 from the bulbs of the Hawaiian flower *Hymenocallis littoralis*. It has received intense interest due to its strong in vivo activity against cancer cell growth, as well as its potent antiviral and antiparasitic properties. Unfortunately, minimal quantities of the material can be obtained from the natural source and no synthetic route to date has been of sufficient simplicity to allow for the preparation of useful amounts of material. A synthetic sequence to (+)-pancratistatin using allene oxidation as a key step to form the stereotriad outlined is shown in Scheme 5-18. The lactam of 18-1 can be formed from a precedented modified Bischler-Naperialski reaction of a precursor similar to 18-2, while the carbocycle of 18-2 can arise from a ring-closing metathesis. The bis-alkene employed for the RCM reaction can arise from functional group manipulations of 18-3. Cyclic sulfamate 18-3 can result from the application of our methodology to oxidation of the enantioenriched allene 18-4, using an electron-rich aromatic as the nucleophile to open the key bicyclic methylene aziridine intermediate.

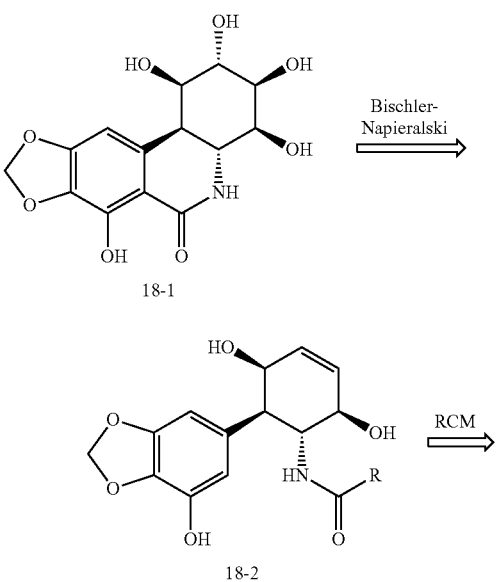

Scheme 5-18. Retrosynthesis of (+)-pancratistatin.

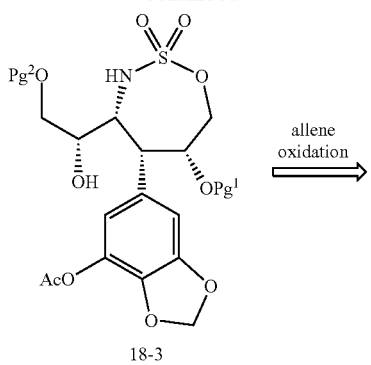

18-3

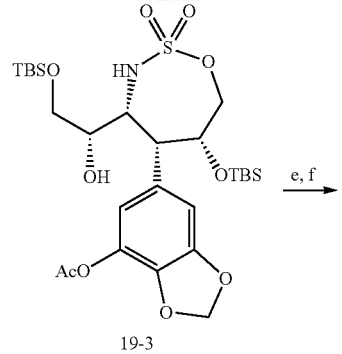

19-3

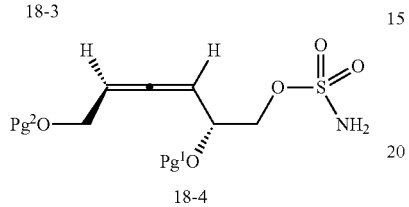

18-4

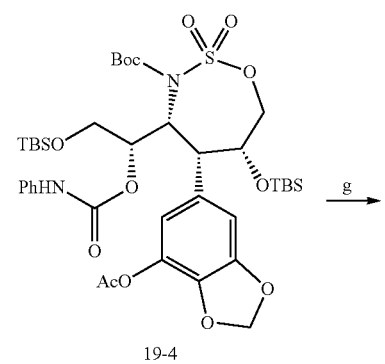

19-4

In the forward synthesis (Scheme 5-19), 19-1 can be prepared in three steps from a chiral propargyl alcohol. Application of the methodology described herein to 19-1 using 19-2 as the nucleophile yields 19-3. If regiocontrol in the addition of 19-2 to the bicyclic methylene aziridine proves problematic, steric and/or electronic manipulation of the protecting groups on the aromatic ring can be explored to favor the desired isomer of 19-3. Straightforward transformations can provide 19-6 for the ring-closing metathesis to the cyclohexene. There is literature precedent to support the ring-closure of a doubly allylic diene using a variety of Grubbs' catalysts. Diastereoselective epoxidation and HClO$_4$-mediated intramolecular ring-opening by the carbamate oxygen can supply 19-7. The penultimate step can be a modified Bischler-Napieralski cyclization to the lactam via an isocyanate intermediate. Regioisomeric mixtures from attack by either b or c may result, but literature precedent indicates a more electron-donating protecting group at the phenol a will favor production of the desired regioisomer 19-8. A global deprotection reveals (+)-pancratistatin.

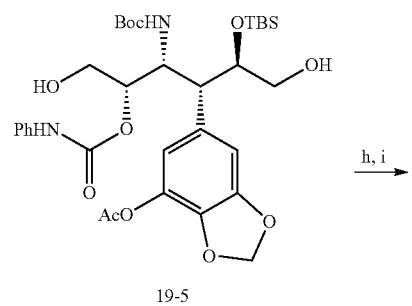

19-5

Scheme 5-19. Proposed total synthesis of (+)-pancratistatin.

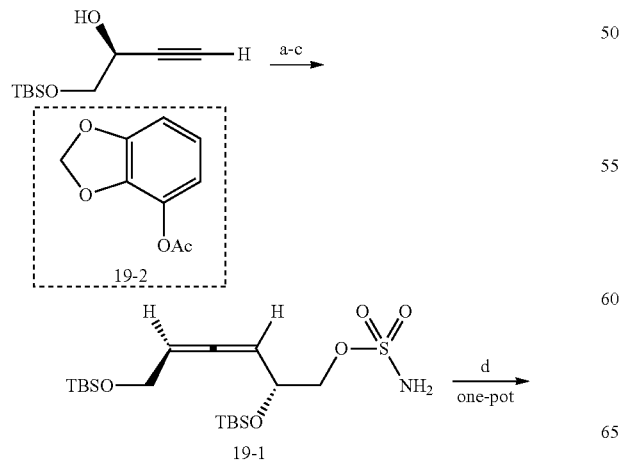

19-1

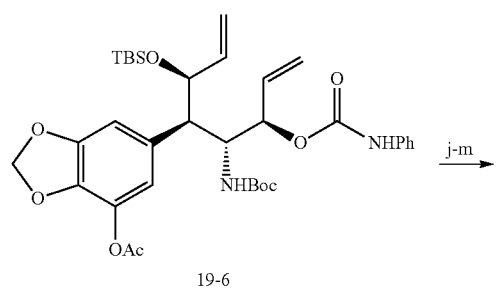

19-6

-continued
Scheme 5-19. Proposed total synthesis of (+)- pancratistatin.

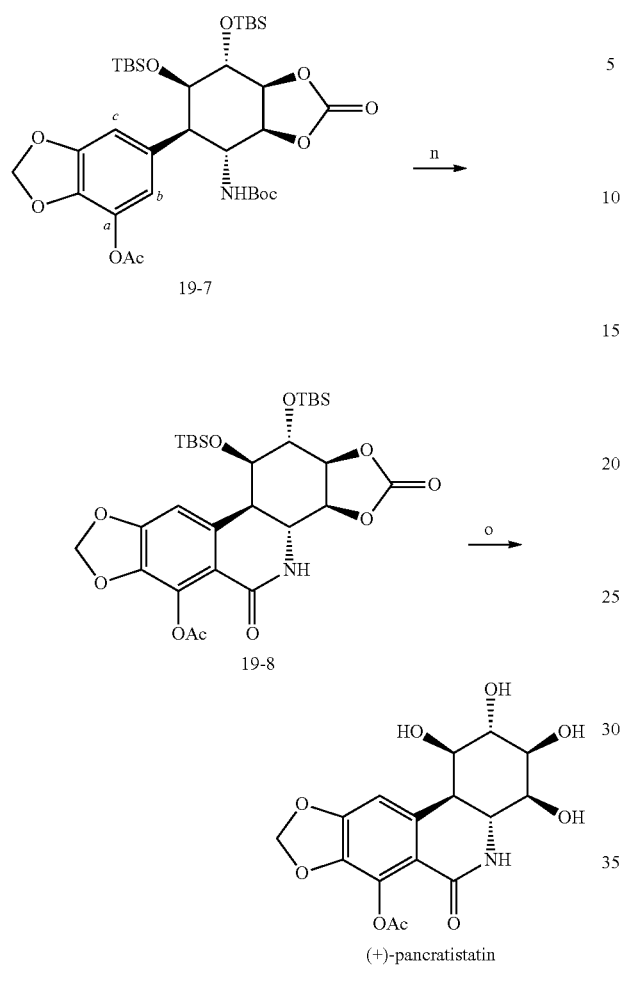

a) (ETO)₃CH₂OTBS, cat. EtCO₂H; b) DIBALH; c) ClSO₂CNO; d) cat. Rh₂TPA₄, PhIO, then 19-2, then DMDO, then NaCNBH₃; e) Boc₂O, Et₃N; f) PhN═C═O, Et₃N; g) H₂O, heat; h) Dess-Martin periodane; i) Ph₃PCH₃Br, KHMDS; j) Grubbs catalyst; k) mCPBA; l) 5% HClO₄; m) TBSCl, imidazole; n) Tf₂O, DMAP; o) NaOMe, MeOH The work described in Part 2 significantly expand the scope of allene oxidation via tunable and stereocontrolled methods to produce diverse stereotriads and tetrads. The utility of these methods can be showcased in total syntheses of lactacystin and (+)-pancratistatin.

Part 3: Application of allene oxidation to the synthesis of pactamycin and novel analogues. In this section, the flexibility of the methods is demonstrated by the description of a formal synthesis of pactamycin and novel analogues to empower structure-activity studies of this potent anti-malarial and antibiotic compound.

There is a continuing need for increasingly efficient methods to prepare bioactive natural products and analogues exhibiting improved activity and specificity. Pactamycin (FIG. 4), the most densely functionalized aminocyclopentitol natural product known, is an excellent target to demonstrate the modularity and flexibility of the new methodologies described herein. The molecule is a potent protease inhibitor and exhibits anti-cancer, antibiotic and anti-malarial activities. However, its synthetic complexity has prevented SAR studies. Recently, genetic engineering has yielded two simple analogues of pactamycin that show nanomolar activity against chloroquine-resistant strains of *Plasmodium falciparum* and a 30-fold decrease in toxicity towards mammalian cells, compared to the parent compound. This report spurs interest in applying an allene oxidation approach to the synthesis of pactamycin and analogues. The stereochemistry and the identity of the heteroatoms can be manipulated with only minor changes to the overall synthetic strategy.

Formal total synthesis of pactamycin. Even though the structure of pactamycin was determined over 50 years ago, there has been only one total synthesis reported to date. The Hanessian group accomplished the synthesis of pactamycin in 32 steps from L-threonine (*Angew. Chem. Int. Ed.* 2011, 50, 3497). Allene oxidation methodology can provide rapid access to the stereochemically dense core of pactamycin in far fewer synthetic steps and with increased flexibility for the preparation of analogues.

Scheme 5-20. Stereotriads present in pactamycin.

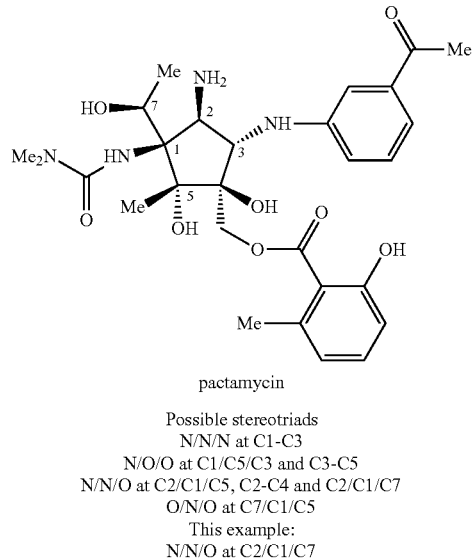

pactamycin
Possible stereotriads
N/N/N at C1-C3
N/O/O at C1/C5/C3 and C3-C5
N/N/O at C2/C1/C5, C2-C4 and C2/C1/C7
O/N/O at C7/C1/C5
This example:
N/N/O at C2/C1/C7

There are several amine-containing stereotriads present in pactamycin that can be obtained through our allene oxidation (Scheme 5-20), but this example focuses efforts on construction of the N/N/O stereotriad at C2/C1/C7 of the molecule. The retrosynthesis in Scheme 5-21 describes the approach to 20-1, which differs from an intermediate reported by Hanessian only in the presence of a primary amine at C2 instead of an azide. This compound is proposed to arise from an intramolecular pinacol-type coupling of 20-2. The substrate for the coupling can be obtained from 20-3, the expected product of the application of the oxidation protocol to 20-4.

Scheme 5-21. Retrosynthesis for pactamycin.

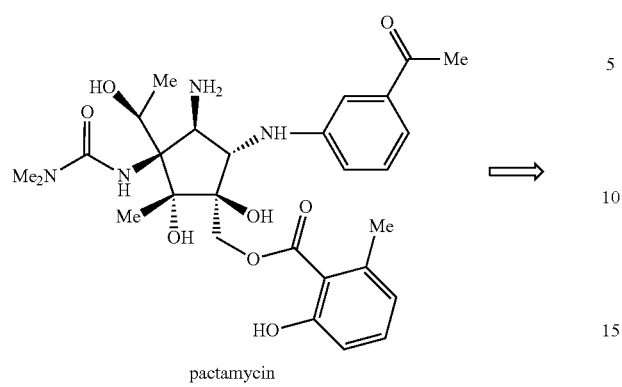

pactamycin

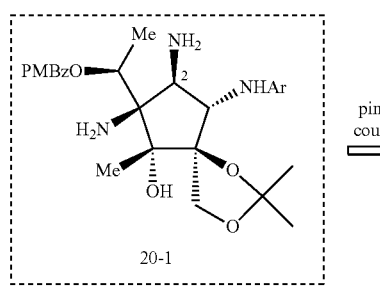

20-1 pinacol coupling

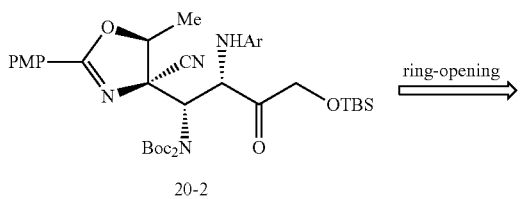

20-2 ring-opening

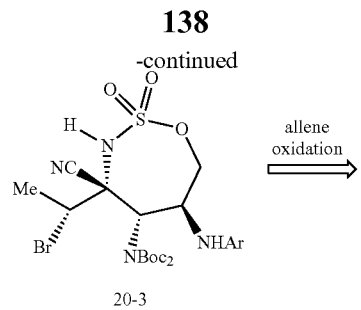

20-3 allene oxidation

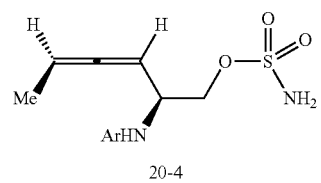

20-4

In the forward synthesis, 21-1 (Scheme 5-22) can be subjected to allene oxidation to yield 21-2. Compound 21-1 can be prepared by minor modifications to a route reported by Krause and co-workers (*Tetrahedron* 2004, 60, 11671). Treatment of 12-2 with p-anisoyl chloride, followed by deprotection of the sulfamate, can unmask the amino alcohol and trigger cyclization of the amide carbonyl onto the secondary Br at C7. This transformation can serve to both invert the stereochemistry at C7 and protect the C1/C7 aminoalcohol as the oxazoline 21-3. Careful oxidation of the terminal alcohol to an aldehyde, addition of $Bu_3SnCHLiOTBS$ and oxidation of the resulting alcohol can give ketone 21-4. If the steric congestion of the nitrile is not sufficient to prevent its reaction with the organometallic reagent, a milder nucleophile, such as an organozinc, can be employed.

Scheme 5-22. Proposed synthesis of pactamycin.

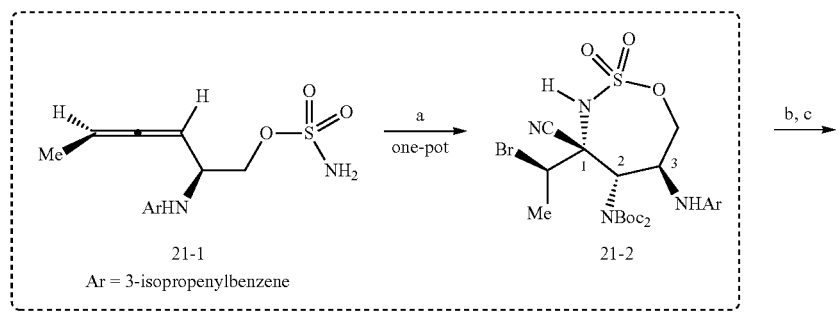

21-1
Ar = 3-isopropenylbenzene 21-2

-continued
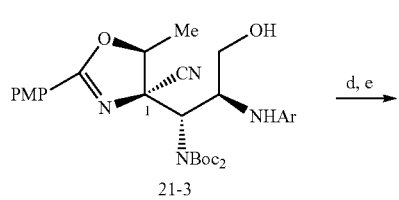
21-3
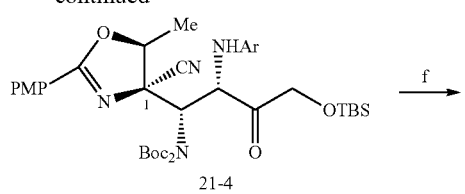
21-4
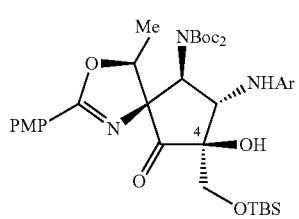
21-5a + C4 diastereomer 21-5b
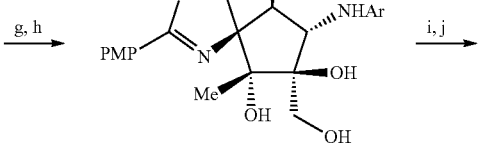
21-6
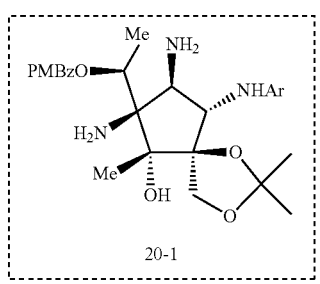
20-1
intermediate similiar to Hanessian's
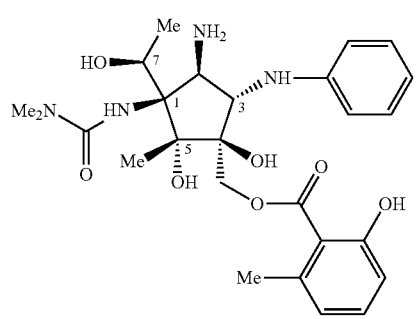
pactamycin
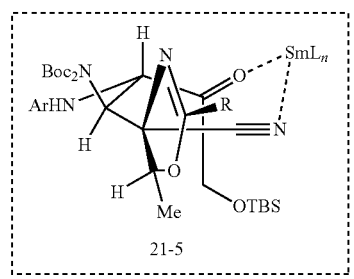
21-5
a) cat. Rh$_2$TPA$_4$, PhIO, then Boc$_2$NLi, then NBS, then TMSCN; b) p-anisoyl chloride, Et$_3$N; c) H$_2$O, heat; d) DMP, then add Bu$_3$SnCH$_2$OTBS/nBuLi, -78° C.
e) Swern; f) SmI$_2$, THF; g) MeMgBr; h) Bu$_4$NF; i) 2N HCl, THF; j) Me$_2$C(OMe)$_2$, cat. CSA Intramolecular pinacol couplings of congested ketoaldehydes are well-precedented, as well as the use of a nitrile as one of the unsaturated coupling partners. $SmI_2$ is the mildest and most commonly employed one-electron reductant, although $TiI_4$, $Cp_2VCl_2/Me_3SiCl/Zn$, and Mg have also been utilized. Diastereocontrol in the reaction of 21-4 can be impacted by the specific reaction conditions, but the large coordination sphere of $SmI_2$ can lead to preferential two-point binding on the top face of 21-5 to yield the desired 21-5a. However, even diastereomer 21-5b can yield valuable SAR data. Because employing a nitrile in the pinacol-type coupling directly installs a ketone at C5, addition of MeMgBr to the top face of the carbonyl can be followed by removal of the TBS group to yield 21-6. The final two reactions are closely based on Hanessian's work and result in cleavage of both the oxazoline and the Boc groups, as well as the installation of an acetonide group on the primary and secondary vicinal alcohols. The preparation of 20-1 essentially represents a formal total synthesis of pactamycin (the primary C2 amine can be converted to an azide by treatment with $TfN_3$), but more importantly, provides an approach that can be easily modified to prepare novel analogues. Preparation of Hanessian's key intermediate required 26 steps, while this route stands at 10 steps. Even if a few extra functional group interconversions or protections need to be invoked, this route is significantly shorter.

Synthesis of novel analogues of pactamycin. Genetic engineering has resulted in two simplified analogues of pactamycin with potent anti-malarial activity and significantly decreased toxicity towards mammalian cells (Scheme 5-23, a=Me and a=Me, b=H). However, modifications in the identity and stereochemistry of the various heteroatoms require a synthetic approach. This provides an excellent opportunity to harness the flexibility of the allene oxidation methodology to prepare a small library of analogues. Amine groups are known to play an important role in both binding and specificity, thus, an initial library of analogues can probe the effect of the amines at C2 and C3, as well as the hydroxyl group located at C7 on the activity of the molecule. The amine at C3 comprises $R^2$ of the substrate 22-1 and can be easily modified during the allene synthesis. This C—N bond can be replaced with both C—O and C—C bonds to determine the effect on the binding affinity and toxicity profile of pactamycin, while the use of different Nu and E in the allene oxidation sequence (Scheme 5-22) can result in modification of the groups at C7 and C2.

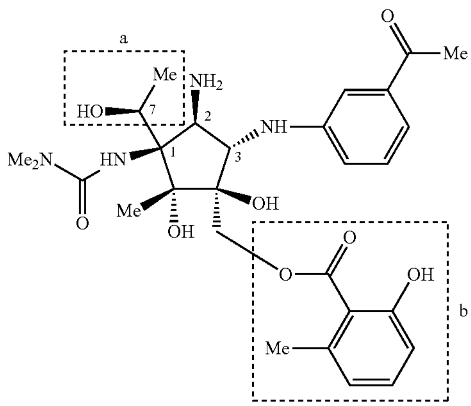

pactamycin 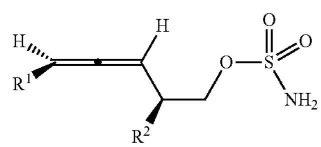 22-1 initial analogue targets 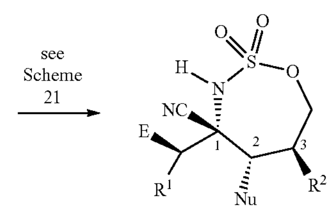 22-2

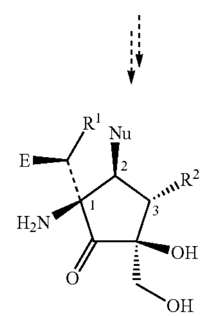

22-3

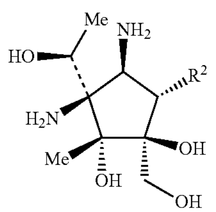

22-4

$R^2$ = OAr, alkyl, aryl 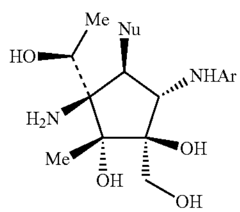 22-5

Nu = OH, SH, Cl, F, $CH_2R$ 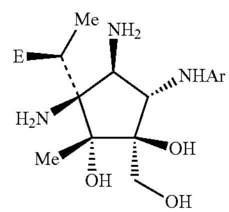 22-6

E = H, $NH_2$, SPh, F, Cl, Br

This example showcases allene oxidation as valuable tools for the total synthesis of the structurally dense and complex aminocyclopentitol natural product, pactamycin. The flexibility of this methodology enables analogue synthesis to aid efforts to understand how the identity and chirality of individual heteroatoms in pactamycin's core structure affect its binding specificity to mammalian vs. bacterial RNA.

In summary, this example provides a solution to the long-standing challenge of synthesizing stereochemically complex amines that occur in many important biologically active molecules. A suite of transformative allene oxidation methods that provide new paradigms for the construction of enantioenriched nitrogenated stereotriads and tetrads is described. These methods are remarkably flexible and permit access to several diastereomeric N/O/O, N/O/N, N/N/O, N/N/N, X/N/Y, C/N/Y, X/N/C/N and X/N/C/O stereotriads and tetrads from a single allene precursor. All of these new methods take advantage of the axial chirality of the allene substrate, enabling the synthesis of enantioenriched stereotriads containing a variety of carbon-carbon and carbon-heteroatom bonds without having to employ any asymmetric catalysis. Three examples, (+)-lactacystin, (+)-pancratistatin and pactamycin, are used to describe how allene oxidation can be applied in total synthesis to streamline the preparation of complex amine-containing natural products.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of forming a bicyclic methylene aziridine by an intramolecular allene aziridination reaction, the method comprising:
   combining an allene of Formula I:

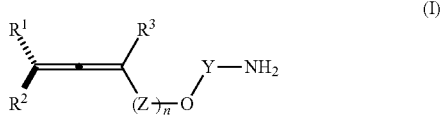

(I)

wherein
$R^1$, $R^2$, and $R^3$ are each independently H, alkyl, cycloalkyl, aryl, heteroaryl, heterocycle, (alkyl)cycloalkyl, (alkyl)aryl, (alkyl)heteroaryl, or (alkyl)heterocycle;
n is 1, 2, or 3;
Y is —C(=O)— or —S(=O)$_2$—; and
each Z is independently —(CH$_2$)—, —(CHR$^1$), or —(CR$^1$)$_2$)—;
a rhodium catalyst selected from the group consisting of Rh$_2$(esp)$_2$ where esp is α,α,α',α'-tetramethyl-1,3-benzenedipropionate, and Rh$_2$(TPA)$_4$ where TPA is triphenylacetate;
a solvent; and
an oxidant;
to yield a reaction mixture, thereby initiating an intramolecular allene aziridination reaction, to provide a bicyclic methylene aziridine; and
contacting the bicyclic methylene aziridine with a nucleophile to provide a nucleophile-addition product.

2. The method of claim 1 wherein the nucleophile-addition product is an enecarbamate or an enesulphone.

3. The method of claim 1 wherein the nucleophile comprises a carboxylic acid, a halide, an alcohol in the presence of an acid, a thiol in the presence of an acid, a cyanide, an azide, a malonate, or an alkyl magnesium nucleophile.

4. The method of claim 1 wherein the bicyclic methylene aziridine is a compound of Formula II:

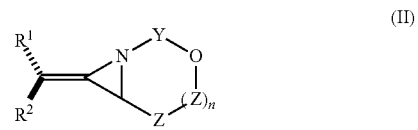

(II)

wherein
$R^1$ and $R^2$ are each independently H, alkyl, cycloalkyl, aryl, heteroaryl, heterocycle, (alkyl)cycloalkyl, (alkyl)aryl, (alkyl)heteroaryl, or (alkyl)heterocycle;
n is 0, 1, or 2;
Y is —C(=O)—or —S(=O)$_2$—; and
each Z is independently —(CH$_2$)—, —(CHR$_1$), or —(CR$^1$)$_2$)—.

5. The method of any one of claims 1, 2, 3, or 4, wherein the nucleophile-addition product is a compound of Formula III:

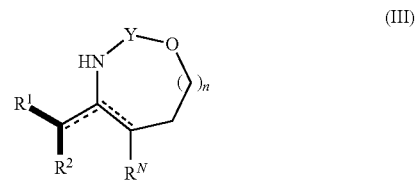

(III)

wherein
$R^1$ and $R^2$ are each independently H, alkyl, cycloalkyl, aryl, heteroaryl, heterocycle, (alkyl)cycloalkyl, (alkyl)aryl, (alkyl)heteroaryl, (alkyl)heterocycle, or azide;
n is 0 or 1;
the dotted lines represent optional double bonds where only one of the double bonds is present;
Y is —C(=O)—or —S(=O)$_2$—; and
$R^N$ is acetoxy, chloroacetoxy, halo, cyano, hydroxyl, alkoxy, thioalkyl, or thioaryl.

6. The method of claim 5 further comprising reacting the nucleophile-addition product with an electrophile to provide an electrophile-addition product.

7. The method of claim 6 further comprising reducing the electrophile-addition product to provide a synthetic motif containing three contiguous carbon-heteroatom bonds.

8. The method of claim 5 further comprising contacting the nucleophile-addition product with a nitrene equivalent in the presence of an oxidant to provide an N,N-spiroaminal.

9. The method of claim 8 wherein the N,N-spiroaminal has four contiguous carbon-heteroatom bonds in the form of a tricyclic 1,4-diazaspiro[2.2]pentane (DASP).

10. The method of claim 9 further comprising contacting the DASP and a nucleophile to provide a bicyclic, ring-opened nucleophile-addition product.

11. A method of forming a bicyclic N,N-aminal, the method comprising:

combining an allene, a rhodium catalyst, a solvent, and an oxidant, to provide a reaction mixture, thereby initiating an intramolecular allene aziridination reaction, to provide a bicyclic methylene aziridine; wherein the allene comprises an allene group tethered to an amino group (—$NH_2$), and the amino group is separated from the nearest carbon atom of the allene group by 3, 4, 5, or 6 atoms linearly;

contacting the bicyclic methylene aziridine with a nitrene equivalent in the presence of an oxidant to provide an N,N-spiroaminal; and contacting the N,N-spiroaminal with a nucleophile to provide a bicyclic, ring-opened nucleophile-addition product.

12. The method of claim 11 wherein the reaction is carried out as a one-pot reaction.

* * * * *